United States Patent
Ghim et al.

(10) Patent No.: US 11,008,367 B2
(45) Date of Patent: *May 18, 2021

(54) COMPOSITIONS AND METHODS FOR TREATING, INCLUDING PREVENTING, PARVOVIRUS INFECTIONS AND RELATED DISEASES

(71) Applicant: UNIVERSITY OF LOUISVILLE RESEARCH FOUNDATION, INC., Louisville, KY (US)

(72) Inventors: Shin-je Ghim, Louisville, KY (US); A. Bennett Jenson, Louisville, KY (US); John O. Trent, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 76 days.

This patent is subject to a terminal disclaimer.

(21) Appl. No.: 16/233,386

(22) Filed: Dec. 27, 2018

(65) Prior Publication Data

US 2019/0202867 A1 Jul. 4, 2019

Related U.S. Application Data

(62) Division of application No. 15/124,699, filed as application No. PCT/US2015/019664 on Mar. 10, 2015, now Pat. No. 10,214,565.

(60) Provisional application No. 61/950,623, filed on Mar. 10, 2014.

(51) Int. Cl.
| | | |
|---|---|---|
| C07K 14/005 | (2006.01) | |
| A61K 39/12 | (2006.01) | |
| C12N 7/00 | (2006.01) | |
| A61K 39/23 | (2006.01) | |
| C12N 15/85 | (2006.01) | |
| C12P 21/02 | (2006.01) | |
| A61K 39/00 | (2006.01) | |

(52) U.S. Cl.
CPC ............ *C07K 14/005* (2013.01); *A61K 39/12* (2013.01); *A61K 39/23* (2013.01); *C12N 7/00* (2013.01); *C12N 15/85* (2013.01); *C12P 21/02* (2013.01); *A61K 2039/5258* (2013.01); *A61K 2039/55511* (2013.01); *A61K 2039/55566* (2013.01); *A61K 2039/575* (2013.01); *C12N 2710/14043* (2013.01); *C12N 2750/14222* (2013.01); *C12N 2750/14223* (2013.01); *C12N 2750/14234* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 5,508,186 A | 4/1996 | Young et al. |
| 5,827,647 A | 10/1998 | Young et al. |
| 5,916,563 A | 6/1999 | Young et al. |
| 6,001,371 A | 12/1999 | Young et al. |
| 6,132,732 A | 10/2000 | Young et al. |
| 6,558,676 B1 | 5/2003 | Young et al. |
| 6,818,612 B2 | 11/2004 | Broliden et al. |
| 10,214,565 B2 | 2/2019 | Ghim et al. |
| 2003/0017596 A1 | 1/2003 | Broliden et al. |
| 2003/0170612 A1 | 9/2003 | Pichuantes et al. |
| 2013/0052226 A1 | 2/2013 | Zhi et al. |
| 2013/0345400 A1 | 12/2013 | Eloit et al. |
| 2017/0015712 A1 | 1/2017 | Ghim et al. |

FOREIGN PATENT DOCUMENTS

| | | |
|---|---|---|
| CA | 2474032 A1 | 1/2006 |
| CA | 2474032 C | 1/2006 |
| WO | 2013/006838 A1 | 1/2013 |
| WO | 2013/016460 A1 | 1/2013 |

OTHER PUBLICATIONS

Manaresi and Gallinella, Viruses, 2019, 11, 659, 21 pages. (Year: 2019).*
Restriction Requirement in U.S. Appl. No. 15/124,699 dated Aug. 21, 2017, 9 pages.
NonFinal Office action in U.S. Appl. No. 15/124,699 dated Jan. 23, 2018, 21 pages.
Final Office action in U.S. Appl. No. 15/124,699 dated Jun. 6, 2018, 19 pages.
Notice of Allowance in U.S. Appl. No. 15/124,699 dated Oct. 2, 2018, 14 pages.
Hurtado et al., "Identification of Domains in Canine Parvovirus VP2 Essential for the Assembly of Virus-Like Particles" Journal of Virology (1996) vol. 70, No. 8, pp. 5422

(56) References Cited

OTHER PUBLICATIONS

Shade et al., "Nucleotide Sequence and Genome Organization of Human Parvovirus B19 Isolated from the Serum of a Child during Aplastic Crisis" Journal of Virology (1986) vol. 58, No. 3, pp. 921-936.
PCT/US2015/019664, ISR/WO dated Jun. 10, 2015, 10 pages. ##.
Ballou et al., "Safety and Immunogenicity of a Recombinant Parvovirus B19 Vaccine Formulated with MF59C.1" J. Infect. Dis. (2003) vol. 187, pp. 675-678. ##.
Bansal et al., "Candidate recombinant vaccine for human B19 parvovirus" J. Infect Dis. (1993) vol. 167, pp. 1034-1044. ##.
Bernstein et al., "Safety and immunogenicity of a candidate parvovirus B19 vaccine" Vaccine (2011) vol. 29, pp. 7357-7363. ##.
Bönsch et al., "Interaction of parvovirus B19 with human erythrocytes alters virus structure and cell membrane integrity" J Virol. (2008) vol. 82, No. 23, pp. 11784-11791. ##.
Bönsch et al., "The Globoside receptor triggers structural changes in the B19 virus capsid that facilitate virus internalization" J Virol. (2010) vol. 84, No. 22, pp. 11737-11746. ##.
Broliden et al., "Clinical aspects of parvovirus B19 infection" J. Intern Med. (2006) vol. 260, pp. 285-304. ##.
Brown et al., "Resistance to parvovirus B 19 infection due to lack of virus receptor (erythrocyte P antigen)" N Engl J Med (1994) vol. 330, No. 17, pp. 1192-1196. ##.
Chipman et al., "Cryo-electron microscopy studies of empty capsids of human parvovirus B19 complexed with its cellular receptor" Proc Natl Acad Sci U S A (1996) vol. 93, No. 15, pp. 7502-7506. ##.
Corcoran et al., "Establishment of functional B cell memory against parvovirus B19 capsid proteins may be associated with resolution of persistent infection" J Med Virol. (2006) vol. 78, pp. 125-128. ##.
Dijkmans et al., "Parvovirus B19 in pregnancy: prenatal diagnosis and management of fetal complications" Curr Opin Obstet Gynecol. (2012) vol. 24, No. 2, pp. 95-101. ##.
Dorsch et al., "The VP1 unique region of parvovirus B19 and its constituent phospholipase A2-like activity" J Virol. (2002) vol. 76, No. 4, pp. 2014-2018. ##.
Ekman et al., "Biological and immunological relations among human parvovirus B19 genotypes 1 to 3" J. Virol. (2007) vol. 81, No. 13, pp. 6927-6935. ##.
GenBank Ref. No. NC_000883.2, 6 pages. ##, (2015).
Gigler et al., "Generation of neutralizing human monoclonal antibodies against parvovirus B19 proteins" J. Virol. (1999) vol. 73, No. 3, pp. 1974-1979. ##.
Gribskov et al., "PEPPLOT, a protein secondary structure analysis program for the UWGCG sequence analysis software package" Nucleic Acids Research (1986a) vol. 14, No. 1, pp. 327-334. ##.
Gribskov et al., "Sigma factors from *E. coli*, B. subtilis, phage SP01, phage T4 are homologous proteins" Nucleic Acids Research (1986b) vol. 14, No. 16, pp. 6745-6763. ##.
Kajigaya et al., "Self-assembled B19 parvovirus capsids, produced in a baculovirus system, are antigenically and immunogenically similar to native virions" Proc Natl Acad Sci U S A (1991) vol. 88, No. 11, pp. 4646-4650. ##.
Kaufmann et al., "The structure of human parvovirus B19" Proc Natl Acad Sci U S A (2004) vol. 101, No. 32, pp. 11628-11633. ##.
Kawase et al., "Modest Truncation of the Major Capsid Protein Abrogates B19 Parvovirus Capsid Formation" J of Virology (1995) vol. 69, No. 10, pp. 6567-6571. ##.
Miyamura et al., "Parvovirus particles as platforms for protein presentation (capsid/B19/lysozyme/gene therapy/vaccine)" PNAS (1994) vol. 91, pp. 8507-8511. ##.
Needleman et al. "A General Method Applicable to the Search for Similarities in the Amino Acid Sequence of Two Proteins" J. Mol. Biol. (1970) vol. 48, p. 443-453. ##.
Norbeck et al., "Parvovirus B19 capsid protein VP2 inhibits hematopoiesis in vitro and in vivo: Implications for therapeutic use" Experimental Hematology (2004) vol. 32, pp. 1082-1087. ##.

Ros et al., "Conformational Changes in the VP1-Unique Region of Native Human Parvovirus B19 Lead to Exposure of Internal Sequences That Play a Role in Virus Neutralization and Infectivity" J of Virology (2006) vol. 80, No. 24, pp. 12017-12024. ##.
Rosenfeld et al., "Unique region of the minor capsid protein of human parvovirus B19 is exposed on the virion surface" J. Clin. Invest. (1992) vol. 89, No. 6, pp. 2023-2029. ##.
Saikawa et al., "Neutralizing linear epitopes of B19 parvovirus cluster in the VPI Unique and VP1-VP2 junction regions" J. Virol. (1993) vol. 67, No. 6, pp. 3004-3009. ##.
Servant-Delmas et al., "Advances in human B19 parvovirus biology" J. Virol. (2010) vol. 84, No. 19, pp. 9658-9665. ##.
Smith et al. "Comparison of biosequences" Adv. Appl. Math. (1981) vol. 2, p. 482-489. ##.
Wong et al. "Ex vivo-generated CD36+ erythroid progenitors are highly permissive to human parvovirus B19 replication" J. Virol. (2008) vol. 82, No. 5, pp. 2470-2476. ##.
Yoshimoto et al., "A second neutralizing epitope of B 19 parvovirus implicates the spike region in the immune response" J. Virol. (1991) vol. 65, No. 12, pp. 7056-7060. ##.
EP 15762030.3, Partial Search Report dated Sep. 19, 2017, (27 pages). ##.
EP 15762030.3, Partial Search Report dated Sep. 19, 2017, (26 pages). ##.
EP 15762030.3, Response to Partial Search Report filed Jul. 24, 2018 (8 pages). ##.
Agbandje McKenna et al., "Functional implications of the structure of the murine parvovirus, minute virus of mice" Structure (1998) vol. 6, pp. 1369-1381. ##.
Boudreaux et al., "Rotavirus core shell subdomains involved in polymerase encapsidation into virus-like particles" Journal of General Virology (2013) vol. 94, pp. 1818-1826. ##.
Chandramouli et al., "Generation of a parvovirus B19 vaccine candidate" Vaccine (2013) vol. 31, pp. 3872-3878. ##.
Engler et al., "Induction and Measurement of In Vivo Antibody Responses" Current Protocols in Immunology (1991) vol. 00, pp. 7.16.1-7.16.7 (doi:10.1002/0471142735.im07016s00). ##.
Erdman et al., "Detection of Human Parvovirus B19 DNA PCR Products by RNA Probe Hybridization Enzyme Immunoassay" Journal of Clinical Microbiology (1994) vol. 32, No. 9, pp. 2295-2298. ##.
Ghim et al., "HPV-1 L1 Protein Expressed in cos Cells Displays Conformational Epitopes Found on Intact Virions" Virology (1992) vol. 190, pp. 548-552. ##.
Ho et al., "Vaccine development through terminal deletions of an infectious bursal disease virus protein 2 precursor variant" Process Biochemistry (2010) vol. 45, pp. 786-793. ##.
Hornbeck "Double-Immunodiffusion Assay for Detecting Specific Antibodies" Current Protocols in Immunology (1991) vol. 00, pp. 2.3.1-2.3.4. (doi:10.1002/0471142735.im0203s00). ##.
James "Measurement of Proliferative Responses of Cultured Lymphocytes" Current Protocols in Immunology (1994) vol. 11, pp. 7.10.1-7.10.10. (doi:10.1002/0471142735.im0710s11). ##.
Joh et al., "Epidemiological and phylogenetic analysis of institutional mouse parvoviruses" Experimental and Molecular Pathology (2013) vol. 95, pp. 32-37. ##.
Lopez De Turiso et al., "Recombinant Vaccine for Canine Parvovirus in Dogs" Journal of Virology (1992) vol. 66, No. 5, pp. 2748-2753. ##.
Rosenfeld et al., "Subunit interaction in B19 parvovirus empty capsids" Arch Virol (1994) vol. 136, pp. 9-18. ##.
Schwartz et al., Chapter 23 "Matrices for Detecting Distant Relationships" at pp. 353-358 in Atlas of Protein Sequence and Structure, Editor Dayhoff (1978) National Biomedical Research Foundation, Wash. D.C. ##.
Vogel et al., Chapter 7 "A Compendium of Vaccine Adjuvants and Excipients" at pp. 141-228 in Vaccine Design, The Subunit and Adjuvant Approach, Editors Powell et al. (1995) Plenum Press, New York. ##.
Boslego et al. (1991) "Efficacy trial of a parenteral gonococcal pilus vaccine in men" Vaccine, vol. 9, pp. 154-162.

\* cited by examiner

A

B

C

D

A    Wild Type VLP

B    mVLPs made with Construct A

C mVLPs made with Construct B

D mVLPs made with Construct D

E    mVLPs made with Construct E

F    mVLPs made with Construct F

G mVLPs made with Construct F

H mVLPs made with Construct G mVLPs made with Construct H

FIG. 3

Hemagglutination assays using Type O human red blood cells

FIG. 4

HIA Assays of rabbit and mouse raise polyclonal antibodies

Binding to the P antigen of a red blood cell.

A

Cartoon representation of hamagglutination of red blood cells by B19 virions.

(a) Infectious B19 virion/virus may not be high immunogenic because of hemagglutination of RBC by B19 virions and theoretical inaccessibility to B19 virus by B cells

Cartoon representation of hamagglutination of red blood cells by B19 wtVLPs.

(b) Due to internalization of wild type VLPs by Hemagglutination of RBCs, wild type VLPs can be not readily accessible by B cells

Cartoon representation of hamagglutination of red blood cells by B19 mVLPs.

(c) Abundant free mutated B19 VLPs in vivo resulting exposure of neutralizing epitopes on mutated VLPs and induction of high titer neutralizing antibodies as a consequence

COMPOSITIONS AND METHODS FOR TREATING, INCLUDING PREVENTING, PARVOVIRUS INFECTIONS AND RELATED DISEASES

CROSS-REFERENCE TO RELATED APPLICATIONS

This application is a divisional of Ser. No. 15/124,699 with a 371(c) date of Sep. 9, 2016 entitled "COMPOSITIONS AND METHODS FOR TREATING, INCLUDING PREVENTING, PARVOVIRUS INFECTIONS AND RELATED DISEASES" which is herein incorporated by reference in its entirety, and which is a National Stage Entry of International Application No. PCT/US2015/019664 filed Mar. 10, 2015, entitled "COMPOSITIONS AND METHODS FOR TREATING, INCLUDING PREVENTING, PARVOVIRUS INFECTIONS AND RELATED DISEASES" which is herein incorporated by reference in its entirety, and which claims the benefit of U.S. Provisional Application No. 61/950,623, filed Mar. 10, 2014, entitled "COMPOSITION AND METHOD FOR TREATING PARVOVIRUS B19 INFECTION" which is herein incorporated by reference in its entirety.

BACKGROUND

Parvovirus is the common name used to refer to all of the viruses in the Parvoviridae family. Erythrovirus is a genus of the Parvoviridae family containing viruses that infect erythrocyte progenitor cells. Erythroviruses and parvoviruses can infect many animals (e.g., mammals, porcine, canine, feline, primates, monkeys, and humans). Human erythroviruses contains three genotypes (Servant-Delmas et al., J Virol. (October 2010) Vol. 84, No. 19, pp. 9658-9665). Genotype 1 includes parvovirus B19 (also referred to as erythrovirus B19) and two new genotypes with a genetic diversity markedly distinct (>9% nucleotide divergence on the whole genome) from that of provirus B19. Genotype 2 includes the Lali strain and the A6 strain, genotype 3a the V9 strain, and genotype 3b the D91.1 strain. In certain instances, the clinical spectrum associated with genotype 2 or 3 virus infection can be similar to that observed with parvovirus B19, a genotype 1, infection.

Parvovirus B19 (a species of the erythrovirus genus) can cause severe and sometimes fatal diseases in fetuses and newborns, such as hydrops fetalis, intrauterine fetal death and erythema infectiosum (fifth disease) in children. Older human children and adults with either hereditary diseases (e.g., sickle cell anemia or Thalassemia) or acquired diseases (e.g., malaria or anemia) are at risk for developing parvovirus B19-induced red cell aplasia or death. Chronic anemia in immunodeficient, organ transplant, or HIV patients has contributed to parvovirus B19 infection. A cellular receptor for parvovirus B19 is the blood group P antigen, a globoside, that is expressed in erythroid precursors and maintained on mature red blood cells (RBCs). To date, no vaccine is available to prevent human erythrovirus, including parvovirus B19 infection. Accordingly, some embodiments of the present invention include treating (e.g., preventing or vaccinating against) erythrovirus infection (e.g., parvovirus B19 infection and other erythroviruses).

Some embodiments of the invention include inventive polypeptides (e.g., mutant VP2 proteins) and virus-like particles made from the inventive polypeptides. Other embodiments of the invention include compositions for treating (e.g., preventing) erythrovirus infections, including parvovirus B19 infection and other diseases. Further embodiments include methods for treating active erythrovirus infections, including active parvovirus B19 infection and other diseases. Still other embodiments include nucleic acids that encode the inventive polypeptides. Additional embodiments of the invention are also discussed herein.

SUMMARY

Some embodiments of the present invention include a polypeptide comprising a VP2 polypeptide with at least one amino acid modification relative to wild type VP2. In some instances, at least one amino acid modification is an insertion, a deletion, or a substitution. In other instances, the wild type VP2 has the amino acid sequence of SEQ ID NO: 1. In certain embodiments, the polypeptide forms an mVLP, which can, in some examples, have a reduced binding capacity to P antigen relative to wtVLP. In other embodiments, an amino acid modification is in or near the recess of the three-fold axis. In yet other embodiments, an amino acid modification is selected from a substitution in loop 3, a substitution in loop 4, a substitution upstream of loop 3, a substitution upstream of loop 4, or combinations thereof. In still other embodiments, the amino acid modification is a substitution at Y401, a substitution at Q399, a substitution at Q400, a substitution at Q404, a substitution at Q368, a substitution at Q369, a substitution at Y392, or combinations thereof. The amino acid modification can also, in some instances, be Y401F, Y401W, Y401A, Q368A, Q369A, Q368N, Q369N, Q399N, Q400N, Q404T, Y392A, Y392F, Q404N, Y401P, T402A, D403A, Q404A, or combinations thereof. In some embodiments, the wild type VP2 is a wild type VP2 from parvovirus B19. In some aspects, the polypeptide is selected from construct A, construct B, construct C, construct D, construct E, construct F, construct G, construct H, construct I, construct J, construct K, construct L, construct M, construct N, construct O, construct P, construct Q, construct R, construct S, construct T, construct U, construct V, construct W, and construct X. In other embodiments, the polypeptide sequence has at least 90% identity to SEQ ID NO: 1.

In some embodiments of the invention, mVLP comprises any mutant VP2 as described herein. In other embodiments, the mVLP has reduced binding to P antigen compared to wtVLP, the mVLP has no detectable binding to P antigen, the mVLP has reduced hemagglutination of red blood cells compared to wtVLP, or the mVLP has no detectable hemagglutination. In still other embodiments, the mVLP has one or more neutralizing epitopes. In yet further embodiments, the mVLP induces the production of antibodies (e.g., a high titer of antibodies) in an animal, where the antibodies produced are capable of reducing or inhibiting hemagglutination by wtVLP.

Some embodiments of the invention include a composition comprising any mVLP as described herein. The composition, in some instances, includes an amount of mVLP from about 0.0001% (by weight total composition) to about 99%. The composition can further comprise an adjuvant or a carrier, in some embodiments. Aspects of the invention also include pharmaceutical compositions comprising any mVLP as described herein. In some embodiments, pharmaceutical compositions can include an amount of mVLP from about 0.0001% (by weight total composition) to about 50%. In certain instances, the pharmaceutical compositions can further comprising an adjuvant or a carrier. In certain embodiments, the vaccine comprises any mVLP as described herein. In some embodiments, the vaccine can include an amount of mVLP from about 0.0001% (by weight total composition) to about 50%. In other instances, the vaccine further comprises an adjuvant or a carrier. In certain embodiments, the vaccine further comprises squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, cell wall skeleton, ADJUPLEX™ vaccine adjuvant, MF59, TITERMAX®, or combinations thereof. In still other embodiments, the vaccine does not comprise an adjuvant.

Some embodiments of the invention include methods for providing an animal with an mVLP comprising one or more administrations of one or more compositions comprising any mVLP described herein, where the compositions may be the same or different if there is more than one administration. In certain aspects, the one or more compositions do not comprise an adjuvant. In other aspects, the one or more compositions further comprise a carrier, an adjuvant, squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, cell wall skeleton, ADJUPLEX™ vaccine adjuvant, MF59, TITERMAX®, or combinations thereof. In other embodiments, the one or more compositions comprise (a) any composition described herein, (b) any pharmaceutical composition described herein, or (c) any vaccine described herein. In still other embodiments, one or more administration can comprise parenteral administration, a mucosal administration, intravenous administration, subcutaneous administration, topical administration, intradermal administration, oral administration, sublingual administration, intranasal administration, or intramuscular administration. In some instances, if there is more than one administration at least one composition used for at least one administration is different from the composition of at least one other administration. In yet other embodiments, the mVLP of at least one of the one or more compositions is administered to the animal in an amount of from about 0.01 mg of mVLP/kg animal body weight to about 15 mg of mVLP/kg animal body weight. The animal is a human or a primate, in certain instances.

Some embodiments of the invention include methods for treating an animal for a parvovirus infection, a disease related to a parvovirus infection, an erythrovirus infection, a disease related to an erythrovirus infection, a parvovirus B19 infection, or a disease related to a parvovirus B19 infection, comprising one or more administrations of one or more compositions comprising any mVLP as described herein, wherein the compositions may be the same or different if there is more than one administration. In certain aspects, the one or more compositions do not comprise an adjuvant. In other aspects, the one or more compositions further comprise a carrier, an adjuvant, squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, cell wall skeleton, ADJUPLEX™ vaccine adjuvant, MF59, TITERMAX®, or combinations thereof. In other embodiments, the one or more compositions comprise (a) any composition described herein, (b) any pharmaceutical composition described herein, or (c) any vaccine described herein. In still other embodiments, one or more administration can comprise parenteral administration, a mucosal administration, intravenous administration, subcutaneous administration, topical administration, intradermal administration, oral administration, sublingual administration, intranasal administration, or intramuscular administration. In some instances, if there is more than one administration at least one composition used for at least one administration is different from the composition of at least one other administration. In yet other embodiments, the mVLP of at least one of the one or more compositions is administered to the animal in an amount of from about 0.01 mg of mVLP/kg animal body weight to about 15 mg of mVLP/kg animal body weight. The animal is a human or a primate, in certain instances. In other embodiments, the animal is in need of the treatment. Some embodiments include methods for treating an animal for an erythrovirus infection, a disease related to an erythrovirus infection, a parvovirus B19 infection, or a disease related to a parvovirus B19 infection. While still other embodiments the method is for treating an erythrovirus infection, a parvovirus B19 infection, a disease related to an erythrovirus infection, a disease related to parvovirus B19 infection, hydrops fetalis intrauterine fetal death, erythema infectiosum (i.e., fifth disease), sickle cell anemia, Thalassemia, anemia, anemia induced by malaria, parvovirus B19-induced red cell aplasia (TRCA), chronic anemia, acute arthropathy, persistent arthropathy, aplastic crisis, arthritis, hepatitis, myocarditis, hepatosplenomegaly, systemic lupus erythematosus, meningoencephalitis, or fibromyalgia. In some embodiments, the method induces an immune response, is a vaccination, is a prophylactic treatment, is a therapeutic treatment, or is a combination thereof.

Some aspects of the present invention include methods for inducing an immune response in an animal comprising one or more administrations of one or more compositions comprising any mVLP disclosed herein, wherein the compositions may be the same or different if there is more than one administration. In certain aspects, the one or more compositions do not comprise an adjuvant. In other aspects, the one or more compositions further comprise a carrier, an adjuvant, squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, cell wall skeleton, ADJUPLEX™ vaccine adjuvant, MF59, TITERMAX®, or combinations thereof. In other embodiments, the one or more compositions comprise (a) any composition described herein, (b) any pharmaceutical composition described herein, or (c) any vaccine described herein. In still other embodiments, one or more administration can comprise parenteral administration, a mucosal administration, intravenous administration, subcutaneous administration, topical administration, intradermal administration, oral administration, sublingual administration, intranasal administration, or intramuscular administration. In some instances, if there is more than one administration at least one composition used for at least one administration is different from the composition of at least one other administration. In yet other embodiments, the mVLP of at least one of the one or more compositions is administered to the animal in an amount of from about 0.01 mg of mVLP/kg animal body weight to about 15 mg of mVLP/kg animal body weight. The animal is a human or a primate, in certain instances. In other embodiments, the animal is in need of the treatment. In still other embodiments, the method prevents or ameliorates future infections.

Some embodiments of the present invention include methods for vaccinating an animal against a parvovirus infection, an erythrovirus infection, or a parvovirus B19 infection, comprising one or more administrations of one or more compositions comprising any mVLP disclosed herein, wherein the compositions may be the same or different if there is more than one administration. In certain aspects, the one or more compositions do not comprise an adjuvant. In other aspects, the one or more compositions further comprise a carrier, an adjuvant, squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, cell wall skeleton, ADJUPLEX™ vaccine adjuvant, MF59, TITERMAX®, or combinations thereof. In other embodiments, the one or more compositions comprise (a) any composition described herein, (b) any pharmaceutical composition described herein, or (c) any vaccine described herein. In still other embodiments, one or more administration can comprise parenteral administration, a mucosal administration, intravenous administration, subcutaneous administration, topical administration, intradermal administration, oral administration, sublingual administration, intranasal administration, or intramuscular administration. In some instances, if there is more than one administration at least one composition used for at least one administration is different from the composition of at least one other administration. In yet other embodiments, the mVLP of at least one of the one or more compositions is administered to the animal in an amount of from about 0.01 mg of mVLP/kg animal body weight to about 15 mg of mVLP/kg animal body weight. The animal is a human or a primate, in certain instances. In other embodiments, the animal is susceptible to a parvovirus infection, an erythrovirus infection, or a parvovirus B19 infection. In still other embodiments, the method is for vaccinating against an erythrovirus infection or a parvovirus B19 infection. In yet other embodiments, the method prevents or ameliorates future infections or future diseases.

Some embodiments of the present invention include methods for producing any polypeptide as described herein comprising, culturing the host cell transfected with a vector comprising a nucleic acid sequence encoding the polypeptide, to provide expression; and then recovering the polypeptide. In certain embodiments, preparing the vector comprises reverse transcription using RNA or de novo synthesis. In other aspects, the host cell is an insect cell (e.g., an Sf9 cell) or a mammalian cell. Other embodiments include the nucleic acid sequence encoding the polypeptide being selected from the group consisting of SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; and SEQ ID NO: 26.

Some embodiments of the present invention include methods for producing any mVLP as described herein comprising, culturing a host cell transfected with a vector comprising a nucleic acid sequence encoding an inventive polypeptide, to provide expression of the inventive polypeptide; and then recovering the mVLP. In certain embodiments, preparing the vector comprises reverse transcription using RNA or de novo synthesis. In other aspects, the host cell is an insect cell (e.g., an Sf9 cell) or a mammalian cell. Other embodiments include the nucleic acid sequence encoding the polypeptide being selected from the group consisting of SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; and SEQ ID NO: 26.

Some embodiments of the present invention include nucleic acid molecules encoding any polypeptide described herein. In other embodiments, the nucleic acid sequence encoding the polypeptide is selected from the group consisting of SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; and SEQ ID NO: 26. While in other embodiments, the nucleic acid sequence has at least 90% identity to SEQ ID NO: 2. In still other embodiments, the nucleic acid molecule is in a cell, an insect cell, a mammalian cell, a human cell, or an Sf9 insect cell. In still other embodiments, the nucleic acid molecule is included in a vector or plasmid. Some embodiments of the present invention include a vector comprising a nucleic acid molecule encoding any polypeptide described herein.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 4: Hemagglutination inhibition assays (HIA) of rabbit and mouse polyclonal antibodies against VLPs. Hemagglutination inhibition assays (HIA) were used to determine the inhibition of hemagglutination by polyclonal antibodies raised against wtVLPs or mVLPs in mice and rabbits.

DETAILED DESCRIPTION

Parvovirus is the common name used to refer to all of the viruses in the Parvoviridae family. Erythrovirus is a genus of the Parvoviridae family containing viruses that infect erythrocyte progenitor cells. Erythroviruses and parvoviruses can infect many animals (e.g., mammals, porcine, canine, feline, primates, monkeys, and humans). Human erythroviruses contains three genotypes (Servant-Delmas et al., J Virol. (October 2010) Vol. 84, No. 19, pp. 9658-9665). Genotype 1 includes parvovirus B19 (also referred to as erythrovirus B19) and two new genotypes with a genetic diversity markedly distinct (>9% nucleotide divergence on the whole genome) from that of provirus B19. Genotype 2 includes the Lali strain and the A6 strain, genotype 3a the V9 strain, and genotype 3b the D91.1 strain. In certain instances, the clinical spectrum associated with genotype 2 or 3 virus infection can be similar to that observed with parvovirus B19, a genotype 1, infection. Parvoviruses appear to have between 2-4 polypeptides including VP1 and VP2 capsid polypeptides; erythroviruses also appear to have a VP2 capsid polypeptide. Parvovirus B19 includes in its capsid a VP2 polypeptide.

Figure 5:
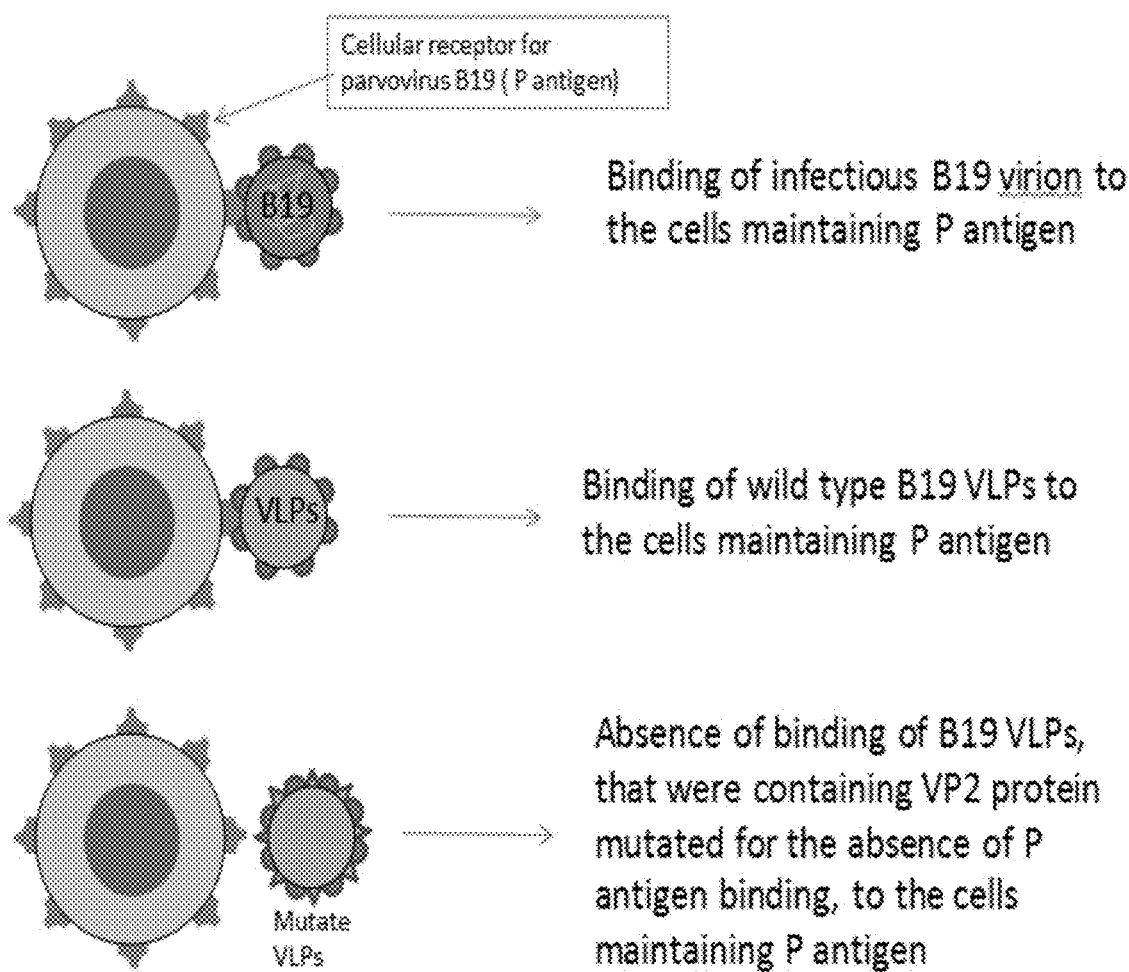
FIG. 5: A cartoon representation of P antigen binding. Without wishing to be bound by any theory or mechanism implied by the cartoon, this cartoon shows an embodiment of binding (or absence thereof) to the P antigen on the red blood cell surface by the B19 viron, a B19 wtVLP, and a representative embodiment of a B19 mVLP.
Figure 6:
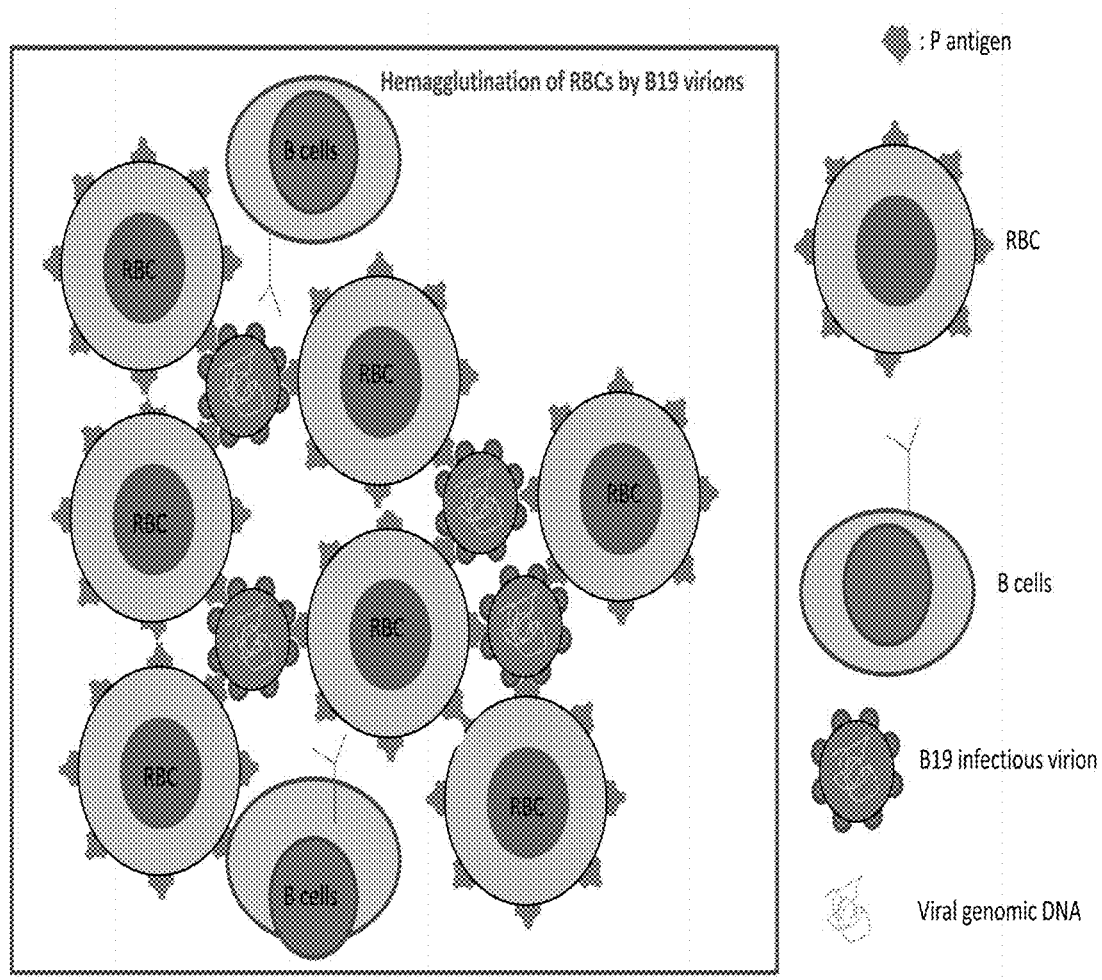
FIG. 6: Cartoon representations of hemagglutination. (A) Without wishing to be bound by any theory or mechanism implied by the cartoon, this cartoon shows an embodiment of the reaction that could occur between B19 infectious virus and red blood cells (RBCs) to form hemagglutination which may occur in vivo. (B) Without wishing to be bound by any theory or mechanism implied by the cartoon, this cartoon shows an embodiment of the reaction that could occur between wild type B19 VLPs maintaining ligand capable of binding to P antigen on RBCs so that RBCs aggregate and preclude presentation of B19 VLPs to B cells. (C) Without wishing to be bound by any theory or mechanism implied by the cartoon, this cartoon shows an embodiment of the reaction that could occur between B19 mVLPs due to an absence of binding to P antigen on RBCs; this could result in abundance of free B19 mVLPs that can be presented to B cells.

Parvovirus B19 consists of approximately 5.6 kb single-stranded genomic DNA (NCBI reference sequence NC_000883.2) that encodes one nonstructural protein (NS1), two structural proteins (VP1 and VP2), and 7.5 and 11 KD proteins. Genes spanning from nt 2624 to nt 4969 encode VP1 (minor) and VP2 (major) capsid proteins. VP2 protein (58KD) overlaps C-terminus of VP1, and is composed of at least 95% of capsid. VP1 protein (81KD) is 227 amino acids longer than VP2 and consists of only 5% of capsid proteins. P antigen is a cellular receptor of Parvovirus B19; Ku80 autoantigen and α5β1 intergrin are co-receptors for the entry of Parvovirus B19 into cells. In some instances (e.g., see FIG. 5 and FIG. 6), P antigen binding by parvovirus B19 can result in hemagglutination and thus can block access of B cells to parvovirus B19; this lack of access can, in some instances, prevent an immune response.

Inventive Polypeptides, Nucleic Acid Molecules, and Compositions

Some embodiments of the invention include inventive polypeptides comprising a VP2 polypeptide, where the VP2 polypeptide has at least one amino acid modification relative to wild type VP2 ("wtVP2"). The term "VP2 polypeptide" encompasses mutant VP2 polypeptides (e.g., with one or more modifications made to a wtVP2 polypeptide) and wtVP2 polypeptides. A wtVP2 polypeptide can, in some embodiments, be a wild type VP2 polypeptide from a parvovirus, a wild type VP2 polypeptide from an erythrovirus, or a wild type VP2 polypeptide from a parvovirus B19. One or more modifications, in some instances, can include an insertion, a deletion, a substitution, or combinations thereof. In some embodiments, one or more modifications to wtVP2 can be in or near (e.g., near can be a distance of about 5 Å, about 10 Å, about 15 Å, about 20 Å, about 25 Å, about 30 Å, about 35 Å, about 40 Å, about 45 Å, about 50 Å, less than about 50 Å or less than about 30 Å) the recess of the three-fold axis in a VLP formed by the inventive polypeptide. One or more modifications to wtVP2, in some aspects, can include a substitution in loop 3, a deletion in loop 3, a substitution in loop 4, a deletion in loop 4, a substitution upstream of loop 3, a deletion upstream of loop 3, a substitution upstream of loop 4, a deletion upstream of loop 4, or combinations thereof. In some embodiments, the inventive polypeptide does not encompass a naturally occurring polypeptide.

The term "upstream" as used herein, unless otherwise indicated, refers to an amino acid position relative to the referenced amino acid or secondary structure in wtVP2 (e.g., upstream of amino acid 398 or upstream of loop 3); the relative position can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids away from the referenced amino acid or secondary structure. The relative position can be from about 1 to about 35, from about 5 to about 30, from about 10 to about 25, from about 12 to about 20, or from about 14 to about 18 amino acids away from the referenced amino acid or secondary structure. The relative position can be at least about 1, at least about 5, at least about 10, at least about 20, no more than about 20, no more than about 25, no more than about 30, or no more than about 35 amino acids away from the referenced amino acid or secondary structure.

In some embodiments, one or more modifications to wtVP2 can include a substitution or deletion to one or more amino acids exposed (e.g., accessible to interact with other molecules) or partially exposed on the outer surface of the capsid of a wtVLP or a virion such as B19 virion (e.g., at a P antigen binding site). In some embodiments, one or more modifications to wtVP2 can include a substitution or deletion to GLN43, LEU45, ILE46, PRO47, TYR48, ASP49, PRO50, GLU51, HIS52, HIS53, TYR54, LYS55, VAL56, PHE57, PRO59, ALA60, ALA61, SER62, SER63, CYS64, HIS65, ASN66, ALA67, SER68, GLY69, LYS70, GLU71, ALA72, LYS73, VAL74, CYS75, THR76, ILE77, THR78, ILE80, SER84, THR85, PRO86, ASP130, VAL131, THR132, ASP133, LYS134, THR135, GLY136, GLY137, GLY138, VAL139, GLN140, VAL141, THR142, ASP143, ASP168, THR169, LEU170, ALA171, PRO172, GLU173, LEU174, PRO175, ILE176, TRP177, VAL178, TYR179, PHE180, PRO182, GLN183, LEU187, VAL189, GLY190, ASP191, VAL192, ASN193, THR194, GLN195, GLY196, ILE197, SER198, GLY199, ASP200, SER201, LYS202, LYS203, LEU204, SER206, GLU207, GLU208, PHE211, ASN241, GLU243, CYS245, HIS248, TYR250, GLU251, TYR253, PRO255, LEU256, TYR257, GLY258, ARG260, GLY262, VAL263, PRO264, ASP265, THR266, LEU267, GLY268, GLY269, PRO271, PHE273, ARG274, SER275, LEU276, THR277, HIS278, GLU279, ASP280, HIS281, ALA282, ILE283, GLN284, SER298, THR299, LYS300, GLU301, GLY302, ASP303, SER304, SER305, ASN306, THR307, GLY308, ALA309, GLY310, LYS311, ALA312, LEU313, THR314, LEU316, SER321, GLN322, ASN323, THR324, ARG325, ILE326, SER327, HIS338, HIS339, TRP340, ASP341, THR342, ASP343, LYS344, TYR345, VAL346, THR347, ILE349, HIS354, GLY355, GLN356, THR357, THR358, TYR359, GLY360, ASN361, ALA362, GLU363, ASP364, LYS365, GLU366, TYR367, GLN368, GLN369, GLY370, VAL371, PHE374, PRO375, ASN376, GLU377, LYS378, GLU379, LEU381, GLN383, LEU384, GLN385, GLY386, ASN388, MET389, HIS390, TYR392, PHE393, PRO394, ASN395, LYS396, GLY397, THR398, GLN399, GLN400, TYR401, THR402, ASP403, GLN404, ILE405, GLU406, ASN416, ARG417, ALA419, GLU423, LYS459, ILE460, PRO462, SER464, PRO466, ILE467, GLY468, GLY469, ILE470, LYS471, SER472, MET473, GLY474, ILE475, THR476, THR477, LEU478, VAL479, TYR481, ARG502, TRP503, GLN506, PRO507, GLY508, VAL509, TYR510, PRO512, HIS513, ALA514, ALA515, GLY516, HIS517, LEU518, LEU522, TYR523, ASP524, PRO525, THR526, ALA527, THR528, ASP529, ALA530, LYS531, GLN532, HIS533, HIS534, ARG535, GLY537, TYR538, GLU539, LYS540, PRO541, GLU542, GLU543, LEU544, TRP545, THR546, LYS548, SER549, ARG550, VAL551, HIS552, PRO553, LEU554, or combination thereof.

In some embodiments, one or more modifications can occur at a wtVP2 (e.g., a B19 wtVP2) binding site or a virion (e.g., B19 virion) binding site, such as a P antigen binding site. In some instances, one or more modifications to wtVP2 can include a substitution at Y401, a deletion at Y401, a substitution at Q399, a deletion at Q399, a substitution at Q400, a deletion at Q400, a substitution at Q404, a deletion at Q404, a substitution at Q368, a deletion at Q368, a substitution at Q369, a deletion at Q369, a substitution at Y392, a deletion at Y392, or combinations thereof. In yet other embodiments, one or more modifications to wtVP2 can include Y401F, Y401W, Y401A, Q368A, Q369A, Q368N, Q369N, Q399N, Q400N, Q404T, Y392A, Y392F, Q404N, Y401P, T402A, D403A, Q404A, or combinations thereof. In still other embodiments, the inventive polypeptide is construct A, construct B, construct C, construct D, construct E, construct F, construct G, construct H, construct I, construct J, construct K, construct L, construct M, construct N, construct O, construct P, construct Q, construct R, construct S, construct T, construct U, construct V, construct W, or construct X (see Table 1).

In some embodiments, the inventive polypeptide can have a polypeptide sequence with an amino acid sequence identity to wtVP2 of about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 90%, at least about 95%, at least about 99%, or at least about 99.5%. In some embodiments, the inventive polypeptide sequence has an amino acid sequence identity to SEQ ID NO: 1 of about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 90%, at least about 95%, at least about 99%, or at least about 99.5%. The amino acid sequence identity (e.g., percent identity) can be determined by any suitable method, such as using BLAST, BLAST-2, ALIGN, ALIGN-2, or Megalign software. Unless otherwise indicated, the amino acid sequence identity (e.g., percent identity) is determined using BLAST-2.

In some embodiments, mVLP made from the inventive polypeptide has a reduced binding capacity to P antigen relative to wtVLP. In other embodiments, the mVLP made from the inventive polypeptide has no measurable binding to P antigen.

Some embodiments of the invention include nucleic acid molecules that can encode for the inventive polypeptide. In certain embodiments, the nucleic acid molecule is included in a vector or a plasmid. In certain embodiments, the nucleic acid molecule is in a cell, such as an insect (e.g., Sf9) or mammalian cell (e.g., CHO or HEK).

In some embodiments, the nucleic acid molecule sequence has a sequence identity to wtVP2 of about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 90%, at least about 95%, at least about 99%, or at least about 99.5%. In some embodiments, the nucleic acid molecule sequence has a sequence identity to SEQ ID NO: 2 of about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 90%, at least about 95%, at least about 99%, or at least about 99.5%. The nucleic acid sequence identity (e.g., percent identity) can be determined by any suitable method, such as using BLAST, BLAST-2, ALIGN, ALIGN-2, or Megalign software. Unless otherwise indicated, the nucleic acid sequence identity (e.g., percent identity) is determined using BLAST-2.

In some embodiments, the nucleic acid molecule encodes for an inventive polypeptide that has one or more modifications to wtVP2 which can be in or near (e.g., near can be a distance of about 5 Å, about 10 Å, about 15 Å, about 20 Å, about 25 Å, about 30 Å, about 35 Å, about 40 Å, about 45 Å, about 50 Å, less than about 50 Å or less than about 30 Å) the recess of the three-fold axis in a VLP formed by the inventive polypeptide. The nucleic acid molecule encodes for an inventive polypeptide that has one or more modifications to wtVP2, in some aspects, which can include a substitution in loop 3, a deletion in loop 3, a substitution in loop 4, a deletion in loop 4, a substitution upstream of loop 3, a deletion upstream of loop 3, a substitution upstream of loop 4, a deletion upstream of loop 4, or combinations thereof. In some instances, the nucleic acid molecule encodes for an inventive polypeptide that has one or more modifications to wtVP2 that can include a substitution at Y401, a deletion at Y401, a substitution at Q399, a deletion at Q399, a substitution at Q400, a deletion at Q400, a substitution at Q404, a deletion at Q404, a substitution at Q368, a deletion at Q368, a substitution at Q369, a deletion at Q369, a substitution at Y392, a deletion at Y392, or combinations thereof. In yet other embodiments, the nucleic acid molecule encodes for an inventive polypeptide that has one or more modifications to wtVP2 which can include Y401F, Y401W, Y401A, Q368A, Q369A, Q368N, Q369N, Q399N, Q400N, Q404T, Y392A, Y392F, Q404N, Y401P, T402A, D403A, Q404A, or combinations thereof. In still other embodiments, the nucleic acid molecule encodes for an inventive polypeptide that is construct A, construct B, construct C, construct D, construct E, construct F, construct G, construct H, construct I, construct J, construct K, construct L, construct M, construct N, construct O, construct P, construct Q, construct R, construct S, construct T, construct U, construct V, construct W, or construct X (see Table 1).

As modifications or changes may be made in the structure of the nucleic acid molecules and/or polypeptides of the present invention, while obtaining molecules having similar or improved characteristics, such biologically functional equivalents are also encompassed within some embodiments of the present invention. In certain instances, the biological functional equivalent may comprise a nucleic acid that has been engineered to contain distinct sequences while at the same time retaining the capacity to encode the desired inventive polypeptide. This can be accomplished owing to the degeneracy of the genetic code (i.e., the presence of multiple codons) which encode for the same amino acids. In one example, one of ordinary skill in the art may wish to introduce a restriction enzyme recognition sequence into a nucleic acid sequence while not disturbing the ability of that polynucleotide to encode a protein.

In another example, a nucleic acid molecule can be engineered to contain certain sequences that result in (and encode) a biological functional equivalent with more significant changes. In some embodiments, certain amino acids may be substituted for other amino acids in a protein structure without appreciable loss of desired function such as, for example, inter-molecular interaction among mutated VP2 proteins, mVLP formation, reduction in P-antigen binding by the mVLP, reduction of hemagglutination by the mVLP, neutralizing epitopes in the mVLP, or induction of antibodies by neutralizing epitopes in the mVLP. So-called "conservative" changes do not disrupt the desired biological activity of the protein, as the structural change is not one that impinges on the protein's ability to carry out its desired functions. Some embodiments of the present invention encompass various changes that may be made in the sequence of nucleic acid molecules and in the sequence of polypeptides disclosed herein.

In terms of functional equivalents, it is well understood by the skilled artisan that, inherent in the definition of a "biologically functional equivalent" polypeptide or polynucleotide, is the concept that there is a limit to the number of changes that may be made within a defined portion of the molecule while retaining a molecule with an acceptable level of desired biological activity, such as, for example, inter-molecular interaction among mutated VP2 proteins, mVLP formation, reduction in P-antigen binding by the mVLP, reduction of hemagglutination by the mVLP, neutralizing epitopes in the mVLP, or induction of antibodies by neutralizing epitopes in the mVLP. Biologically functional equivalents are thus defined herein as those polypeptides (and nucleic acid molecules) in which selected amino acids (or codons) may be substituted.

In general, the shorter the length of the molecule, the fewer the changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, or the like. An analysis of the size, shape or type of the amino acid side-chain substituents reveals that arginine, lysine or histidine are all positively charged residues; that alanine, glycine or serine are all of similar size; or that phenylalanine, tryptophan or tyrosine all have a generally similar shape. Therefore, based upon these considerations, arginine, lysine or histidine; alanine, glycine or serine; or phenylalanine, tryptophan or tyrosine; are defined herein as biologically functional equivalents. Although not grouped here, other amino acids may provide functionally equivalent polypeptides.

The hydropathic index of amino acids may also be considered. Each amino acid has been assigned a hydropathic index on the basis of their hydrophobicity or charge characteristics, these are: isoleucine (+4.5); valine (+4.2); Leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); or arginine (−4.5). Hydropathic amino acid index can be used to confer interactive biological function on a protein. In some instances, certain amino acids may be substituted for other amino acids having a similar hydropathic index or score or still retain a similar biological activity. In making changes based upon the hydropathic index, the substitution of amino acids with hydropathic indices can be within ±2 or within ±1, or within ±0.5.

The substitution of like amino acids can also be made on the basis of hydrophilicity, particularly where the biological functional equivalent polypeptide or peptide thereby created is intended for use in immunological embodiments, as in certain embodiments of the present invention. U.S. Pat. No. 4,554,101 states that the greatest local average hydrophilicity of a polypeptide, as governed by the hydrophilicity of its adjacent amino acids, can correlate with its immunogenicity or antigenicity (i.e., with a biological property of the polypeptide).

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids with hydrophilicity values can be within ±2, or within ±1, or within ±0.5.

Conservatively substituted sequence indicates that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions include, for example, substitutions of entire regions having similar hydrophobicity characteristics.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like.

of the coding region or may include various internal sequences, (i.e., introns) which are known to occur within genes.

The present invention, in some aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified or unusual amino acids. A table of exemplary, but not limiting, modified or unusual amino acids is provided in Table C.

TABLES A and B

Amino acid designations and codon table

| Table A - Amino Acid Designations | | | Table B - Codons for Amino Acids |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The term "functionally equivalent codon" is used herein to refer to codons that encode the same amino acid, such as the six codons for arginine or serine, and also refers to codons that encode biologically equivalent amino acids (see Codon Table, above).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological activity where polypeptide expression is concerned. The addition of terminal sequences particularly applies to nucleic acid sequences that may, for example, include various non-coding sequences flanking either of the 5' or 3' portions

TABLE C

Modified or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |

TABLE C-continued

Modified or Unusual Amino Acids

| Abbr. | Amino Acid | Abbr. | Amino Acid |
|---|---|---|---|
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

The presently-disclosed subject matter further includes a method of producing a polypeptide (or VLP, including a polypeptide that self-assembles into a VLP) comprising a VP2 polypeptide mutant. Eukaryotic expression systems include plant-based systems; insect cell systems via recombinant baculoviruses; whole insect systems via recombinant baculoviruses; genetically engineered yeast systems, including but not limited to *Saccharomyces* sp. and *Picchia* spp.; and mammalian cell systems, including but not limited to Chinese hamster ovary cells or other cell lines commonly used for industrial scale expression of recombinant proteins. In some embodiments, useful plant-based expression systems can include transgenic plant systems. In some embodiments, useful plant-based expression systems can include transplastomic plant systems.

In some embodiments, a method of producing the inventive polypeptide (which can self-assemble into a VLP) includes providing a host cell comprising a polynucleotide, as disclosed herein, operatively linked to a promoter operable under conditions whereby the encoded polypeptide is expressed; and recovering the polypeptide from the host cell.

One or more VP2 polypeptide mutants can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more VP2 polypeptide mutants can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%. Some embodiments of the present invention include compositions comprising one or more VP2 polypeptide mutants. In certain embodiments, the composition is a pharmaceutical composition (e.g., a vaccine), such as compositions that are suitable for administration to animals (e.g., mammals, primates, monkeys, humans, canine, porcine, mice, rabbits, or rats).

Virus Like Particles and Compositions Including Pharmaceutical Compositions

In some embodiments of the invention, the inventive polypeptide can form a virus-like particle. As defined herein, unless otherwise indicated, "VLP" is a virus-like particle. A VLP is a small particle that comprises one or more polypeptides from the outer coat (e.g., capsid) of a virus. VLPs do not contain any genetic material from the virus and thus cannot cause an infection. In some instances, VLPs can be used to make vaccines. The expression of some viral structural proteins (e.g., envelope or capsid proteins) can result in the self-assembly of VLPs. As defined herein, unless otherwise indicated, "wtVLP" (also referred to as "wild type VLP") is a VLP made only from VP2 proteins (i.e., with no modifications to the VP2 amino acid sequence); wtVLPs do not include any other proteins other than VP2 (i.e., VP1 is not included). As defined herein, unless otherwise indicated, "mVLP" (also referred to as "mutant VLP") is a virus-like particle formed from inventive polypeptides, where the inventive polypeptide has at least one amino acid modification relative to wild type VP2. In certain embodiments, the mVLP can be morphologically similar to wtVLP (e.g., as determined using electron microscopy). In some embodiments, the mVLP can have reduced binding to P antigen compared to wtVLP (e.g., as measured using a hemagglutination assay). In some embodiments, the mVLP can have no detectable binding to P antigen (e.g., as measured using a hemagglutination assay). In other embodiments, the mVLP has reduced hemagglutination of red blood cells compared to wtVLP (e.g., as measured using a hemagglutination assay). In still other embodiments, the mVLP has no detectable hemagglutination (e.g., as measured using a hemagglutination assay). In certain embodiments, the mVLP can have one or more neutralizing epitopes (e.g., conformational epitopes) which can be determined by any suitable method (e.g., by using a hemagglutination inhibition assay). In some embodiments, an epitope is a region on the surface of the mVLP (e.g., a conformational change in an mVLP can create or induce the appearance of an epitope) capable of eliciting an immune response; in certain embodiments, a neutralizing epitope is an epitope (e.g., a conformation epitope) that can induce an immune response to an mVLP, a wtVLP, a parvovirus, an erythrovirus, a B19 parvovirus, or combinations thereof. In some embodiments, the epitope is created by a conformational change in one or more mVP2s of the mVLP (e.g., one or more VP2 on the surface of the mVLP) capable of eliciting an immune response; in certain embodiments, a neutralizing epitope is an epitope created by a conformation epitope that can induce an immune response to an mVLP, a wtVLP, a parvovirus, an erythrovirus, a B19 parvovirus, or combinations thereof. In other embodiments, the mVLP can induce the production of antibodies (e.g., a high titer of antibodies) in an animal (e.g., mammals, humans, rats, mice, feline, canine, porcine, monkeys, or primates) where the antibodies are capable of inhibiting hemagglutination by wtVLP (e.g., as determined using a hemagglutination inhibition assay).

In some embodiments, the mVLP can be made from an inventive polypeptide that has one or more modifications to wtVP2 which can be in or near (e.g., near can be a distance of about 5 Å, about 10 Å, about 15 Å, about 20 Å, about 25 Å, about 30 Å, about 35 Å, about 40 Å, about 45 Å, about 50 Å, less than about 50 Å or less than about 30 Å) the recess of the three-fold axis in a VLP formed by the inventive polypeptide. The mVLP can be made from an inventive polypeptide that has one or more modifications to wtVP2, in some aspects, which can include a substitution in loop 3, a deletion in loop 3, a substitution in loop 4, a deletion in loop 4, a substitution upstream of loop 3, a deletion upstream of loop 3, a substitution upstream of loop 4, a deletion upstream of loop 4, or combinations thereof. In some instances, the mVLP can be made from an inventive polypeptide that has one or more modifications to wtVP2 that can include a substitution at Y401, a deletion at Y401, a substitution at Q399, a deletion at Q399, a substitution at Q400, a deletion at Q400, a substitution at Q404, a deletion at Q404, a substitution at Q368, a deletion at Q368, a substitution at Q369, a deletion at Q369, a substitution at Y392, a deletion at Y392, or combinations thereof. In yet other embodiments, the mVLP can be made from an inventive polypeptide that has one or more modifications to wtVP2 which can include Y401F, Y401W, Y401A, Q368A, Q369A, Q368N, Q369N, Q399N, Q400N, Q404T, Y392A, Y392F, Q404N, Y401P, T402A, D403A, Q404A, or combinations thereof. In still other embodiments, the mVLP can be made from an inventive polypeptide that is construct A, construct B, construct C, construct D, construct E, construct F, construct G, construct H, construct I, construct J, construct K, construct L, construct M, construct N, construct O, construct P, construct Q, construct R, construct S, construct T, construct U, construct V, construct W, or construct X (see Table 1).

One or more mVLPs can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more mVLPs can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more mVLPs. In certain embodiments, the composition is a pharmaceutical composition (e.g., a vaccine), such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any method known in the art, such as measurement of antibody titers.

In some embodiments, one or more mVLPs can be part of a pharmaceutical composition (e.g., a vaccine) and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more mVLPs) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an organism, which can involve treatment with an amount of at least one mVLP that is effective to treat the disease, condition, or disorder that the organism has, or is suspected of having, or is susceptible to, or to bring about a desired physiological effect. In some embodiments, the composition or pharmaceutical composition (e.g., a vaccine) comprises at least one mVLP which can be administered to an animal (e.g., mammals, primates, monkeys, or humans) in an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention can be administered in combination with one or more other therapeutic agents for a given disease, condition, or disorder.

In some embodiments, the compositions can include a unit dose of one or more mVLPs in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

In certain embodiments, compositions (e.g., pharmaceutical compositions or vaccines) can include one or more adjuvants. In some embodiments, adjuvants are not included in the composition. In still other embodiments, the composition comprises one or more adjuvants, such as, but not limited to polymers of acrylic or methacrylic acid, maleic anhydride and alkenyl derivative polymers; immunostimulating sequences (ISS), an oil in water emulsion (e.g., the SPT emulsion described on p 147 of "Vaccine Design, The Subunit and Adjuvant Approach" published by M. Powell, M. Newman, Plenum Press 1995, and the emulsion MF59 described on p 183 of the same reference), cation lipids containing a quaternary ammonium salt, $AlK(SO_4)_2$, $AlNa(SO_4)_2$, $AlNH(SO_4)_4$, silica, alum, $Al(OH)_3$, $Ca_3(PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyl-L-alanyl-D-isoglutaminyl-L-alanine-2-(1'2'-dipalmitoyl-s-n-glycero-3-hydroxphosphoryloxy)-ethylamine (CGP 19835A, also referred to as MTP-PE), RIBI (MPL+TDM+CWS) in a 2% squalene/Tween-80.RTM. emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum, Bordetella pertussis*, and members of the genus *Brucella*, liposomes or other lipid emulsions, ISCOMS, Quil A, ALUN, Lipid A derivatives, choleratoxin derivatives, HSP derivatives, LPS derivatives, synthetic peptide matrixes or GMDP, cytokines, Interleukin 1, Interleukin 2, Montanide ISA-51, QS-21, TITERMAX®, or ADJUPLEX™ Vaccine Adjuvant.

In some embodiments, additional adjuvants or compounds that can be used (e.g., to modify or stimulate the immune response) include ligands for Toll-like receptors (TLRs). In mammals, TLRs are a family of receptors expressed on DCs that recognize and respond to molecular patterns associated with microbial pathogens. Several TLR ligands have been intensively investigated as vaccine adjuvants. Bacterial lipopolysaccharide (LPS) is the TLR4 ligand and its detoxified variant mono-phosphoryl lipid A (MPL) is an approved adjuvant for use in humans. TLR5 is expressed on monocytes and DCs and responds to flagellin whereas TLR9 recognizes bacterial DNA containing CpG motifs. Oligonucleotides (OLGs) containing CpG motifs are potent ligands for, and agonists of, TLR9 and have been intensively investigated for their adjuvant properties. In some embodiments, the adjuvant is alum. In some embodiments the adjuvant is not M59 adjuvant.

In certain embodiments, administration of the compositions (e.g., pharmaceutical compositions or vaccines) induces an immune response to prevent or ameliorate the effects of future infection. Depending on the intended mode of administration, the compositions of the present invention can be in various forms of pharmaceutical compositions. Any method of preparation of vaccines and immunizing agents can be used, as exemplified by U.S. Pat. Nos. 4,608,251; 4,601,903; 4,599,231; 4,599,230; 4,596,792; and 4,578,770. Typically, such vaccines are prepared as injectables either as liquid solutions or suspensions; solid forms suitable for solution in, or suspension in, liquid prior to injection may also be prepared. The preparation may also be emulsified. In addition, if desired, the vaccine may contain minor amounts of auxiliary substances such as wetting or emulsifying agents, pH buffering agents, or adjuvants that enhance the effectiveness of the vaccines.

Parenteral administration, if used, is generally characterized by injection. Sterile injectables can be prepared in conventional forms, either as liquid solutions or suspensions, solid forms suitable for solution or suspension in liquid prior to injection, or as emulsions.

Administration Routes and Treatments of Disease

The mVLPs of the invention can be administered to animals by any number of suitable administration routes or formulations. The mVLPs of the invention can also be used to treat animals for a variety of diseases. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects. A subject susceptible to a parvovirus infection, an erythrovirus infection, or a B19 parvovirus (e.g., human) infection can be a human or an animal subject.

The route of administration of the mVLPs of the invention can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the mVLP identity (e.g., the physical and chemical properties of the mVLP) as well as the age and weight of the animal, the particular disease, and the severity of the disease. Of course, combinations of administration routes can be administered, as desired.

Some embodiments of the invention include a method for providing a subject with a composition comprising an mVLP described herein (e.g., a pharmaceutical composition) which comprises one or more administrations of one or more such compositions; the compositions may be the same or different if there is more than one administration.

Diseases that can be treated in an animal (e.g., mammals, porcine, canine, avian (e.g., chicken), bovine, feline, primates, monkeys, rabbits, and humans) using the mVLPs include, but are not limited to parvovirus infections, diseases related to parvovirus infections, erythrovirus infections, diseases related to erythrovirus infections, parvovirus B19 infections, and diseases related to parvovirus B19 infection. Some diseases related to parvovirus infections (e.g., erythrovirus infections or parvovirus B19 infections) include, but are not limited to, hydrops fetalis intrauterine fetal death, erythema infectiosum (i.e., fifth disease), hereditary diseases (e.g., sickle cell anemia or Thalassemia), acquired diseases (e.g., anemia or anemia induced by malaria), parvovirus B19-induced red cell aplasia (TRCA), chronic anemia, diseases related to immunodeficient individuals (e.g., recipients of organ transplants, animals undergoing chemotherapy, animals undergoing bone marrow transplant, or HIV-positive animals), acute arthropathy, persistent arthropathy, aplastic crisis, arthritis, hepatitis, myocarditis, hepatosplenomegaly, acute thyroiditis, subacute thyroiditis, Graves' disease, Hashimoto's thyroiditis, and autoimmune diseases (e.g., autoimmune thyroid diseases, systemic lupus erythematosus (SLE), meningiencephalitis, or fibromyalgia).

Other diseases related to parvovirus infections (e.g., erythrovirus infections or parvovirus B19 infections) include, but are not limited to, gastrointestinal tract damage, dehydration, cardiac syndrome, lethargy, diarrhea (e.g., severe diarrhea), fever, vomiting, loss of appetite, stillbirth, mummification, embryonic death, infertility, low white blood cell count, cerebellar hypoplasia, lymphadenopathy, splenomegaly, glomerulonephritis, and anemia. Animals that can be treated include but are not limited to mammals, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. A subject susceptible to a parvovirus infection, an erthrovirus infection, or a B19 parvovirus (e.g., human) infection can be a human or animal subject. In some instances, the animal is in need of the treatment (e.g., a prophylactic treatment).

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment (e.g., vaccination) and therapeutic treatment. Any of the compositions (e.g., pharmaceutical compositions or vaccines) described herein can be used to treat an animal.

As related to treating a parvovirus infection (e.g., an erythrovirus infection or a parvovirus B19 infection), treating can include but is not limited to prophylactic treatment and therapeutic treatment. As such, treatment can include, but is not limited to: conferring protection against a parvovirus infection (e.g., an erythrovirus infection or a parvovirus B19 infection); preventing a parvovirus infection (e.g., an erythrovirus infection or a parvovirus B19 infection); reducing the risk of parvovirus infection (e.g., an erythrovirus infection or a parvovirus B19 infection); ameliorating or relieving symptoms of a parvovirus infection (e.g., an erythrovirus infection or a parvovirus B19 infection); eliciting an immune response against a parvovirus (e.g., an erythrovirus or a parvovirus B19) or an antigenic component thereof; inhibiting the development or progression of a parvovirus infection (an erythrovirus infection or a parvovirus B19 infection); inhibiting or preventing the onset of symptoms associated with a parvovirus infection (e.g., an erythrovirus infection or a parvovirus B19 infection); reducing the severity of a parvovirus infection (e.g., an erythrovirus infection or a parvovirus B19 infection); and causing a regression of a parvovirus infection (e.g., an erythrovirus infection or a parvovirus B19 infection) or one or more of the symptoms associated with a parvovirus infection (e.g., an erythrovirus infection or a parvovirus B19 infection). In some embodiments, treating does not include prophylactic treatment (e.g., vaccination or otherwise preventing or ameliorating future disease).

Symptoms associated with parvovirus infection (e.g., an erythrovirus infection or a parvovirus B19 infection) are known to those of ordinary skill in the art and can include those described herein and well-known to those of ordinary skill in the art. The presence of an infection can be assessed using methods known to those or ordinary skill in the art. In some cases, the presence of a parvovirus infection (e.g., an erythrovirus infection or a parvovirus B19 infection) can be determined using methods known to those of ordinary skill in the art.

Treatment of an animal can occur using any suitable administration method (such as those disclosed herein) and using any suitable amount of mVLPs (such as those disclosed herein). In some embodiments, methods of treatment comprise treating an animal for a parvovirus infection (e.g., in a human or primate), a disease related to a parvovirus infection (e.g., in a human or primate), an erythrovirus infection (e.g., in a human or primate), a disease related to an erythrovirus infection (e.g., in a human or primate), a disease related to a parvovirus B19 infection (e.g., in a human or primate), a parvovirus B19 infection (e.g., in a human or primate), or combinations thereof. Some embodiments of the invention include a method for treating a subject (e.g., an animal such as a human or primate) with a composition comprising an mVLP described herein (e.g., a pharmaceutical composition) which comprises one or more administrations of one or more such compositions; the compositions may be the same or different if there is more than one administration.

In some embodiments, the method of treatment includes administering an effective amount of a composition comprising an mVLP. As used herein, the term "effective amount" refers to a dosage or a series of dosages sufficient to affect treatment (e.g., to treat a parvovirus infection such as an erythrovirus infection or a parvovirus B19 infection or to treat diseases related to a parvovirus infection such as diseases related to an erythrovirus infection or diseases related to a parvovirus B19 infection) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one mVLP (which can be administered to an animal such as mammals, primates, monkeys or humans) can be an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg.

As used herein, "immunizing" and "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells))), and increased processing and presentation of antigen by antigen presenting cells. An immune response can be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade and/or activation of complement), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids)). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

In some embodiments, the treatment comprises vaccination. In some aspects, vaccination comprises vaccinating an animal (e.g., mammals, primates, monkeys (e.g., macaque, rhesus macaque, pig tail macaque), humans, canine, feline, bovine, porcine, avian (e.g., chicken), mice, rabbits, and rats) against a parvovirus, an erthyrovirus, parvovirus B19, or combinations thereof. Any suitable administration methods or protocols can be used for vaccinating an animal Some embodiments for vaccination include a method for providing a subject with a composition comprising an mVLP described herein (e.g., a pharmaceutical composition) which comprises one or more administrations of one or more such compositions; the compositions may be the same or different if there is more than one administration. For example, a single dose can be administered to a subject, or alternatively, two or more inoculations can take place with intervals of several weeks to several months. The extent and nature of the immune responses induced in the subject can be assessed using a variety of techniques generally known in the art. For example, sera can be collected from the subject and tested, for example, for parvovirus DNA or RNA in a sera sample, detecting the presence of antibodies to parvovirus or antigenic fragments thereof using, for example, parvovirus VLPs, or monitoring a symptom associated with parvovirus infection. Relevant techniques are well described in the art, e.g., Coligan et al. Current Protocols in Immunology, John Wiley & Sons Inc. (1994), which is incorporated herein by this reference.

The timing of administration of the vaccine and the number of doses required for immunization can be determined from standard vaccine administration protocols. In some instances, a vaccine composition will be administered in two doses. The first dose will be administered at the elected date and a second dose will follow at one month from the first dose. A third dose can be administered if necessary, and desired time intervals for delivery of multiple doses of a particular mVLP can be determined. In other embodiments, the mVLP may be given as a single dose.

In some instances, for each recipient, the total vaccine amount necessary can be deduced from protocols for immunization with other vaccines. In some embodiments, the exact amount of mVLP required can vary from subject to subject, depending on the species, age, weight and general condition of the subject, the particular fusion protein used, its mode of administration, and the like. In other embodiments, dosage will approximate that which is typical for the administration of other vaccines, and may be in the range of from about 1 ng/kg to about 1 mg/kg body weight, from about 10 ng/kg to about 15 mg/kg, or from about 10 ng/kg to about 100 mg/kg.

Up to 85% of the adult population is sero-positive for Parvovirus B19 infection. Parvovirus B19 infection can cause hydrops fetalis and intrauterine fetal death, although it is most widely known to be related to erythema infectiosum (fifth disease) and can be asymptomatic in healthy individuals. Older children and adults with either hereditary (sickle cell anemia) or acquired (anemia induced by malaria) anemia are at risk for developing parvovirus B19-induced red cell aplasia (TRCA) or death. The cause of the chronic anemia in immunodeficient individuals, such as recipients of organ transplants or HIV-positive patients, was contributed to parvovirus B19 infection. In some instances, the pathological manifestations of parvovirus B19 infection can be affected by the patient's immunologic and hematologic status, and can induce more severe disease, such as acute or persistent arthropathy, aplastic crisis, and also been implicated in arthritis, hepatitis, myocarditis, hepatosplenomegaly, a spectrum of autoimmune diseases such as systemic lupus erythematosus (SLE), meningiencephalitis, or fibromyalgia.

In some embodiments, children (i.e., ages from about 0 to about 18) can be vaccinated before they enter elementary school (i.e., ages from about 0 to about 13). In other embodiments, immunization can be administered to animals at risk. Animal at risk include but are not limited to animals that have had a transfusion, an organ transplant, animals with infectious disease (e.g., HIV or malaria), pregnant animals (e.g., human women) with children (e.g., under the age of 18), animals infected by parvovirus B19 infection, animals (e.g., children) living in an area where malaria is prevalent, immunodeficient animals (e.g., recipients of organ transplants, animals undergoing chemotherapy, animals undergoing bone marrow transplant, or HIV-positive animals), or animals with an autoimmune disease (e.g., systemic lupus erythematosus; SLE, meningiencephalitis and fibromyalgia).

In some embodiments, the treatments disclosed herein can include use of other drugs (e.g., antibiotics) or therapies for treating disease. For example, antibiotics can be used to treat infections and can be combined with a mVLP to treat disease (e.g., infections). In other embodiments, intravenous immunoglobulin (IVIG) therapy can be used as part of the treatment regime (i.e., in addition to administration of mVLPs) of parvovirus infection (e.g., erythrovirus infection or parvovirus B19 infection).

The presently-disclosed subject matter is further illustrated by the following specific but non-limiting examples. The following examples may include compilations of data that are representative of data gathered at various times during the course of development and experimentation related to the present invention.

Examples

Introduction and Design and Generation of B19 VP2 Mutants

Figure 1:
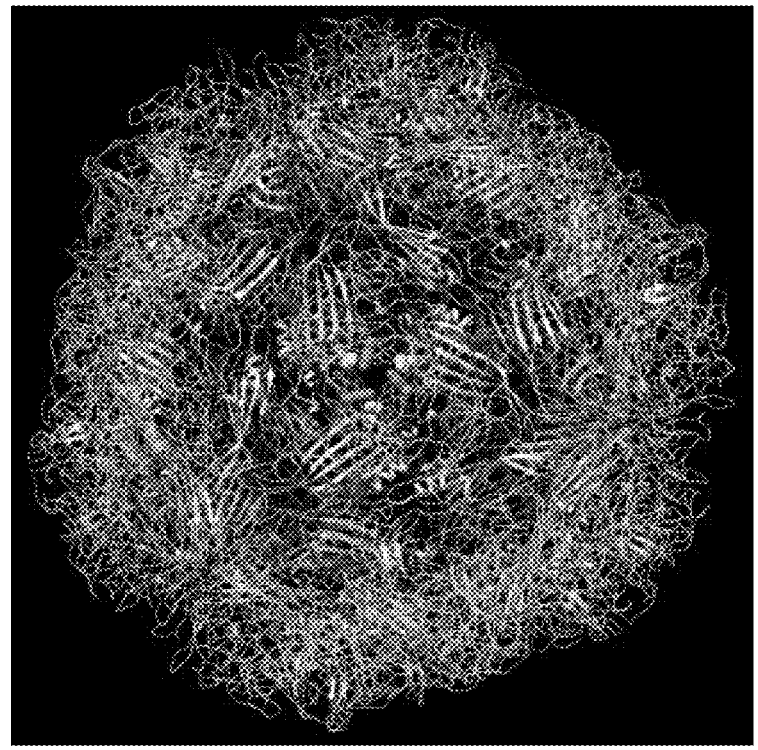
FIG. 1: An example of the predicted effect of mutations on the P antigen binding pocket located at the recess of the three-fold axis. (A) Using the X-ray crystal structure of FIG. 3: Hemagglutination assays using Type O human red blood cells. Hemagglutination assays (HA) were performed to determine binding capacity to P antigen. C−: Control negative for HA, ADPBS [albumin-dextrose PBS] was added instead of wtVP2 or mVLP. C+: Control positive for HA, wtVLP was added.
Figure 1:
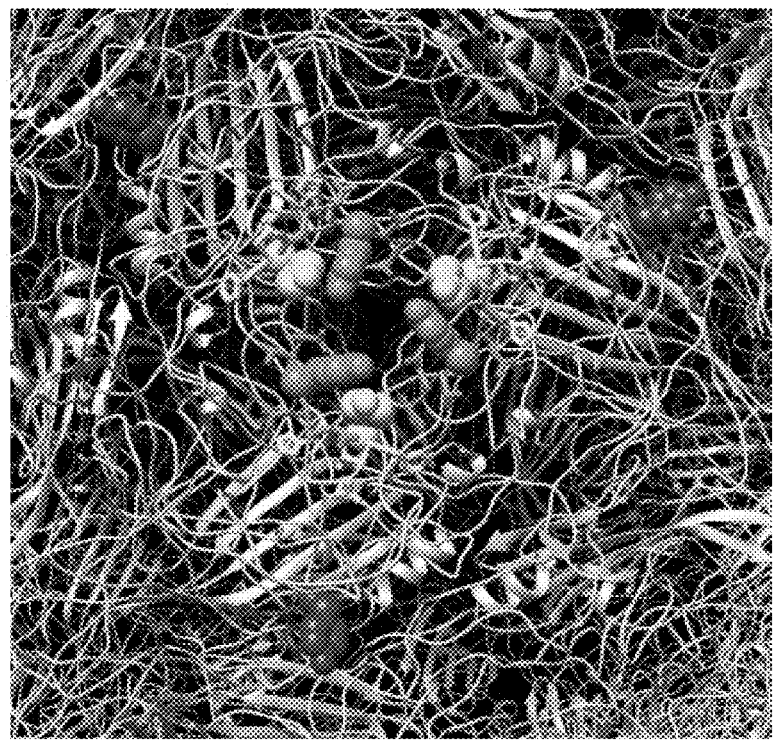
Figure 1:
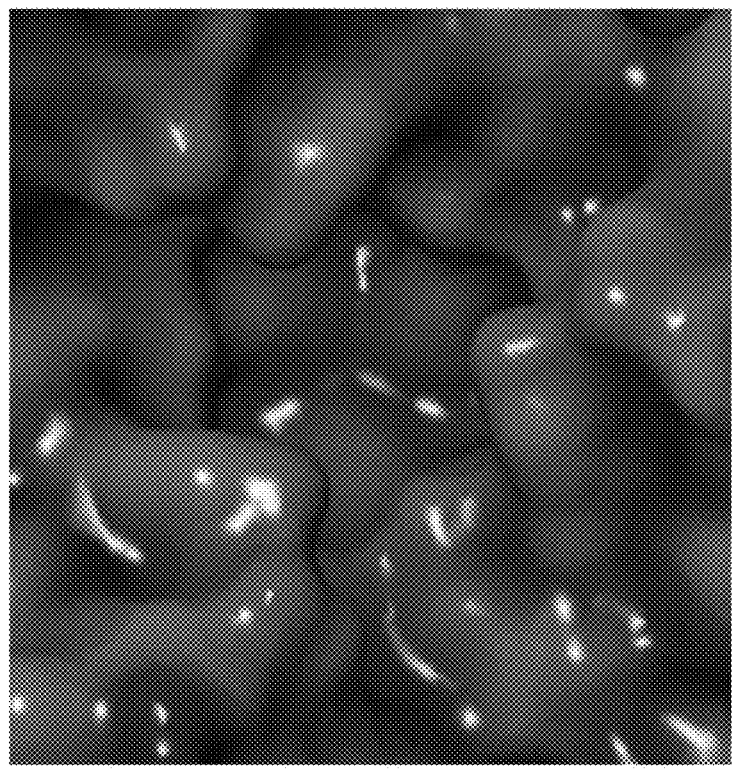
Figure 1:
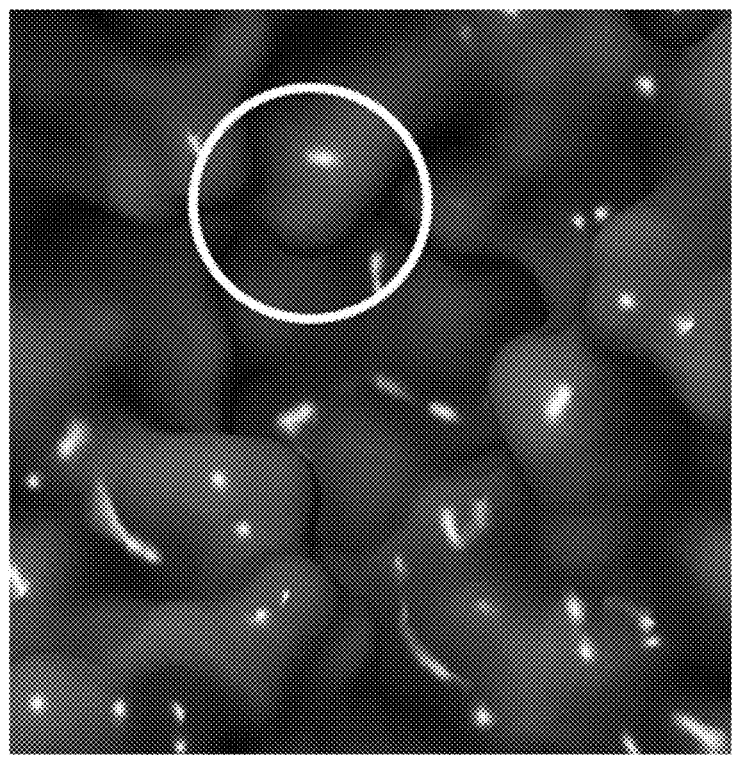
Figure 2:
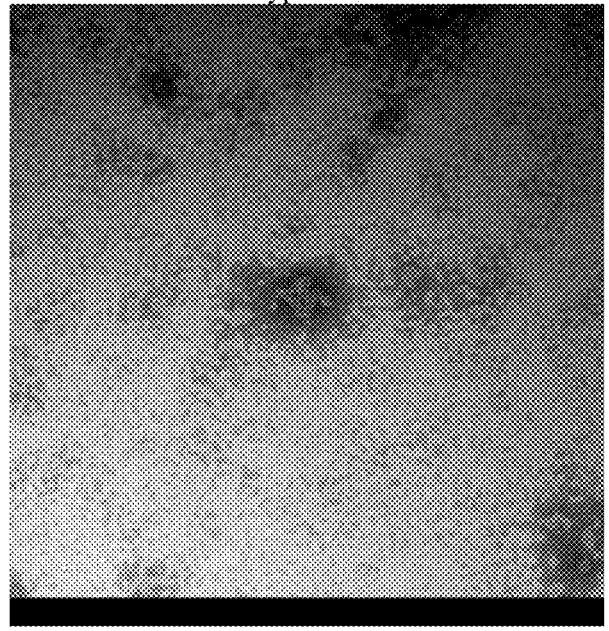
Figure 2:
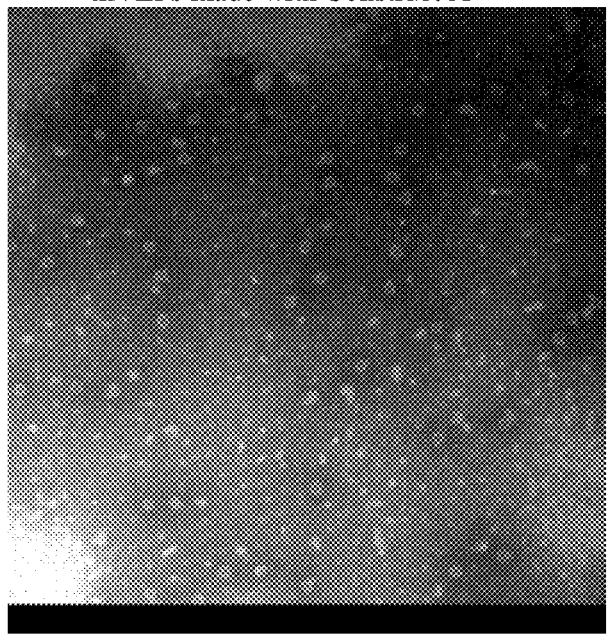
Figure 2:
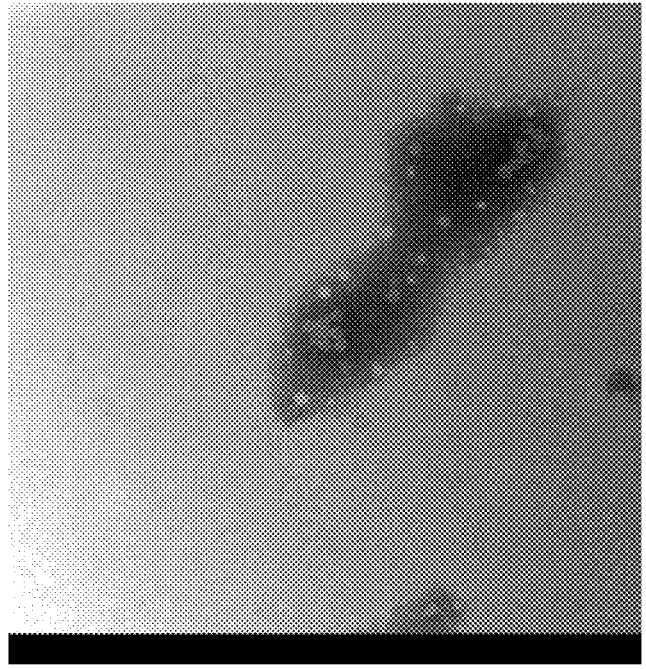
Figure 2:
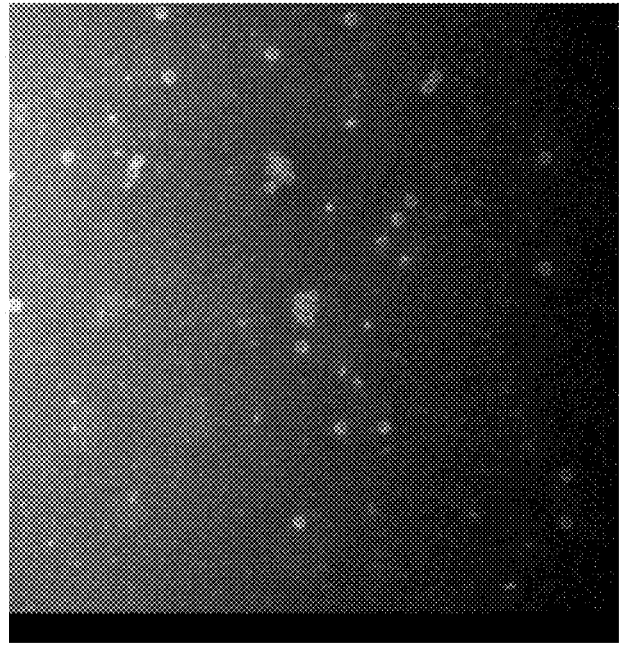
Figure 2:
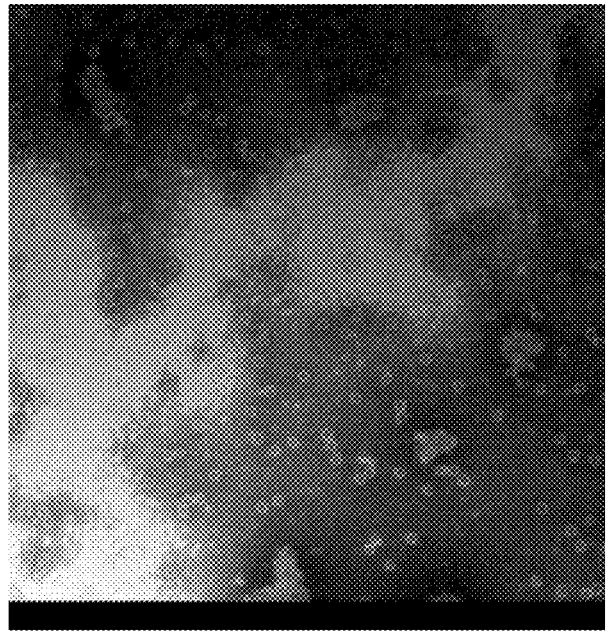
Figure 2:
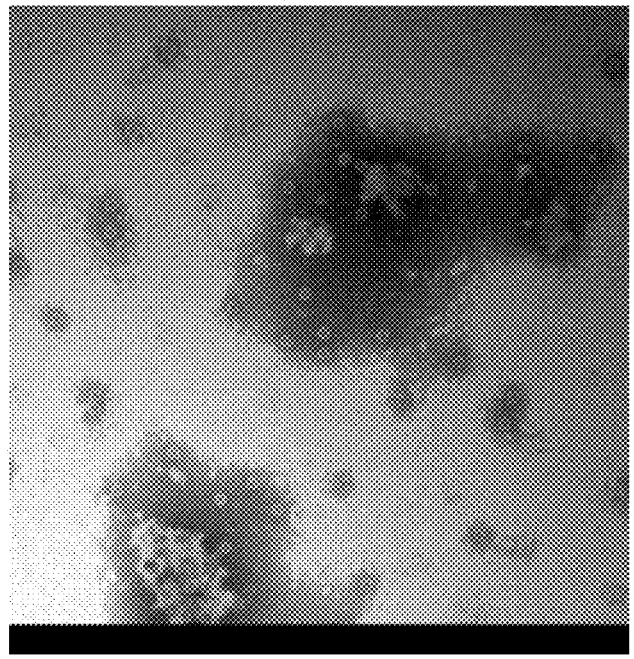
Figure 2:
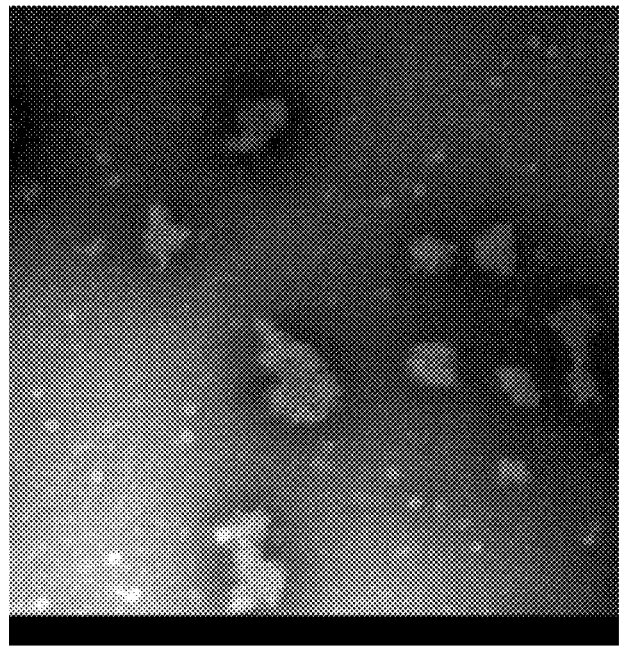
Figure 2:
Figure 2:
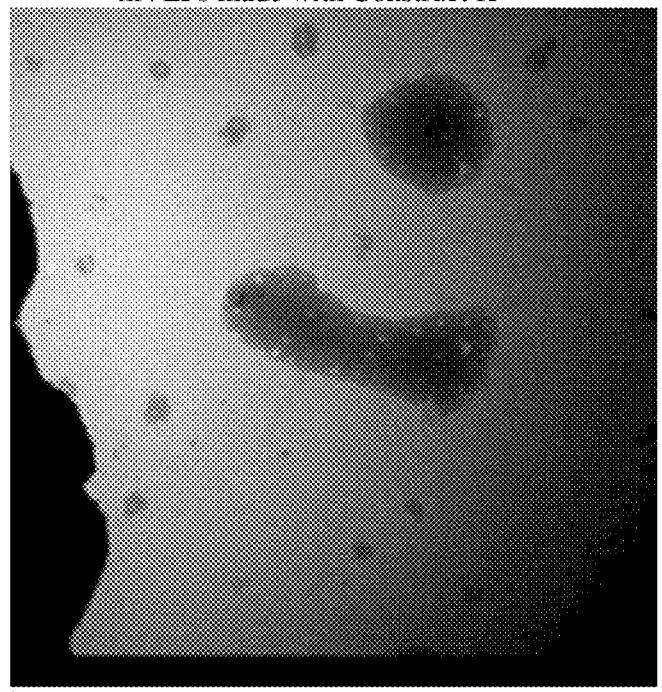

We mutated the P-antigen binding site on VP2, generated mVLPs, and tested their immunities in mice (in some instances, mice are known to be no to low responder to wtVLPs) (Rosenfeld et al., "Unique region of the minor capsid protein of human parvovirus B19 is exposed on the virion surface" J Clin Invest. (1992) Vol. 89, No. 6, pp. 2023-2029; Bansal et al., "Candidate recombinant vaccine for human B19 parvovirus" J Infect Dis. (1993) Vol. 167, No. 5, pp 1034-1044). In certain mutants, amino acids (e.g., amino acids in $H_{390}TYFPN_{395}$, $Q_{399}QYTDQ_{404}$, or $K_{365}EYQQ_{369}$) located at or in the vicinity of loop 4 ($Q_{383}LQGLNMHTYFPNKGTQQYTDQ_{404}$) were replaced with other amino acids that had the similar characteristics (e.g., size, backbone structure, hydrophobicity, and/or charge) to that of the amino acids replaced. Two mutated VP2 ($N_{399}NFTDT_{404}$ and $N_{399}NYTDT_{404}$) formed mVLPs, showed altered agglutination of human RBCs, and were immunogenic in mice. Without being bound by theory, a single mutation can have a potentially greater impact on the P antigen binding if the mutation occurs on or near the three-fold axis, because it can theoretically, in some instances, effectively triple the change at the viral ligand (P-antigen) binding site (e.g., FIGS. 1A and 1B). An example of the predicted 3-D structures of potential wild type and mutant VLPs are shown in FIG. 1C (wild type: $QQT_{401}YDQ$) and FIG. 1D (Constrict A: $QQF_{401}TDQ$).

Each mutated VP2 gene was generated by double PCR method. For this, N-terminus and C-terminus DNA fragments were generated separately using two sets of primers, and full length VP2 gene was generated by annealing these two fragments and performing another PCR using primers annealing 5' and 3' end of VP2 ORF. Full length PCR products were cloned into pFAST Bac1 from which recombinant baculovirus (rBac) was generated. VP2 was then expressed in Sf9 insect cells using rBac.

Cloning and Expression of Mutated B19 VP2 Genes

The targeted mutations were created by double PCRs on baculovirus codon-optimized VP1 minigene (Integrated Technologies, Iowa) of genotype 1 (NCBI reference sequence NC_000883.2) as template. Full-length VP2 gene fragments, that were amplified with Platinum Taq DNA polymerase High Fidelity (Life Technologies, CA), were gel-purified (QIAquick gel extraction kit; Qiagen, CA), cloned into pCR-XL-Topo (Life Technologies, CA) plasmid, fully sequenced, and subcloned into pFASTBac1, from which recombinant bacimids and consecutively baculoviruses were generated according to the procedure provided by the manufacturer of the kit (Bac-to-Bac Baculovirus Expression System; Life Technologies, CA). The expression of mVP2 in Sf9 insect cells was first checked by immunofluorescence (IF) and immunoblot (IB) (Ghim et al. Virology (1992) vol. 190, No. 1, pp. 548-552). Recombinant *E. coli*, generated for the clonings of mVP2 genes, and innocula for recombinant baculoviruses having correct VP2 proteins, were frozen for future studies.

The B19 VP2 polypeptide mutants were constructed with one or more amino acid insertion or point mutations at $H_{390}TYFPN_{395}$ and $Q_{399}QYTDQ_{404}$ in loop 4 and at $K_{365}EYQQ_{369}$ upstream of loop 4, as indicated in Table 1.

TABLE 1

B19 VP2 Polypeptide Wild Type and Mutants

| Construct designation: | Mutation | Amino acid(s) mutated | Nucleic acid sequences used to construct | Primers used |
|---|---|---|---|---|
| B19 Wild Type | none | none | SEQ ID NO: 2 | SEQ ID NO: 27 & SEQ ID NO: 28 |
| A | QQYTDQ to QQFTDQ | Y401F | SEQ ID NO: 3 | SEQ ID NO: 29 & SEQ ID NO: 30 |
| B | QQYTDQ to QQWTDQ | Y401W | SEQ ID NO: 4 | SEQ ID NO: 31 & SEQ ID NO: 32 |
| C | QQYTDQ to QQATDQ | Y401A | SEQ ID NO: 5 | SEQ ID NO: 33 & SEQ ID NO: 34 |
| D | KEYQQ to KEYAA | Q368A and Q369A | SEQ ID NO: 6 | SEQ ID NO: 35 & SEQ ID NO: 36 |
| E | KEYQQ to KEYNN | Q368N to Q369N | SEQ ID NO: 7 | SEQ ID NO: 37 & SEQ ID NO: 38 |
| F | QQYTDQ to NNFTDT | Q399N, Q400N, Y401F, and Q404T | SEQ ID NO: 8 | SEQ ID NO: 39 & SEQ ID NO: 40 |
| G | QQYTDQ to NNYTDT | Q399N, Q400N, and Q404T | SEQ ID NO: 9 | SEQ ID NO: 41 & SEQ ID NO: 42 |
| H | HTYFPN to HTAFPN | Y392A | SEQ ID NO: 10 | SEQ ID NO: 43 & SEQ ID NO: 44 |
| I | HTYFPN to HTFFPN | Y392F | SEQ ID NO: 11 | SEQ ID NO: 45 & SEQ ID NO: 46 |
| J | QQYTDQ to NNFTDN | Q399N, Q400N, Y401F, and Q404N | SEQ ID NO: 12 | SEQ ID NO: 47 & SEQ ID NO: 48 |
| K | QQYTDQ to NNYTDN | Q399N, Q400N, and Q404N | SEQ ID NO: 13 | SEQ ID NO: 49 & SEQ ID NO: 50 |
| L | Adding “DPIG” after QQYTDQ | [insertion] | SEQ ID NO: 14 | SEQ ID NO: 51 & SEQ ID NO: 52 |
| M | QQYTDQ to AAYTDQ | Q399A and Q400A | SEQ ID NO: 15 | SEQ ID NO: 53 & SEQ ID NO: 54 |
| N | QQYTDQ to QQPAAA | Y401P, T402A, D403A, and D404A | SEQ ID NO: 16 | SEQ ID NO: 55 & SEQ ID NO: 56 |
| O | QQYTDQ to NNWTDT | Q399N, Q400N, Y401W and Q404T | SEQ ID NO: 17 | SEQ ID NO: 57 & SEQ ID NO: 58 |
| P | (QQYTDQ) to NNWTDT) + (HTYFPN to NTAFPN) | See Construct O and Construct H | SEQ ID NO: 18 | SEQ ID NO: 59 & SEQ ID NO: 56 |
| Q | (QQYTDQ to QQFTDQ) + (KEYQQ to KEYAA) | See Construct A and Construct D | SEQ ID NO: 19 | SEQ ID NO: 61 & SEQ ID NO: 62 |
| R | (QQYTDQ to NNFTDT) + (KEYQQ to KEYAA) | See Construct F and Construct D | SEQ ID NO: 20 | SEQ ID NO: 63 & SEQ ID NO: 64 |
| S | (QQYTDQ to QQWTDQ) + (HTYFPN to HTAFPN) | See Construct B and Construct H | SEQ ID NO: 21 | SEQ ID NO: 65 & SEQ ID NO: 66 |

TABLE 1-continued

B19 VP2 Polypeptide Wild Type and Mutants

| Construct designation: | Mutation | Amino acid(s) mutated | Nucleic acid sequences used to construct | Primers used |
|---|---|---|---|---|
| T | (QQYTDQ to NNWTDT) + (HTYFPN to HTAFPN) + (KEYQQ to KEYAA) | See Construct O, Construct H, and Construct D | SEQ ID NO: 22 | SEQ ID NO: 67 & SEQ ID NO: 68 |
| U | (QQYTDQ to QQFTDT) + (HTYFPN to HTAFPN) + (KEYQQ to KEYAA) | Y401F and Q404T; Also see construct H and Construct D | SEQ ID NO: 23 | SEQ ID NO: 69 & SEQ ID NO: 70 |
| V | (QQYTDQ to QQFTDT) + (HTYFPN to HTAFPN) | Y401F and Q404T; Also see Construct H | SEQ ID NO: 24 | SEQ ID NO: 71 & SEQ ID NO: 72 |
| W | (QQYTDQ to QQWTDQ) + (HTYFPN to HTAFPN) + (KEYQQ to KEYAA) | See Construct B, Construct H, and Construct D | SEQ ID NO: 25 | SEQ ID NO: 73 & SEQ ID NO: 74 |
| X | (HTYFPN to HTAFPN) + (KEYQQ to KEYAA) | See Construct H and Construct D | SEQ ID NO: 26 | SEQ ID NO: 75 & SEQ ID NO: 76 |

The B19 VP2 Polypeptides were Examined for their Ability to Form B19 Virus Like Particles (VLPs) by Electron Microscopy.

For purification of B19 wtVLPs (B19 wild type VLPs) and B19 mutant VLPs (B19 mVLPs), cells were collected (750 rpm, 10 min) at 72 hrs post-infection by rBac, suspended in Tris buffer (20 mM Tris, 0.25M NaCl, pH8.5), downs homogenized, and incubated for 10 min at 45° C. The pH and density were adjusted to 7.2 and 1.30 g/ml, respectively, prior to overnight ultracentrifugation at 32,000 rpm in SW55Ti (Beckman Coulter, MO). VLP bands were collected, and dialyzed against Dulbecco's phosphate-buffered saline (DPBS). The protein concentrations of VLP stock solution were measured (Bio-Rad Protein Assay; BioRad, CA).

For electron microscopy, purified VLPs and mVLPs were loaded onto a formvar-carbon coated 300-mesh cupper grid, stained with 2% phosphotungstic acid (pH 6.8), and visualized under the transmission electron microscope (EM: 100S, JEOL Ltd., Tokyo, JPN).

Constructions of mutant B19 VLPs (mVLPs) were attempted using only the mutated B19 VP2 proteins; no other proteins were included in the mVLPs. Although a few of the VP2 mutants did not form mVLPs, most formed mVLPs that were morphologically similar to wild type VLPs (e.g., see FIG. 2A-FIG. 2I), but with varying yields; the tightness of VLP-assemblage also varied.

Hemagglutination Assays (HA) and Hemagglutination Inhibition Assays (HIA)

A hemagglutination assay of purified B19 VLPs was performed with human RBCs to study binding capacity to P antigen (See FIG. 5 and FIG. 6 which represent some embodiments of hemagglutination caused by P antigen binding, and possible effects therefrom). HIA assays determine the inhibition of hemagglutination by antibodies raised against VLPs made of wild type B19 VP2 protein ("wild type VLPs" or "wtVLPs") or VLPs made of the mutated B19 VP2 polypeptide ("mutant VLPs" or "mVLPs"); HIA assays are used to establish evidence for the presence of conformational epitopes capable of inducing neutralizing antibodies.

Immunization of rabbits and mice: Rabbits were immunized subcutaneously, and Balb/c mice were immunized intraperitoneally. Rabbits and mice were injected with 100 μg per injection twice at two weeks interval with the use of TITERMAX® (Catalog number H4397 from Sigma-Aldrich, MO, which is described as a block copolymer, CRL89-41, squalene (a metabolizable oil) and a unique microparticulate stabilizer) or ADJUPLEX™ Vaccine Adjuvant (an adjuvant platform based on a purified lecithin and carbomer homopolymer) and then with a final boost one month later. If necessary, maximum bleeding was done one week to 10 days after the final boost.

ELISA Assays: To carry out ELISA assays, VLPs diluted in PBS (pH7.2) were coated on ELISA plates (Immunolon II, Dynatech) for 1 hr at 37° C. After saturation of the plates with PBS containing 5% bovine serum albumin (5% PBSA) for 1 hour at 37° C., primary antibodies diluted with 1% PBSA were added for another one hour at 37° C. Alkaline phosphatase-labeled secondary antibodies and Sigma 104 substrate (Sigma-Aldrich, MO) were employed for the detection of bound primary antibodies.

Hemagglutination Assays (HA): Briefly, 100 μl of VLP solution (0.01 to 0.5 μg/ml in ADPBS [albumin-dextrose PBS; 0.05M PBS, pH 6.3, 0.2% Bovine serum albumin, 5 g/L dextrose]) was placed in the wells of a round-bottom microtiter plate, and 50 μl of 2% hRBC (human red blood cells that were pretested for the presence of P antigen using wild type VLPs as antigen: O type human blood; Innovative Research, MI) in ADPBS was added for 2 hours of incubation at 4° C. The result was read.

Hemagglutination Inhibition Assays (HIA): Fifty µl of antibodies serially diluted in ADPBS were incubated with 50 µl of VLPs diluted in ADPBS for 30 min at RT. Fifty µl of two percent hRBCs was then added for 2 hrs incubation at 4° C. prior to reading the outcome of hemagglutination.

Results of HA and HIA Assays: FIG. 3 shows results from hemagglutination assay (HA) of wtVLPs or mVLPs. Type O human red blood cells were employed in this HA. FIG. 4 includes results from hemagglutination inhibition assays of rabbit or mouse polyclonal antibodies raised against B19 VLPs containing wild type VP2 or mVP2. Type O human red blood cells and wild type VLPs were used in this assay.

Table 2 provides an overview summary of some characteristics of the various constructs and the respective mVLPs.

TABLE 2

B19 VP2 mutation analysis and summary of partial characterization

| Construct | Formation of VLPs | Hemagglutination (HA) by VLPs | Immunogenicity of VLPs in mice[1] | HIA[2] |
|---|---|---|---|---|
| A | Yes | No HA | OK | Yes (1/100) |
| B | Yes (increased yield) | Yes | High | Yes (1/100) |
| C | No | NA | NA | NA |
| D | Yes | Partial HA | Low | Yes (1/100 dilution) |
| E | Yes | Partial HA | N/A | No |
| F | Yes | No HA | High | Yes (1/500 dilution) |
| G | Yes | Partial HA | High | Yes (over 1/500 dilution) |
| H | Yes | Partial HA | Low | Yes (weak) |
| I | — | No HA | N/A | N/A |
| O | Yes | N/A | N/A | N/A |
| P | VLP formation but with significant unassembled material | N/A | N/A | N/A |
| W | VLP formation but with significant unassembled material | N/A | N/A | N/A |

Constructs J, K, M, and N did not yield purified mVLPs under these conditions.

[1]Immunogenicity in mice: wtVLPs do not hemagglutinate murine red blood cells. Still, it is not certain that there is absolutely no weak binding between them. Therefore, this result does not necessarily reflect the immunities of mVLPs in human.

[2]HIA (Hemagglutination inhibition assay): Inhibition of hemagglutination of wtVLPs by antibody raised against mVLPs. This test was carried out using murine polyclonal antibodies. TITERMAX ® adjuvant was employed for the immunization.

Table 3 shows cross-reactivities of rabbit sera raised against B19 wild type VLPs or B19 mVLPs. Antibodies were diluted to 1/4000 and their reactivities were measured by direct ELISA. Alkaline-phosphatase-tagged goat antibody anti-IgG of rabbit was used as secondary antibody, and the optical density was measured at 410 nm.

TABLE 3

Cross-Reactivities

| Antigen\ Rabbit sera | Wild type VLPs | <VLPs made from Construct A | <VLPs made from Construct B |
|---|---|---|---|
| Wild type VLPs | 0.408 | 0.608 | 0.749 |
| VLPs made from Construct A | 0.716 | 1.300 | 1.362 |
| VLPs made from Construct B | 1.006 | 1.985 | 2.018 |
| PBA with albumin (control negative) | 0.133 | 0.133 | 0.132 |

<indicates antibodies raised against this antigen

Table 4 shows the titration of mouse polyclonal antibodies raised against B19 wild type VLPs or B19 mutated VLPs. Antibody titers were measured by ELISA. Wild type VLPs are known to be non immunogenic in mice. The immunogen employed to raise each polyclonal antibodies were used as antigen for this analysis. ODs were measured at 410 nm. All antibodies gave less than 0.200 OD when they were reacted with bovine albumin as control negative antigen.

TABLE 4

Antibodies diluted to 1/500. ODs over 1.00 indicated in bold.

| Antigen\ sera | <Wild type | <Construct A | <Construct B | <Construct D | <HTYFPN | <Construct F | <Construct G |
|---|---|---|---|---|---|---|---|
| Wild type | 0.211 | 0.278 | 0.333 | 0.754 | 0.324 | 0.949 | 0.707 |
| Construct A | 0.235 | 0.615 | 0.755 | 1.786 | 0.598 | 2.398 | 1.96 |
| Construct B | 0.333 | 0.820 | 1.794 | 2.832 | 0.788 | 3.642 | 3.368 |
| Construct D | 0.210 | 0.591 | 0.645 | 1.103 | 0.481 | 1.511 | 1.287 |
| HTYFPN | 0.199 | 0.502+ | 0.467 | 1.032 | 0.385 | 1.259 | 0.803 |

<indicates antibodies raised against this antigen mVLPs made from Construct F were HA-negative, immunogenic in mice (Table 2 and FIG. 3), and induced antibodies capable of inhibiting HA by wtVLPs (FIG. 4).

Of three targeted locations, the "Y" in $QQY_{401}TDQ$ and $HTY_{392}FPN$, which are located in the P-antigen binding pocket, appear to be influential in forming viral ligand for P-antigen. Construct A formed mVLPs; the mVLPs were HA negative, but were moderately immunogenic in mice. Construct B mVLPs made good mVLPs with good yield; the mVLPs were immunogenic in mice, but they were HA positive. Rabbit antibodies anti-wtVLPs, anti-Construct A mVLPs, and anti-Construct B mVLPs were generated. These rabbit sera showed the high cross-reactivities among wtVLPs, Construct A mVLPs and Construct B mVLPs (Table 3).

Construct D mVLPs induced HIA positive antibodies in mice but were HA positive (FIG. 4 and Table 4). Construct F mVLPs were HA negative, induced high titer antibody immune response in mice (Table 4), and gave good HIA titer against wtVLPs (FIG. 4). Construct G mVLPs were partially negative for HA, but induced murine antibodies with high titer for HIA. The three Qs in $Q_{393}Q_{400}YTDQ_{404}$ seem to have partial influence for HA, but may be more influential for the formation of VLPs, particularly the third Q ($Q_{404}$). The two Qs in $KEYQ_{368}Q_{369}$ appeared to have minor effects on HA. At this time, we have not successfully purified VLPs from the VP2 mutants of Construct J, Construct M, Construct N, or Construct C.

"QQYTDQ", especially the residue Y, appears influential for the binding capability of Parvovirus B19 to RBCs. Any of three "Q"s in "QQYTDQ", "QQ" in "KEYQQ" and "Y" in HTYFPN appeared to affect the affinity of mVLPs to RBCs, suggesting some contributions of these amino acids. VP2 with the mutation from Y to A in HT$\underline{Y}$FPN as well as VP2 with the mutation from QQ to AA in KEY$\underline{QQ}$ formed mVLPs with weaker affinity to RBCs than wtVLPs. Adding four amino acids "DPIG" after "QQYTDQ" appeared to abolish the capacity of VP2 protein to form VLPs.

mVLPs composed of VP2 mutated from Y to F in QQYTDQ (i.e., construct A) formed VLPs morphologically comparable to wtVLPs, appeared to abolish hemagglutination of RBCs, and induced antibodies in mice and rabbit, that recognized wtVLPs as well as other mVLPs. Also, antibodies raised against construct A mVLPs were also capable of blocking hemagglutination of wtVLPs. Y and F have the same amino acid back bone structure except that Y has a hydroxyl group at position 4 of the benzene ring while F has none.

mVLPs made from construct B mVLPs (i.e., Y to W in QQYTDQ) formed mVLPs morphologically comparable to wtVP2. Although they hemagglutinated RBCs, they induced high titer antibodies in mice and rabbit, RBCs of which are known not to bind to B19. Antibodies to construct B mVLPs recognized wtVLPs as well as other mVLPs, and also blocked hemagglutination of wtVLPs, indicating that it shared cross-reactive epitopes with wtVLPs and other mVLPs. In fact, construct B mVLPs yielded higher and formed better VLPs than wtVLPs and construct A mVLPs when observed under the electron microscope, and were immunogenic in mice and rabbit.

Rabbit anti-sera that were raised against wild type VLPs, recognized construct A mVLPs and construct B mVLPs, as determined by ELISA assays, demonstrating again the presence of cross-reactive epitopes on these mVLPs.

Construct C mVLPs (i.e., with mutation from Y to A in QQYTDQ) did not form purifiable VLPs under the condition employed in this study.

Mutations of three Qs in construct F (i.e., QQYTDQ to NNFTDT) or in construct G (i.e., QQYTDQ to NNYTDT) resulted in formation of mVLPs that were not only morphologically similar to wtVLPs, but were also immunogenic. Construct F mVLPs and construct G mVLPs did not hemagglutinate or partially hemagglutinated RBC, respectively. However, constructs J, K, M, and N were not able to form stable mVLPs under the condition employed in this study. This may indicate the influence of the third "Q" in this ligand site (i.e., QQYTQ) in the formation of mVLPs and in the binding to P antigen. The choices of substituted amino acids can, in some instances, influence not only for the formation of mVLPs but also the mVLP immunogenicity.

When the two "Q"s in "KEYQQ" were replaced by AA (i.e., construct D), the resulting mVLPs were morphologically comparable to wtVLPs and they could partially hemagglutinated RBCs, but they were not immunogenic in mice. When the two "Q"s in "KEYQQ" were replaced by NN (i.e., construct E), mVLPs were morphologically good and comparable to wtVLPs; they hemagglutinated RBCs and were immunogenic in mice.

Mutation of Y in HTYFPN to HTFFPN (Construct I) resulted in formation of good mVLPs which partially hemagglutinated RBCs but their immunogenicity in mice was low.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

In certain instances, sequences disclosed herein are included in publicly-available databases, such as GEN-BANK® and SWISSPROT. Unless otherwise indicated or apparent the references to such publicly-available databases are references to the most recent version of the database as of the filing date of this application.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A method for inhibiting in an animal a parvovirus infection, an erythrovirus infection, or a parvovirus B19 infection, comprising one or more administrations of one or more compositions comprising an mVLP comprising a polypeptide,
wherein
the compositions may be the same or different if there is more than one administration,
the polypeptide comprises a VP2 polypeptide with at least one amino acid modification relative to a wild type VP2,
the wild type VP2 has the amino acid sequence of SEQ ID NO: 1,
the at least one amino acid modification (1) comprises (a) Y401F and (b) Q399N or Q404T or (2) is Y401F, and
the polypeptide is not construct J.

2. The method of claim 1, wherein at least one of the one or more compositions does not comprise an adjuvant.

3. The method of claim 1, wherein at least one of the one or more compositions further comprises a carrier or an adjuvant.

4. The method of claim 1, wherein at least one of the one or more compositions further comprises squalene, RIM adjuvant system, QS21, GM-CSF, alum hydro gel, monophosphoryl lipid A, trehalose dimycolate, Toll-like receptor ligands, Toil-like receptor agonists, CpG oligodeoxynucleotides, cell wall skeleton, MF59, or combinations thereof.

5. The method of claim 1, wherein at least one of the one or more the compositions comprises a pharmaceutical composition or a vaccine.

6. The method of claim 1, wherein at least one of the one or more administrations comprises parenteral administration mucosal administration, intravenous administration, subcutaneous administration, topical administration, intradermal administration, oral administration, sublingual administration, intranasal administration, or intramuscular administration.

7. The method of claim 1, wherein if there is more than one administration at least one composition used for at least one administration is different from the composition of at least one other administration.

8. The method of claim 1, wherein the mVLP of at least one of the one or more compositions is administered to the animal in an amount of from about 0.01 trig of mVLP/kg animal body weight to about 15 mg of mVLP/kg animal body weight.

9. The method of claim 1, wherein the animal is a human or a primate.

10. The method of claim 1, wherein the animal is in need of the inhibiting.

11. The method of claim 1, wherein the method is for inhibiting an erythrovirus infection.

12. The method of claim 1, wherein the method is for inhibiting a parvovirus B19 infection.

13. The method of claim 1, wherein the method induces an immune response.

14. The method of claim 1, wherein the at least one amino acid modification comprises (a) 1401F and (b) Q399N or Q404T and further comprises an insertion, a deletion, or a substitution.

15. The method of claim 1, wherein the polypeptide sequence has at least about 90% identity to SEQ ID NO: 1.

16. The method of claim 1, wherein the polypeptide sequence has at least about 95% identity to SEQ ID NO: 1.

17. The method of claim 1, wherein the polypeptide is construct A.

18. The method of claim 1, wherein the polypeptide is Construct F.

19. The method of claim 1, wherein the at least one amino acid modification comprises (a) Y401F and (b) Q399N or Q404T.

20. The method of claim 1, wherein the mVLP has reduced binding to P antigen compared to wtVLP, the mVLP has no detectable binding to P antigen, the mVLP has reduced hemagglutination of red blood cells compared to wtVLP, or the mVLP has no detectable hemagglutination.

21. The method of claim 1, wherein the mVLP has one or more neutralizing epitopes.

22. The method of claim 1, wherein the mVLP induces the production of antibodies in an animal, where the antibodies produced are capable of reducing or inhibiting hemagglutination by wtVLP.

23. A method for inducing an immune response in an animal comprising one or more administrations of one or more compositions comprising an mVLP comprising a polypeptide, wherein the compositions may be the same or different if there is more than one administration, the polypeptide comprises a VP2 polypeptide with at least one amino acid modification relative to a wild type VP2, the wild type VP2 has the amino acid sequence of SEQ ID NO: 1, the at least one amino acid modification (1) comprises (a) Y401F and (h) Q399N or Q404T, (2) is Y401F, (3) is Q368A and Q369A, (4) is Q399N, Q400N, and Q404T, or (5) is Y392A, and the polypeptide is not construct J.

24. The method of claim 23, wherein at least one of the one or more compositions does not comprise an adjuvant.

25. The method of claim 23, wherein at least one of the one or more compositions further comprises a carrier or an adjuvant.

26. The method of claim 23, wherein if there is more than one administration at least one composition used for at least one administration is different from the composition of at least one other administration.

27. The method of claim 23, wherein the polypeptide sequence has at least about 90% identity to SEQ ID NO: 1.

28. The method of claim 23, wherein the polypeptide sequence has at least about 95% identity to SEQ ID NO: 1.

29. The method of claim 23, wherein the at least one amino acid modification comprises (a) Y401F and (h) Q399N or Q404T.

30. The method of claim 23, wherein the polypeptide is selected from the group consisting of construct A, construct D, construct F, construct G, and construct H.

31. The method of claim 23, wherein the polypeptide is Construct F.

* * * * *

```
                          SEQUENCE LISTING

<160> NUMBER OF SEQ ID NOS: 76

<210> SEQ ID NO 1
    <211> LENGTH: 554
    <212> TYPE: PRT
    <213> ORGANISM: Parvovirus B19

<400> SEQUENCE: 1

Met Thr Ser Val Asn Ser Ala Glu Ala Ser Thr Gly Ala Gly Gly Gly
    1               5                   10                  15

Gly Ser Asn Pro Val Lys Ser Met Trp Ser Glu Gly Ala Thr Phe Ser
                    20                  25                  30

Ala Asn Ser Val Thr Cys Thr Phe Ser Arg Gln Phe Leu Ile Pro Tyr
                35                  40                  45

Asp Pro Glu His His Tyr Lys Val Phe Ser Pro Ala Ala Ser Ser Cys
        50                  55                  60

His Asn Ala Ser Gly Lys Glu Ala Lys Val Cys Thr Ile Ser Pro Ile
    65                  70                  75                  80

Met Gly Tyr Ser Thr Pro Trp Arg Tyr Leu Asp Phe Asn Ala Leu Asn
                    85                  90                  95

Leu Phe Phe Ser Pro Leu Glu Phe Gln His Leu Ile Glu Asn Tyr Gly
                    100                 105                 110

Ser Ile Ala Pro Asp Ala Leu Thr Val Thr Ile Ser Glu Ile Ala Val
                115                 120                 125

Lys Asp Val Thr Asp Lys Thr Gly Gly Gly Val Gln Val Thr Asp Ser
        130                 135                 140

Thr Thr Gly Arg Leu Cys Met Leu Val Asp His Glu Tyr Lys Tyr Pro
    145                 150                 155                 160

Tyr Val Leu Gly Gln Gly Gln Asp Thr Leu Ala Pro Glu Leu Pro Ile
                    165                 170                 175

Trp Val Tyr Phe Pro Pro Gln Tyr Ala Tyr Leu Thr Val Gly Asp Val
                    180                 185                 190

Asn Thr Gln Gly Ile Ser Gly Asp Ser Lys Lys Leu Ala Ser Glu Glu
                195                 200                 205

Ser Ala Phe Tyr Val Leu Glu His Ser Ser Phe Gln Leu Leu Gly Thr
        210                 215                 220

Gly Gly Thr Ala Thr Met Ser Tyr Lys Phe Pro Val Pro Pro Glu
    225                 230                 235                 240

Asn Leu Glu Gly Cys Ser Gln His Phe Tyr Glu Met Tyr Asn Pro Leu
                    245                 250                 255

Tyr Gly Ser Arg Leu Gly Val Pro Asp Thr Leu Gly Gly Asp Pro Lys
                    260                 265                 270

Phe Arg Ser Leu Thr His Glu Asp His Ala Ile Gln Pro Gln Asn Phe
                275                 280                 285
```

```
Met Pro Gly Pro Leu Val Asn Ser Val Ser Thr Lys Glu Gly Asp Ser
            290                 295                 300

Ser Asn Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
                340                 345                 350

Ser His Gly Gln Thr Thr Tyr Gly Asn Ala Glu Asp Lys Glu Tyr Gln
            355                 360                 365

Gln Gly Val Gly Arg Phe Pro Asn Glu Lys Glu Gln Leu Lys Gln Leu
370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
                435                 440                 445

Leu His Gln Pro Pro Pro Gln Ile Phe Leu Lys Ile Leu Pro Gln Ser
450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
                515                 520                 525

Asp Ala Lys Gln His His Arg His Gly Tyr Glu Lys Pro Glu Glu Leu
            530                 535                 540

Trp Thr Ala Lys Ser Arg Val His Pro Leu
545                 550

<210> SEQ ID NO 2
<211> LENGTH: 1665
<212> TYPE: DNA
<213> ORGANISM: Parvovirus B19

<400> SEQUENCE: 2
atgacttcag ttaattctgc agaagccagc actggtgcag agggggggg cagtaatcct      60 gtcaaaagca tgtggagtga gggggccact tttagtgcca actctgtgac ttgtacattt     120
tctagacagt ttttaattcc atatgaccca gagcaccatt ataaggtgtt ttctcccgca     180
gcaagtagct gccacaatgc cagtggaaag gaggcaaagg tttgcaccat tagtcccata     240
atgggatact caaccccatg gagatattta gatttaatg ctttaaactt atttttttca     300
cctttagagt ttcagcactt aattgaaaat tatggaagta tagctcctga tgctttaact     360
gtaaccatat cagaaattgc tgttaaggat gttacagaca aaactggagg ggggtgcag      420 gttactgaca gcactacagg gcgcctatgc atgttagtag accatgaata caagtaccca     480
tatgtgttag gcaaggtca agatacttta gccccagaac ttcctatttg ggtatacttt     540 cccccctcaat atgcttactt aacagtagga gatgttaaca cacaaggaat ttctggagac     600
```

```
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca acacttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tcagcaagga gtgggtagat ttccaaatga aaagaacag      1140 ctaaaacagt tacagggttt aaacatgcac acctactttc ccaataaagg aacccagcaa     1200
tatacagatc aaattgagcg ccccctaatg gtgggttctg tatggaacag aagagccctt     1260
cactatgaaa gccagctgtg gagtaaaatt ccaaatttag atgacagttt taaaactcag     1320
tttgcagcct taggaggatg gggtttgcat cagccacctc ctcaaatatt tttaaaaata     1380
ttaccacaaa gtgggccaat tggaggtatt aaatcaatgg gaattactac cttagttcag     1440
tatgccgtgg gaattatgac agtaaccatg acatttaaat tggggcccg taaagctacg      1500 ggacggtgga atcctcaacc tggagtatat cccccgcacg cagcaggtca tttaccatat     1560
gtactatatg acccctacagc tacagatgca aaacaacacc acagacatgg atatgaaaag    1620
cctgaagaat tgtggacagc caaaagccgt gtgcacccat tgtaa                     1665

<210> SEQ ID NO 3
<211> LENGTH: 1665
<212> TYPE: DNA
<213> ORGANISM: Artificial Sequence
<220> FEATURE:
<223> OTHER INFORMATION: Construct A

<400> SEQUENCE: 3
atgacttcag ttaattctgc agaagccagc actggtgcag agggggggg cagtaatcct        60 gtcaaaagca tgtggagtga gggggccact tttagtgcca actctgtgac ttgtacattt      120
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt atttttttca      300 ccttttagagt ttcagcactt aattgaaaat tatggaagta tagctcctga tgcttttaact   360 gtaaccatat cagaaattgc tgttaaggat gttacagaca aaactggagg ggggtgcag       420 gttactgaca gcactacagg gcgcctatgc atgttagtag accatgaata caagtaccca      480
tatgtgttag ggcaaggtca agatacttta gccccagaac ttcctatttg ggtatacttt     540
ccccctcaat atgcttactt aacagtagga gatgttaaca cacaaggaat ttctggagac      600
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca acacttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
```

```
gacacagata aatatgtcac aggaataaat gctatttctc atggtcagac cacttatggt    1080
aacgctgaag acaaagagta tcagcaagga gtgggtagat ttccaaatga aaaagaacag    1140
ctaaaacagt tacagggttt aaacatgcac acctactttc ccaataaagg aacccagcaa    1200
tttacagatc aaattgagcg cccectaatg gtgggtctg tatggaacag aagagccctt     1260
cactatgaaa gccagctgtg gagtaaaatt ccaaatttag atgacagttt taaaactcag    1320
tttgcagcct taggaggatg gggtttgcat cagccacctc ctcaaatatt tttaaaaata    1380
ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga atcctcaacc tggagtatat ccccgcacg cagcaggtca tttaccatat     1560
gtactatatg accctacagc tacagatgca aaacaacacc acagacatgg atatgaaaag    1620
cctgaagaat tgtggacagc caaaagccgt gtgcacccat tgtaa                    1665
```

<210> SEQ ID NO 4
<211> LENGTH: 1665
<212> TYPE: DNA
<213> ORGANISM: Artificial Sequence
<220> FEATURE:
<223> OTHER INFORMATION: Construct B

<400> SEQUENCE: 4

```
atgacttcag ttaattctgc agaagccagc actggtgcag aggggggggg cagtaatcct     60
gtcaaaagca tgtggagtga gggggccact tttagtgcca actctgtgac ttgtacattt    120
tctagacagt ttttaattcc atatgaccca gagcaccatt ataaggtgtt ttctcccgca    180
gcaagtagct gccacaatgc cagtggaaag gaggcaaagg tttgcaccat tagtcccata    240
atgggatact caaccccatg gagatatttta gattttaatg ctttaaactt attttttca    300 cctttagagt ttcagcactt aattgaaaat tatggaagta tagctcctga tgctttaact    360
gtaaccatat cagaaattgc tgttaaggat gttacagaca aaactggagg ggggtgcag    420 gttactgaca gcactacagg gcgcctatgc atgttagtag accatgaata caagtaccca    480
tatgtgttag ggcaaggtca agatacttta gccccagaac ttcctatttg ggtatacttt    540 cccctcaat atgcttactt aacagtagga gatgttaaca cacaaggaat ttctggagac    600
agcaaaaaat tagcaagtga agaatcagca ttttatgttt tggaacacag ttcttttcag    660
cttttaggta caggaggtac agcaactatg tcttataagt ttcctccagt gcccccagaa    720
aatttagagg gctgcagtca acactttat gagatgtaca atcccttata cggatcccgc     780
ttaggggttc ctgacacatt aggaggtgac ccaaaattta gatctttaac acatgaagac    840
catgcaattc agccccaaaa cttcatgcca gggccactag taaactcagt gtctacaaag    900
gagggagaca gctctaatac tggagctggg aaagccttaa caggccttag cacaggtacc    960
tctcaaaaca ctagaatatc cttacgcccg gggccagtgt ctcagccgta ccaccactgg    1020
gacacagata aatatgtcac aggaataaat gctatttctc atggtcagac cacttatggt    1080
aacgctgaag acaaagagta tcagcaagga gtgggtagat ttccaaatga aaaagaacag    1140
ctaaaacagt tacagggttt aaacatgcac acctactttc ccaataaagg aacccagcaa    1200
tggacagatc aaattgagcg cccectaatg gtgggtctg tatggaacag aagagccctt     1260
cactatgaaa gccagctgtg gagtaaaatt ccaaatttag atgacagttt taaaactcag    1320
tttgcagcct taggaggatg gggtttgcat cagccacctc ctcaaatatt tttaaaaata    1380
```

```
ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga atcctcaacc tggagtatat ccccgcacg cagcaggtca tttaccatat    1560
gtactatatg accctacagc tacagatgca aaacaacacc acagacatgg atatgaaaag    1620
cctgaagaat tgtggacagc caaaagccgt gtgcacccat tgtaa                   1665

<210> SEQ ID NO 5
<211> LENGTH: 1665
<212> TYPE: DNA
<213> ORGANISM: Artificial Sequence
<220> FEATURE:
<223> OTHER INFORMATION: Construct C

<400> SEQUENCE: 5
atgacttcag ttaattctgc agaagccagc actggtgcag aggggggggg cagtaatcct      60
gtcaaaagca tgtggagtga gggggccact tttagtgcca actctgtgac ttgtacattt    120
tctagacagt ttttaattcc atatgaccca gagcaccatt ataaggtgtt ttctcccgca    180
gcaagtagct gccacaatgc cagtggaaag gaggcaaagg tttgcaccat tagtcccata    240
atgggatact caaccccatg gagatattta gattttaatg ctttaaactt attttttca    300 cctttagagt ttcagcactt aattgaaaat tatggaagta tagctcctga tgctttaact    360
gtaaccatat cagaaattgc tgttaaggat gttacagaca aaactggagg ggggtgcag    420 gttactgaca gcactacagg gcgcctatgc atgttagtag accatgaata caagtaccca    480
tatgtgttag ggcaaggtca agatacttta gccccagaac ttcctatttg ggtatacttt    540 cccctcaat atgcttactt aacagtagga gatgttaaca cacaaggaat ttctggagac    600
agcaaaaaat tagcaagtga agaatcagca ttttatgttt tggaacacag ttcttttcag    660
cttttaggta caggaggtac agcaactatg tcttataagt ttcctccagt gccccagaa    720 aatttagagg gctgcagtca acactttta gagatgtaca atcccttata cggatcccgc    780
ttaggggttc ctgacacatt aggaggtgac ccaaaattta gatctttaac acatgaagac    840
catgcaattc agccccaaaa cttcatgcca gggccactag taaactcagt gtctacaaag    900
gagggagaca gctctaatac tggagctggg aaagccttaa caggccttag cacaggtacc    960
tctcaaaaca ctagaatatc cttacgcccg gggccagtgt ctcagccgta ccaccactgg   1020
gacacagata aatatgtcac aggaataaat gctatttctc atggtcagac cacttatggt   1080
aacgctgaag acaaagagta tcagcaagga gtgggtagat tccaaatga aaagaacag   1140 ctaaaacagt tacagggttt aaacatgcac acctactttc ccaataaagg aacccagcaa   1200
gctacagatc aaattgagcg ccccctaatg gtgggttctg tatggaacag aagagccctt   1260
cactatgaaa gccagctgtg gagtaaaatt ccaaatttag atgacagttt taaactcag   1320 tttgcagcct taggaggatg gggttttgcat cagccacctc ctcaaatatt tttaaaaata   1380
ttaccacaaa gtgggccaat tggaggtatt aaatcaatgg gaattactac cttagttcag   1440
tatgccgtgg gaattatgac agtaaccatg acatttaaat tggggccccg taaagctacg   1500
ggacggtgga atcctcaacc tggagtatat ccccgcacg cagcaggtca tttaccatat   1560
gtactatatg accctacagc tacagatgca aaacaacacc acagacatgg atatgaaaag   1620
cctgaagaat tgtggacagc caaaagccgt gtgcacccat tgtaa                    1665

<210> SEQ ID NO 6
<211> LENGTH: 1665
```

```
<212> TYPE: DNA
<213> ORGANISM: Artificial Sequence
<220> FEATURE:
<223> OTHER INFORMATION: Construct D

<400> SEQUENCE: 6
atgacttcag ttaattctgc agaagccagc actggtgcag gagggggggg cagtaatcct      60
gtcaaaagca tgtggagtga gggggccact tttagtgcca actctgtgac ttgtacattt     120
tctagacagt ttttaattcc atatgaccca gagcaccatt ataaggtgtt ttctcccgca     180
gcaagtagct gccacaatgc cagtggaaag gaggcaaagg tttgcaccat tagtcccata     240
atgggatact caaccccatg gagatattta gattttaatg ctttaaactt atttttttca     300
cctttagagt ttcagcactt aattgaaaat tatggaagta tagctcctga tgctttaact     360
gtaaccatat cagaaattgc tgttaaggat gttacagaca aaactggagg ggggggtgcag    420
gttactgaca gcactacagg gcgcctatgc atgttagtag accatgaata caagtaccca     480
tatgtgttag gcaaggtca agatacttta gccccagaac ttcctatttg ggtatacttt      540
cccectcaat atgcttactt aacagtagga gatgttaaca cacaaggaat tctggagac      600
agcaaaaaat tagcaagtga agaatcagca ttttatgttt tggaacacag ttcttttcag     660
cttttaggta caggaggtac agcaactatg tcttataagt ttcctccagt gcccccagaa     720
aatttagagg gctgcagtca cactttttat gagatgtaca atcccttata cggatcccgc     780
ttaggggttc ctgacacatt aggaggtgac ccaaaattta gatctttaac acatgaagac     840
catgcaattc agccccaaaa cttcatgcca gggccactag taaactcagt gtctacaaag     900
gagggagaca gctctaatac tggagctggg aaagccttaa caggccttag cacaggtacc     960
tctcaaaaca ctagaatatc cttacgcccg gggccagtgt ctcagccgta ccaccactgg    1020
gacacagata aatatgtcac aggaataaat gctatttctc atggtcagac cacttatggt    1080
aacgctgaag acaaagagta tgctgctgga gtgggtagat ttccaaatga aaaagaacag    1140
ctaaaacagt tacagggttt aaacatgcac acctactttc ccaataaagg aacccagcaa    1200
tatacagatc aaattgagcg ccccctaatg gtgggttctg tatggaacag aagagccctt    1260
cactatgaaa gccagctgtg gagtaaaatt ccaaatttag atgacagttt taaaactcag    1320
tttgcagcct taggaggatg gggttttgcat cagccacctc ctcaaatatt tttaaaaata    1380
ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga tcctcaacc tggagtatat cccccgcacg cagcaggtca tttaccatat    1560
gtactatatg accctacagc tacagatgca aaacaacacc acagacatgg atatgaaaag    1620
cctgaagaat tgtggacagc caaaagccgt gtgcacccat tgtaa                    1665

<210> SEQ ID NO 7
<211> LENGTH: 1665
<212> TYPE: DNA
<213> ORGANISM: Artificial Sequence
<220> FEATURE:
<223> OTHER INFORMATION: Construct E

<400> SEQUENCE: 7
atgacttcag ttaattctgc agaagccagc actggtgcag gagggggggg cagtaatcct      60
gtcaaaagca tgtggagtga gggggccact tttagtgcca actctgtgac ttgtacattt     120
tctagacagt ttttaattcc atatgaccca gagcaccatt ataaggtgtt ttctcccgca     180
```

```
gcaagtagct gccacaatgc cagtggaaag gaggcaaagg tttgcaccat tagtcccata        240
atgggatact caaccccatg gagatattta gattttaatg ctttaaactt attttttttca       300 cctttagagt ttcagcactt aattgaaaat tatggaagta tagctcctga tgctttaact       360
gtaaccatat cagaaattgc tgttaaggat gttacagaca aaactggagg ggggtgcag        420 gttactgaca gcactacagg gcgcctatgc atgttagtag accatgaata caagtaccca       480
tatgtgttag ggcaaggtca agatacttta gccccagaac ttcctatttg ggtatacttt       540 cccccctcaat atgcttactt aacagtagga gatgttaaca cacaaggaat ttctggagac     600
agcaaaaaat tagcaagtga agaatcagca ttttatgttt tggaacacag ttcttttcag       660
cttttaggta caggaggtac agcaactatg tcttataagt ttcctccagt gcccccagaa       720
aatttagagg gctgcagtca acactttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900 gaggagaca gctctaatac tggagctggg aaagccttaa caggccttag cacaggtacc       960
tctcaaaaca ctagaatatc cttacgcccg gggccagtgt ctcagccgta ccaccactgg      1020
gacacagata aatatgtcac aggaataaat gctatttctc atggtcagac cacttatggt      1080
aacgctgaag acaaagagta taacaacgga gtgggtagat tccaaatga aaaagaacag      1140 ctaaaacagt tacagggttt aaacatgcac acctactttc ccaataaagg aacccagcaa     1200
tatacagatc aaattgagcg ccccctaatg gtgggttctg tatggaacag aagagccctt      1260
cactatgaaa gccagctgtg gagtaaaatt ccaaatttag atgacagttt taaaactcag     1320
tttgcagcct taggaggatg gggtttgcat cagccacctc ctcaaatatt tttaaaaata    1380
ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga atcctcaacc tggagtatat ccccccgcacg cagcaggtca tttaccatat    1560
gtactatatg accctacagc tacagatgca aaacaacacc acagacatgg atatgaaaag   1620
cctgaagaat tgtggacagc caaaagccgt gtgcacccat tgtaa                         1665
```

<210> SEQ ID NO 8
<211> LENGTH: 1665
<212> TYPE: DNA
<213> ORGANISM: Artificial Sequence
<220> FEATURE:
<223> OTHER INFORMATION: Construct F

<400> SEQUENCE: 8

```
atgacttcag ttaattctgc agaagccagc actggtgcag gagggggggg cagtaatcct         60
gtcaaaagca tgtggagtga gggggccact tttagtgcca actctgtgac ttgtacattt        120
tctagacagt ttttaattcc atatgaccca gagcaccatt ataaggtgtt ttctcccgca       180
gcaagtagct gccacaatgc cagtggaaag gaggcaaagg tttgcaccat tagtcccata        240
atgggatact caaccccatg gagatattta gattttaatg ctttaaactt attttttttca       300 cctttagagt ttcagcactt aattgaaaat tatggaagta tagctcctga tgctttaact       360
gtaaccatat cagaaattgc tgttaaggat gttacagaca aaactggagg ggggtgcag        420 gttactgaca gcactacagg gcgcctatgc atgttagtag accatgaata caagtaccca       480
tatgtgttag ggcaaggtca agatacttta gccccagaac ttcctatttg ggtatacttt       540 cccccctcaat atgcttactt aacagtagga gatgttaaca cacaaggaat ttctggagac     600
```

```
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca acacttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac acttatggt      1080 aacgctgaag acaaagagta tcagcaagga gtgggtagat ttccaaatga aaagaacag      1140 ctaaaacagt tacagggttt aaacatgcac acctactttc ccaataaagg aaccaacaac     1200
tttacagata acattgagcg ccccctaatg gtgggttctg tatggaacag aagagccctt     1260
cactatgaaa gccagctgtg gagtaaaatt ccaaatttag atgacagttt taaaactcag     1320
tttgcagcct taggaggatg gggtttgcat cagccacctc ctcaaatatt tttaaaaata     1380
ttaccacaaa gtgggccaat tggaggtatt aaatcaatgg gaattactac cttagttcag     1440
tatgccgtgg gaattatgac agtaaccatg acatttaaat tggggccccg taaagctacg     1500
ggacggtgga atcctcaacc tggagtatat ccccgcacg cagcaggtca tttaccatat      1560
gtactatatg accctacagc tacagatgca aaacaacacc acagacatgg atatgaaaag     1620
cctgaagaat tgtggacagc caaaagccgt gtgcacccat tgtaa                     1665
```

<210> SEQ ID NO 9
<211> LENGTH: 1665
<212> TYPE: DNA
<213> ORGANISM: Artificial Sequence
<220> FEATURE:
<223> OTHER INFORMATION: Construct G

<400> SEQUENCE: 9

```
atgacttcag ttaattctgc agaagccagc actggtgcag agggggggg cagtaatcct       60 gtcaaaagca tgtggagtga gggggccact tttagtgcca actctgtgac ttgtacatt      120 tctagacagt tttttaattcc atatgaccca gagcaccatt ataaggtgtt ttctcccgca     180
gcaagtagct gccacaatgc cagtggaaag gaggcaaagg tttgcaccat tagtcccata     240
atgggatact caaccccatg gagatattta gattttaatg ctttaaactt attttttca      300 cctttagagt ttcagcactt aattgaaaat tatggaagta tagctcctga tgctttaact     360
gtaaccatat cagaaattgc tgttaaggat gttacagaca aaactggagg ggggtgcag      420 gttactgaca gcactacagg gcgcctatgc atgttagtag accatgaata caagtaccca     480
tatgtgttag ggcaaggtca agatacttta gccccagaac ttcctatttg ggtatacttt     540 cccccctcaat atgcttactt aacagtagga gatgttaaca cacaaggaat ttctggagac     600
agcaaaaaat tagcaagtga agaatcagca ttttatgttt tggaacacag ttcttttcag     660
cttttaggta caggaggtac agcaactatg tcttataagt ttcctccagt gcccccagaa     720
aatttagagg gctgcagtca acacttttat gagatgtaca atcccttata cggatcccgc     780
ttaggggttc ctgacacatt aggaggtgac ccaaaattta gatctttaac acatgaagac     840
catgcaattc agccccaaaa cttcatgcca gggccactag taaactcagt gtctacaaag     900
gagggagaca gctctaatac tggagctggg aaagccttaa caggccttag cacaggtacc     960
```

```
tctcaaaaca ctagaatatc cttacgcccg gggccagtgt ctcagccgta ccaccactgg    1020
gacacagata aatatgtcac aggaataaat gctatttctc atggtcagac cacttatggt    1080
aacgctgaag acaaagagta tcagcaagga gtgggtagat ttccaaatga aaagaacag    1140 ctaaaacagt tacagggttt aaacatgcac acctactttc ccaataaagg aaccaacaac    1200
tatacagata acattgagcg ccccctaatg gtgggttctg tatggaacag aagagccctt    1260
cactatgaaa gccagctgtg gagtaaaatt ccaaatttag atgacagttt taaaactcag    1320
tttgcagcct taggaggatg ggtttgcat cagccacctc ctcaaatatt tttaaaaata    1380
ttaccacaaa gtgggccaat tggaggtatt aaatcaatgg gaattactac cttagttcag    1440
tatgccgtgg gaattatgac agtaaccatg acatttaaat ggggccccg taaagctacg    1500 ggacggtgga atcctcaacc tggagtatat ccccgcacg cagcaggtca tttaccatat    1560
gtactatatg accctacagc tacagatgca aaacaacacc acagacatgg atatgaaaag    1620
cctgaagaat tgtggacagc caaaagccgt gtgcacccat tgtaa                    1665

<210> SEQ ID NO 10
<211> LENGTH: 1665
<212> TYPE: DNA
<213> ORGANISM: Artificial Sequence
<220> FEATURE:
<223> OTHER INFORMATION: Construct H

<400> SEQUENCE: 10
atgacttcag ttaattctgc agaagccagc actggtgcag aggggggggg cagtaatcct     60
gtcaaaagca tgtggagtga gggggccact tttagtgcca actctgtgac ttgtacattt    120
tctagacagt ttttaattcc atatgaccca gagcaccatt ataaggtgtt ttctcccgca    180
gcaagtagct gccacaatgc cagtggaaag gaggcaaagg tttgcaccat tagtcccata    240
atgggatact caaccccatg gagatattta gattttaatg ctttaaactt attttttca    300 cctttagagt ttcagcactt aattgaaaat tatggaagta tagctcctga tgctttaact    360
gtaaccatat cagaaattgc tgttaaggat gttacagaca aaactggagg ggggggtgcag    420 gttactgaca gcactacagg gcgcctatgc atgttagtag accatgaata caagtaccca    480
tatgtgttag ggcaaggtca agatacttta gccccagaac ttcctatttg gtatactttt    540 cccctcaat atgcttactt aacagtagga gatgttaaca cacaaggaat ttctggagac    600
agcaaaaaat tagcaagtga agaatcagca ttttatgttt tggaacacag ttcttttcag    660
cttttaggta caggaggtac agcaactatg tcttataagt ttcctccagt gcccccagaa    720
aatttagagg gctgcagtca acacttttat gagatgtaca atcccttata cggatcccgc    780
ttaggggttc ctgacacatt aggaggtgac ccaaaattta gatctttaac acatgaagac    840
catgcaattc agccccaaaa cttcatgcca gggccactag taaactcagt gtctacaaag    900
gagggagaca gctctaatac tggagctggg aaagccttaa caggccttag cacaggtacc    960
tctcaaaaca ctagaatatc cttacgcccg gggccagtgt ctcagccgta ccaccactgg   1020
gacacagata aatatgtcac aggaataaat gctatttctc atggtcagac cacttatggt   1080
aacgctgaag acaaagagta tcagcaagga gtgggtagat ttccaaatga aaagaacag    1140 ctaaaacagt tacagggttt aaacatgcac accgcttttc ccaataaagg aaccagcaa    1200 tatacagatc aaattgagcg ccccctaatg gtgggttctg tatggaacag aagagccctt   1260
cactatgaaa gccagctgtg gagtaaaatt ccaaatttag atgacagttt taaaactcag   1320
tttgcagcct taggaggatg ggtttgcat cagccacctc ctcaaatatt tttaaaaata   1380
```

```
ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga atcctcaacc tggagtatat ccccgcacg cagcaggtca tttaccatat     1560
gtactatatg accctacagc tacagatgca aaacaacacc acagacatgg atatgaaaag    1620
cctgaagaat tgtggacagc caaaagccgt gtgcacccat tgtaa                   1665
```

<210> SEQ ID NO 11
<211> LENGTH: 1665
<212> TYPE: DNA
<213> ORGANISM: Artificial Sequence
<220> FEATURE:
<223> OTHER INFORMATION: Construct I

<400> SEQUENCE: 11

```
atgacttcag ttaattctgc agaagccagc actggtgcag gagggggggg cagtaatcct    60
gtcaaaagca tgtggagtga gggggccact tttagtgcca actctgtgac ttgtacattt    120
tctagacagt ttttaattcc atatgaccca gagcaccatt ataaggtgtt ttctcccgca    180
gcaagtagct gccacaatgc cagtggaaag gaggcaaagg tttgcaccat tagtcccata    240
atgggatact caaccccatg gagatattta gattttaatg ctttaaactt attttttca    300 cctttagagt ttcagcactt aattgaaaat tatggaagta tagctcctga tgctttaact    360
gtaaccatat cagaaattgc tgttaaggat gttacagaca aaactggagg ggggggtgcag   420 gttactgaca gcactacagg gcgcctatgc atgttagtag accatgaata caagtaccca    480
tatgtgttag ggcaaggtca agatacttta gccccagaac ttcctatttg ggtatacttt    540
ccccctcaat atgcttactt aacagtagga gatgttaaca cacaaggaat ttctggagac    600
agcaaaaaat tagcaagtga agaatcagca ttttatgttt tggaacacag ttcttttcag    660
cttttaggta caggaggtac agcaactatg tcttataagt ttcctccagt gcccccagaa    720
aatttagagg gctgcagtca acacttttat gagatgtaca atcccttata cggatcccgc    780
ttaggggttc ctgacacatt aggaggtgac ccaaaattta gatctttaac acatgaagac    840
catgcaattc agccccaaaa cttcatgcca gggccactag taaactcagt gtctacaaag    900
gagggagaca gctctaatac tggagctggg aaagccttaa caggccttag cacaggtacc    960
tctcaaaaca ctagaatatc cttacgcccg gggccagtgt ctcagccgta ccaccactgg   1020
gacacagata aatatgtcac aggaataaat gctatttctc atggtcagac cacttatggt   1080
aacgctgaag acaaagagta tcagcaagga gtgggtagat ttccaaatga aaaagaacag   1140
ctaaaacagt tacagggttt aaacatgcac acctttttc ccaataaagg aacccagcaa   1200
tatacagatc aaattgagcg ccccctaatg gtgggttctg tatggaacag aagagccctt   1260
cactatgaaa gccagctgtg gagtaaaatt ccaaatttag atgacagttt taaaactcag    1320
tttgcagcct taggaggatg gggtttgcat cagccacctc tcaaatatt tttaaaaata    1380 ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga atcctcaacc tggagtatat ccccgcacg cagcaggtca tttaccatat     1560
gtactatatg accctacagc tacagatgca aaacaacacc acagacatgg atatgaaaag    1620
cctgaagaat tgtggacagc caaaagccgt gtgcacccat tgtaa                   1665
```

<210> SEQ ID NO 12

<211> LENGTH: 1665
<212> TYPE: DNA
<213> ORGANISM: Artificial Sequence
<220> FEATURE:
<223> OTHER INFORMATION: Construct J

<400> SEQUENCE: 12

| | | | | | |
|---|---|---|---|---|---|
| atgacttcag | ttaattctgc | agaagccagc | actggtgcag | gagggggggg | cagtaatcct | 60 |
| gtcaaaagca | tgtggagtga | gggggccact | tttagtgcca | actctgtgac | ttgtacattt | 120 |
| tctagacagt | ttttaattcc | atatgaccca | gagcaccatt | ataaggtgtt | ttctcccgca | 180 |
| gcaagtagct | gccacaatgc | cagtggaaag | gaggcaaagg | tttgcaccat | tagtcccata | 240 |
| atgggatact | caaccccatg | gagatattta | gattttaatg | ctttaaactt | attttttca | 300 |
| cctttagagt | ttcagcactt | aattgaaaat | tatggaagta | tagctcctga | tgctttaact | 360 |
| gtaaccatat | cagaaattgc | tgttaaggat | gttacagaca | aaactggagg | ggggggtgcag | 420 |
| gttactgaca | gcactacagg | gcgcctatgc | atgttagtag | accatgaata | caagtaccca | 480 |
| tatgtgttag | gcaaggtca | agatacttta | gccccagaac | ttcctatttg | ggtatacttt | 540 |
| cccctcaat | atgcttactt | aacagtagga | gatgttaaca | cacaaggaat | ttctggagac | 600 |
| agcaaaaat | tagcaagtga | agaatcagca | ttttatgttt | tggaacacag | ttcttttcag | 660 |
| cttttaggta | caggaggtac | agcaactatg | tcttataagt | ttcctccagt | gcccccagaa | 720 |
| aatttagagg | gctgcagtca | acactttat | gagatgtaca | atcccttata | cggatcccgc | 780 |
| ttaggggttc | ctgacacatt | aggaggtgac | ccaaaattta | gatctttaac | acatgaagac | 840 |
| catgcaattc | agccccaaaa | cttcatgcca | gggccactag | taaactcagt | gtctacaaag | 900 |
| gagggagaca | gctctaatac | tggagctggg | aaagccttaa | caggccttag | cacaggtacc | 960 |
| tctcaaaaca | ctagaatatc | cttacgcccg | gggccagtgt | ctcagccgta | ccaccactgg | 1020 |
| gacacagata | aatatgtcac | aggaataaat | gctatttctc | atggtcagac | cacttatggt | 1080 |
| aacgctgaag | acaaagagta | tcagcaagga | gtgggtagat | tccaaatga | aaagaacag | 1140 |
| ctaaaacagt | tacagggttt | aaacatgcac | acctactttc | ccaataaagg | aaccaacaac | 1200 |
| tttacagata | acattgagcg | cccccctaatg | gtgggttctg | tatggaacag | aagagccctt | 1260 |
| cactatgaaa | gccagctgtg | gagtaaaatt | ccaaatttag | atgacagttt | taaaactcag | 1320 |
| tttgcagcct | taggaggatg | gggttttgcat | cagccacctc | ctcaaatatt | tttaaaaata | 1380 |
| ttaccacaaa | gtgggccaat | tggaggtatt | aaatcaatgg | gaattactac | cttagttcag | 1440 |
| tatgccgtgg | gaattatgac | agtaaccatg | acatttaaat | tggggccccg | taaagctacg | 1500 |
| ggacggtgga | atcctcaacc | tggagtatat | cccccgcacg | cagcaggtca | tttaccatat | 1560 |
| gtactatatg | accctacagc | tacagatgca | aaacaacacc | acagacatgg | atatgaaaag | 1620 |
| cctgaagaat | tgtggacagc | caaaagccgt | gtgcacccat | tgtaa | | 1665 |

<210> SEQ ID NO 13
<211> LENGTH: 1665
<212> TYPE: DNA
<213> ORGANISM: Artificial Sequence
<220> FEATURE:
<223> OTHER INFORMATION: Construct K

<400> SEQUENCE: 13

| | | | | | |
|---|---|---|---|---|---|
| atgacttcag | ttaattctgc | agaagccagc | actggtgcag | gagggggggg | cagtaatcct | 60 |
| gtcaaaagca | tgtggagtga | gggggccact | tttagtgcca | actctgtgac | ttgtacattt | 120 |
| tctagacagt | ttttaattcc | atatgaccca | gagcaccatt | ataaggtgtt | ttctcccgca | 180 |

```
gcaagtagct gccacaatgc cagtggaaag gaggcaaagg tttgcaccat tagtcccata      240
atgggatact caaccccatg gagatattta gattttaatg ctttaaactt attttttca      300 cctttagagt ttcagcactt aattgaaaat tatggaagta tagctcctga tgctttaact      360
gtaaccatat cagaaattgc tgttaaggat gttacagaca aaactggagg ggggtgcag      420 gttactgaca gcactacagg gcgcctatgc atgttagtag accatgaata caagtaccca      480
tatgtgttag ggcaaggtca agatacttta gccccagaac ttcctatttg ggtatacttt      540 cccctcaat atgcttactt aacagtagga gatgttaaca cacaaggaat tctggagac      600 agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca cacttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tcagcaagga gtgggtagat tcccaaatga aaagaacag     1140 ctaaaacagt tacagggttt aaacatgcac acctactttc ccaataaagg aaccaacaac     1200
tatacagata acattgagcg cccctaatg gtgggttctg tatggaacag aagagccctt     1260
cactatgaaa gccagctgtg gagtaaaatt ccaaatttag atgacagttt taaaactcag     1320
tttgcagcct taggaggatg gggtttgcat cagccacctc ctcaaatatt tttaaaata      1380 ttaccacaaa gtgggccaat tggaggtatt aaatcaatgg gaattactac cttagttcag     1440
tatgccgtgg gaattatgac agtaaccatg acatttaaat tggggccccg taaagctacg     1500
ggacggtgga atcctcaacc tggagtatat cccccgcacg cagcaggtca tttaccatat     1560
gtactatatg accctacagc tacagatgca aaacaacacc acagacatgg atatgaaaag     1620
cctgaagaat tgtggacagc caaaagccgt gtgcacccat tgtaa                    1665

<210> SEQ ID NO 14
<211> LENGTH: 1677
<212> TYPE: DNA
<213> ORGANISM: Artificial Sequence
<220> FEATURE:
<223> OTHER INFORMATION: Construct L

<400> SEQUENCE: 14
atgacttcag ttaattctgc agaagccagc actggtgcag agggggggg cagtaatcct       60 gtcaaaagca tgtggagtga gggggccact tttagtgcca actctgtgac ttgtacattt      120
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt attttttca      300 cctttagagt ttcagcactt aattgaaaat tatggaagta tagctcctga tgctttaact      360
gtaaccatat cagaaattgc tgttaaggat gttacagaca aaactggagg ggggtgcag      420 gttactgaca gcactacagg gcgcctatgc atgttagtag accatgaata caagtaccca      480
tatgtgttag ggcaaggtca agatacttta gccccagaac ttcctatttg ggtatacttt      540
```

```
ccccctcaat atgcttactt aacagtagga gatgttaaca cacaaggaat ttctggagac      600
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca cacttttat gagatgtaca atcccttata cggatcccgc       780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tcagcaagga gtgggtagat tcccaaatga aaagaacag      1140 ctaaaacagt tacagggttt aaacatgcac acctactttc ccaataaagg aacccagcaa     1200
tatacagatc aagatccaat tggtattgag cgccccctaa tggtgggttc tgtatggaac     1260
agaagagccc ttcactatga aagccagctg tggagtaaaa ttccaaattt agatgacagt     1320
tttaaaactc agtttgcagc cttaggagga tggggtttgc atcagccacc tcctcaaata     1380 ttttttaaaaa tattaccaca aagtgggcca attggaggta ttaaatcaat gggaattact     1440
accttagttc agtatgccgt gggaattatg acagtaacca tgacatttaa attggggccc     1500
cgtaaagcta cgggacggtg gaatcctcaa cctggagtat atccccccgca cgcagcaggt     1560 catttaccat atgtactata tgaccctaca gctacagatg caaaacaaca ccacagacat     1620
ggatatgaaa agcctgaaga attgtggaca gccaaaagcc gtgtgcaccc attgtaa       1677

<210> SEQ ID NO 15
<211> LENGTH: 1665
<212> TYPE: DNA
<213> ORGANISM: Artificial Sequence
<220> FEATURE:
<223> OTHER INFORMATION: Construct M

<400> SEQUENCE: 15
atgacttcag ttaattctgc agaagccagc actggtgcag aggggggggg cagtaatcct        60
gtcaaaagca tgtggagtga gggggccact tttagtgcca actctgtgac ttgtacattt       120
tctagacagt ttttaattcc atatgaccca gagcaccatt ataaggtgtt ttctcccgca       180
gcaagtagct gccacaatgc cagtggaaag gaggcaaagg tttgcaccat tagtcccata       240
atgggatact caaccccatg gagatattta gattttaatg ctttaaactt attttttca       300 cctttagagt ttcagcactt aattgaaaat tatggaagta tagctcctga tgctttaact       360
gtaaccatat cagaaattgc tgttaaggat gttacagaca aaactggagg ggggtgcag       420 gttactgaca gcactacagg gcgcctatgc atgttagtag accatgaata caagtaccca       480
tatgtgttag gcaaggtca agatacttta gccccagaac ttcctatttg ggtatacttt       540 cccctcaat atgcttactt aacagtagga gatgttaaca cacaaggaat ttctggagac       600
agcaaaaaat tagcaagtga agaatcagca ttttatgttt tggaacacag ttcttttcag       660
cttttaggta caggaggtac agcaactatg tcttataagt ttcctccagt gcccccagaa       720
aatttagagg gctgcagtca cacttttat gagatgtaca atcccttata cggatcccgc        780
ttaggggttc ctgacacatt aggaggtgac ccaaaattta gatctttaac acatgaagac       840
catgcaattc agccccaaaa cttcatgcca gggccactag taaactcagt gtctacaaag       900
gagggagaca gctctaatac tggagctggg aaagccttaa caggccttag cacaggtacc       960
```

| | |
|---|---|
| tctcaaaaca ctagaatatc cttacgcccg gggccagtgt ctcagccgta ccaccactgg | 1020 |
| gacacagata aatatgtcac aggaataaat gctatttctc atggtcagac cacttatggt | 1080 |
| aacgctgaag acaaagagta tcagcaagga gtgggtagat ttccaaatga aaaagaacag | 1140 |
| ctaaaacagt tacagggttt aaacatgcac acctactttc ccaataaagg aaccgctgct | 1200 |
| tatacagatc aaattgagcg ccccctaatg gtgggttctg tatggaacag aagagccctt | 1260 |
| cactatgaaa gccagctgtg gagtaaaatt ccaaatttag atgacagttt taaaactcag | 1320 |
| tttgcagcct taggaggatg gggtttgcat cagccacctc ctcaaatatt tttaaaaata | 1380 |
| ttaccacaaa gtgggccaat tggaggtatt aaatcaatgg gaattactac cttagttcag | 1440 |
| tatgccgtgg aattatgac agtaaccatg acatttaaat tggggccccg taaagctacg | 1500 |
| ggacggtgga atcctcaacc tggagtatat ccccgcacg cagcaggtca tttaccatat | 1560 |
| gtactatatg accctacagc tacagatgca aaacaacacc acagacatgg atatgaaaag | 1620 |
| cctgaagaat tgtggacagc caaaagccgt gtgcacccat tgtaa | 1665 |

```
<210> SEQ ID NO 16
<211> LENGTH: 1665
<212> TYPE: DNA
<213> ORGANISM: Artificial Sequence
<220> FEATURE:
<223> OTHER INFORMATION: Construct N

<400> SEQUENCE: 16
```

| | |
|---|---|
| atgacttcag ttaattctgc agaagccagc actggtgcag aggggggggg cagtaatcct | 60 |
| gtcaaaagca tgtggagtga gggggccact tttagtgcca actctgtgac ttgtacattt | 120 |
| tctagacagt tttaattcc atatgaccca gagcaccatt ataaggtgtt ttctcccgca | 180 |
| gcaagtagct gccacaatgc cagtggaaag gaggcaaagg tttgcaccat tagtcccata | 240 |
| atgggatact caaccccatg gagatattta gattttaatg ctttaaactt atttttttca | 300 |
| cctttagagt ttcagcactt aattgaaaat tatggaagta tagctcctga tgctttaact | 360 |
| gtaaccatat cagaaattgc tgttaaggat gttacagaca aaactggagg ggggtgcag | 420 |
| gttactgaca gcactacagg gcgcctatgc atgttagtag accatgaata caagtaccca | 480 |
| tatgtgttag gcaaggtca agatacttta gccccagaac ttcctatttg ggtatacttt | 540 |
| cccccctcaat atgcttactt aacagtagga gatgttaaca cacaaggaat ttctggagac | 600 |
| agcaaaaaat tagcaagtga agaatcagca ttttatgttt tggaacacag ttcttttcag | 660 |
| cttttaggta caggaggtac agcaactatg tcttataagt ttcctccagt gcccccagaa | 720 |
| aatttagagg gctgcagtca acacttttat gagatgtaca atcccttata cggatcccgc | 780 |
| ttaggggttc ctgacacatt aggaggtgac ccaaaattta gatctttaac acatgaagac | 840 |
| catgcaattc agcccccaaaa cttcatgcca gggccactag taaactcagt gtctacaaag | 900 |
| gagggagaca gctctaatac tggagctggg aaagccttaa caggccttag cacaggtacc | 960 |
| tctcaaaaca ctagaatatc cttacgcccg gggccagtgt ctcagccgta ccaccactgg | 1020 |
| gacacagata aatatgtcac aggaataaat gctatttctc atggtcagac cacttatggt | 1080 |
| aacgctgaag acaaagagta tcagcaagga gtgggtagat ttccaaatga aaaagaacag | 1140 |
| ctaaaacagt tacagggttt aaacatgcac acctactttc ccaataaagg aacccaacaa | 1200 |
| ccagctgcac aaattgagcg ccccctaatg gtgggttctg tatggaacag aagagccctt | 1260 |
| cactatgaaa gccagctgtg gagtaaaatt ccaaatttag atgacagttt taaaactcag | 1320 |

| | |
|---|---|
| tttgcagcct taggaggatg gggtttgcat cagccacctc ctcaaatatt tttaaaaata | 1380 |
| ttaccacaaa gtgggccaat tggaggtatt aaatcaatgg gaattactac cttagttcag | 1440 |
| tatgccgtgg gaattatgac agtaaccatg acatttaaat tggggccccg taaagctacg | 1500 |
| ggacggtgga atcctcaacc tggagtatat ccccgcacg cagcaggtca tttaccatat | 1560 |
| gtactatatg accctacagc tacagatgca aaacaacacc acagacatgg atatgaaaag | 1620 |
| cctgaagaat tgtggacagc caaaagccgt gtgcacccat tgtaa | 1665 |

<210> SEQ ID NO 17
<211> LENGTH: 1665
<212> TYPE: DNA
<213> ORGANISM: Artificial Sequence
<220> FEATURE:
<223> OTHER INFORMATION: Construct O

<400> SEQUENCE: 17

| | |
|---|---|
| atgacttcag ttaattctgc agaagccagc actggtgcag agggggggg cagtaatcct | 60 |
| gtcaaaagca tgtggagtga gggggccact tttagtgcca actctgtgac ttgtacattt | 120 |
| tctagacagt tttaattcc atatgaccca gagcaccatt ataaggtgtt ttctcccgca | 180 |
| gcaagtagct gccacaatgc cagtggaaag gaggcaaagg tttgcaccat tagtcccata | 240 |
| atgggatact caaccccatg gagatattta gattttaatg ctttaaactt attttttca | 300 |
| cctttagagt ttcagcactt aattgaaaat tatggaagta tagctcctga tgctttaact | 360 |
| gtaaccatat cagaaattgc tgttaaggat gttacagaca aaactggagg ggggtgcag | 420 |
| gttactgaca gcactacagg gcgcctatgc atgttagtag accatgaata caagtaccca | 480 |
| tatgtgttag ggcaaggtca agatacttta gccccagaac ttcctatttg ggtatacttt | 540 |
| ccccctcaat atgcttactt aacagtagga gatgttaaca cacaaggaat ttctggagac | 600 |
| agcaaaaaat tagcaagtga agaatcagca ttttatgttt tggaacacag ttcttttcag | 660 |
| cttttaggta caggaggtac agcaactatg tcttataagt ttcctccagt gcccccagaa | 720 |
| aatttagagg gctgcagtca acactttat gagatgtaca atcccttata cggatcccgc | 780 |
| ttaggggttc ctgacacatt aggaggtgac ccaaaattta gatctttaac acatgaagac | 840 |
| catgcaattc agccccaaaa cttcatgcca gggccactag taaactcagt gtctacaaag | 900 |
| gagggagaca gctctaatac tggagctggg aaagccttaa caggccttag cacaggtacc | 960 |
| tctcaaaaca ctagaatatc cttacgcccg gggccagtgt ctcagccgta ccaccactgg | 1020 |
| gacacagata aatatgtcac aggaataaat gctatttctc atggtcagac cacttatggt | 1080 |
| aacgctgaag acaaagagta tcagcaagga gtgggtagat tccaaatga aaagaacag | 1140 |
| ctaaaacagt tacagggttt aaacatgcac acctactttc ccaataaagg aaccaacaac | 1200 |
| tggacagata ccattgagcg ccccctaatg gtgggttctg tatggaacag aagagccctt | 1260 |
| cactatgaaa gccagctgtg gagtaaaatt ccaaatttag atgacagttt taaaactcag | 1320 |
| tttgcagcct taggaggatg gggtttgcat cagccacctc ctcaaatatt tttaaaaata | 1380 |
| ttaccacaaa gtgggccaat tggaggtatt aaatcaatgg gaattactac cttagttcag | 1440 |
| tatgccgtgg gaattatgac agtaaccatg acatttaaat tggggccccg taaagctacg | 1500 |
| ggacggtgga atcctcaacc tggagtatat ccccgcacg cagcaggtca tttaccatat | 1560 |
| gtactatatg accctacagc tacagatgca aaacaacacc acagacatgg atatgaaaag | 1620 |
| cctgaagaat tgtggacagc caaaagccgt gtgcacccat tgtaa | 1665 |

<210> SEQ ID NO 18
<211> LENGTH: 1665
<212> TYPE: DNA
<213> ORGANISM: Artificial Sequence
<220> FEATURE:
<223> OTHER INFORMATION: Construct P

<400> SEQUENCE: 18

| | | | | | |
|---|---|---|---|---|---|
| atgacttcag | ttaattctgc | agaagccagc | actggtgcag | gagggggggg | cagtaatcct | 60 |
| gtcaaaagca | tgtggagtga | gggggccact | tttagtgcca | actctgtgac | ttgtacattt | 120 |
| tctagacagt | ttttaattcc | atatgaccca | gagcaccatt | ataaggtgtt | ttctcccgca | 180 |
| gcaagtagct | gccacaatgc | cagtggaaag | gaggcaaagg | tttgcaccat | tagtcccata | 240 |
| atgggatact | caaccccatg | gagatattta | gattttaatg | ctttaaactt | atttttttca | 300 |
| cctttagagt | ttcagcactt | aattgaaaat | tatggaagta | tagctcctga | tgctttaact | 360 |
| gtaaccatat | cagaaattgc | tgttaaggat | gttacagaca | aaactggagg | ggggtgcag  | 420 |
| gttactgaca | gcactacagg | gcgcctatgc | atgttagtag | accatgaata | caagtaccca | 480 |
| tatgtgttag | ggcaaggtca | agatacttta | gccccagaac | ttcctatttg | ggtatacttt | 540 |
| cccccctcaat | atgcttactt | aacagtagga | gatgttaaca | cacaaggaat | ttctggagac | 600 |
| agcaaaaaat | tagcaagtga | agaatcagca | ttttatgttt | tggaacacag | ttcttttcag | 660 |
| cttttaggta | caggaggtac | agcaactatg | tcttataagt | ttcctccagt | gcccccagaa | 720 |
| aatttagagg | gctgcagtca | acactttat  | gagatgtaca | atcccttata | cggatcccgc | 780 |
| ttaggggttc | ctgacacatt | aggaggtgac | ccaaaattta | gatctttaac | acatgaagac | 840 |
| catgcaattc | agccccaaaa | cttcatgcca | gggccactag | taaactcagt | gtctacaaag | 900 |
| gagggagaca | gctctaatac | tggagctggg | aaagccttaa | caggccttag | cacaggtacc | 960 |
| tctcaaaaca | ctagaatatc | cttacgcccg | gggccagtgt | ctcagccgta | ccaccactgg | 1020 |
| gacacagata | aatatgtcac | aggaataaat | gctatttctc | atggtcagac | cacttatggt | 1080 |
| aacgctgaag | acaaagagta | tcagcaagga | gtgggtagat | ttccaaatga | aaagaacag  | 1140 |
| ctaaaacagt | tacagggttt | aaacatgcac | accgcttttc | ccaataaagg | aaccaacaac | 1200 |
| tggacagata | ccattgagcg | cccccctaatg | gtgggttctg | tatggaacag | aagagccctt | 1260 |
| cactatgaaa | gccagctgtg | gagtaaaatt | ccaaatttag | atgacagttt | taaaactcag | 1320 |
| tttgcagcct | taggaggatg | gggttttgcat | cagccacctc | ctcaaatatt | tttaaaaata | 1380 |
| ttaccacaaa | gtgggccaat | tggaggtatt | aaatcaatgg | gaattactac | cttagttcag | 1440 |
| tatgccgtgg | gaattatgac | agtaaccatg | acatttaaat | ggggccccg  | taaagctacg | 1500 |
| ggacggtgga | atcctcaacc | tggagtatat | ccccgcacg  | cagcaggtca | tttaccatat | 1560 |
| gtactatatg | accctacagc | tacagatgca | aaacaacacc | acagacatgg | atatgaaaag | 1620 |
| cctgaagaat | tgtggacagc | caaaagccgt | gtgcacccat | tgtaa | | 1665 |

<210> SEQ ID NO 19
<211> LENGTH: 1665
<212> TYPE: DNA
<213> ORGANISM: Artificial Sequence
<220> FEATURE:
<223> OTHER INFORMATION: Construct Q

<400> SEQUENCE: 19

| | | | | | |
|---|---|---|---|---|---|
| atgacttcag | ttaattctgc | agaagccagc | actggtgcag | gagggggggg | cagtaatcct | 60 |
| gtcaaaagca | tgtggagtga | gggggccact | tttagtgcca | actctgtgac | ttgtacattt | 120 |

```
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt attttttca      300 cctttagagt ttcagcactt aattgaaaat tatggaagta tagctcctga tgctttaact      360
gtaaccatat cagaaattgc tgttaaggat gttacagaca aaactggagg gggggtgcag      420
gttactgaca gcactacagg gcgcctatgc atgttagtag accatgaata caagtaccca      480
tatgtgttag ggcaaggtca agatacttta gccccagaac ttcctatttg ggtatacttt      540 cccctcaat atgcttactt aacagtagga gatgttaaca cacaaggaat ttctggagac      600
agcaaaaaat tagcaagtga agaatcagca ttttatgttt tggaacacag ttcttttcag      660 ctttaggta caggaggtac agcaactatg tcttataagt ttcctccagt gcccccagaa      720
aatttagagg gctgcagtca cacttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg ggccagtgt ctcagccgta ccaccactgg      1020
gacacagata aatatgtcac aggaataaat gctatttctc atggtcagac cacttatggt      1080
aacgctgaag acaaagagta tgctgctgga gtgggtagat ttccaaatga aaagaacag      1140 ctaaaacagt tacagggttt aaacatgcac acctactttc ccaataaagg aacccagcaa      1200
tttacagatc aaattgagcg ccccctaatg gtgggttctg tatggaacag aagagccctt      1260
cactatgaaa gccagctgtg gagtaaaatt ccaaatttag atgacagttt taaaactcag      1320
tttgcagcct taggaggatg gggttttgcat cagccacctc ctcaaatatt tttaaaaata      1380
ttaccacaaa gtgggccaat tggaggtatt aaatcaatgg gaattactac cttagttcag      1440
tatgccgtgg gaattatgac agtaaccatg acatttaaat ggggccccg taaagctacg      1500 ggacggtgga atcctcaacc tggagtatat cccccgcacg cagcaggtca tttaccatat      1560
gtactatatg accctacagc tacagatgca aaacaacacc acagacatgg atatgaaaag      1620
cctgaagaat tgtggacagc caaaagccgt gtgcacccat tgtaa                     1665
```

<210> SEQ ID NO 20
<211> LENGTH: 1665
<212> TYPE: DNA
<213> ORGANISM: Artificial Sequence
<220> FEATURE:
<223> OTHER INFORMATION: Construct R

<400> SEQUENCE: 20

```
atgacttcag ttaattctgc agaagccagc actggtgcag agggggggg cagtaatcct      60 gtcaaaagca tgtggagtga gggggccact tttagtgcca actctgtgac ttgtacattt      120
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt attttttca      300 cctttagagt ttcagcactt aattgaaaat tatggaagta tagctcctga tgctttaact      360
gtaaccatat cagaaattgc tgttaaggat gttacagaca aaactggagg gggggtgcag      420
gttactgaca gcactacagg gcgcctatgc atgttagtag accatgaata caagtaccca      480
tatgtgttag ggcaaggtca agatacttta gccccagaac ttcctatttg ggtatacttt      540
```

```
ccccctcaat atgcttactt aacagtagga gatgttaaca cacaaggaat ttctggagac      600
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca cactttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tgctgctgga gtgggtagat tccaaatgaa aaagaacag      1140 ctaaaacagt tacagggttt aaacatgcac acctactttc ccaataaagg aaccaacaac     1200
tttacagata ccattgagcg ccccctaatg gtgggttctg tatggaacag aagagccctt     1260
cactatgaaa gccagctgtg gagtaaaatt ccaaatttag atgacagttt taaaactcag     1320
tttgcagcct taggaggatg gggttttgcat cagccaccctc ctcaaatatt ttaaaaata     1380 ttaccacaaa gtgggccaat tggaggtatt aaatcaatgg gaattactac cttagttcag     1440
tatgccgtgg gaattatgac agtaaccatg acatttaaat tggggccccg taaagctacg     1500
ggacggtgga atcctcaacc tggagtatat cccccgcacg cagcaggtca tttaccatat     1560
gtactatatg accctacagc tacagatgca aaacaacacc acagacatgg atatgaaaag     1620
cctgaagaat tgtggacagc caaaagccgt gtgcacccat tgtaa                     1665
```

<210> SEQ ID NO 21
<211> LENGTH: 1665
<212> TYPE: DNA
<213> ORGANISM: Artificial Sequence
<220> FEATURE:
<223> OTHER INFORMATION: Construct S

<400> SEQUENCE: 21

```
atgacttcag ttaattctgc agaagccagc actggtgcag agggggggg cagtaatcct       60 gtcaaaagca tgtggagtga gggggccact tttagtgcca actctgtgac ttgtacattt      120
tctagacagt tttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt attttttttca     300 cctttagagt ttcagcactt aattgaaaat tatggaagta tagctcctga tgctttaact     360
gtaaccatat cagaaattgc tgttaaggat gttacagaca aaactggagg gggggtgcag     420
gttactgaca gcactacagg gcgcctatgc atgttagtag accatgaata caagtaccca     480
tatgtgttag gcaaggtca agatacttta gccccagaac ttcctatttg gtatactttt      540 cccctcaat atgcttactt aacagtagga gatgttaaca cacaaggaat ttctggagac      600
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca cactttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
```

```
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tcagcaagga gtgggtagat tccaaatga aaaagaacag     1140 ctaaaacagt tacagggttt aaacatgcac accgcttttc ccaataaagg aacccagcaa     1200
tggacagatc aaattgagcg ccccctaatg gtgggttctg tatggaacag aagagccctt     1260
cactatgaaa gccagctgtg gagtaaaatt ccaaatttag atgacagttt taaaactcag     1320
tttgcagcct taggaggatg gggtttgcat cagccacctc ctcaaatatt tttaaaaata     1380
ttaccacaaa gtgggccaat ggaggtatt aaatcaatgg gaattactac cttagttcag      1440
tatgccgtgg gaattatgac agtaaccatg acatttaaat tggggccccg taaagctacg     1500
ggacggtgga atcctcaacc tggagtatat cccccgcacg cagcaggtca tttaccatat     1560
gtactatatg accctacagc tacagatgca aaacaacacc acagacatgg atatgaaaag     1620
cctgaagaat tgtggacagc caaaagccgt gtgcacccat tgtaa                     1665

<210> SEQ ID NO 22
<211> LENGTH: 1665
<212> TYPE: DNA
<213> ORGANISM: Artificial Sequence
<220> FEATURE:
<223> OTHER INFORMATION: Construct T

<400> SEQUENCE: 22
atgacttcag ttaattctgc agaagccagc actggtgcag aggggggggg cagtaatcct       60
gtcaaaagca tgtggagtga gggggccact tttagtgcca actctgtgac ttgtacattt      120
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg cttttaaactt attttttttca    300 ccttttagagt ttcagcactt aattgaaaat tatggaagta tagctcctga tgctttaact     360
gtaaccatat cagaaattgc tgttaaggat gttacagaca aaactggagg gggggtgcag     420
gttactgaca gcactacagg gcgcctatgc atgttagtag accatgaata caagtaccca      480
tatgtgttag gcaaggtca agatacttta gccccagaac ttcctatttg ggtatacttt      540
ccccctcaat atgcttactt aacagtagga gatgttaaca cacaaggaat tctggagac      600 agcaaaaaat tagcaagtga agaatcagca ttttatgttt tggaacacag ttcttttcag     660
cttttaggta caggaggtac agcaactatg tcttataagt ttcctccagt gcccccagaa      720
aatttagagg gctgcagtca cactttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tgctgctgga gtgggtagat tccaaatga aaaagaacag     1140 ctaaaacagt tacagggttt aaacatgcac accgcttttc ccaataaagg aaccaacaac     1200
tggacagata ccattgagcg ccccctaatg gtgggttctg tatggaacag aagagccctt     1260
cactatgaaa gccagctgtg gagtaaaatt ccaaatttag atgacagttt taaaactcag     1320
```

```
tttgcagcct taggaggatg gggtttgcat cagccacctc ctcaaatatt tttaaaaata   1380
ttaccacaaa gtgggccaat tggaggtatt aaatcaatgg gaattactac cttagttcag   1440
tatgccgtgg gaattatgac agtaaccatg acatttaaat tggggccccg taaagctacg   1500
ggacggtgga atcctcaacc tggagtatat cccccgcacg cagcaggtca tttaccatat   1560
gtactatatg accctacagc tacagatgca aaacaacacc acagacatgg atatgaaaag   1620
cctgaagaat tgtggacagc caaaagccgt gtgcacccat tgtaa                   1665

<210> SEQ ID NO 23
<211> LENGTH: 1665
<212> TYPE: DNA
<213> ORGANISM: Artificial Sequence
<220> FEATURE:
<223> OTHER INFORMATION: Construct U

<400> SEQUENCE: 23
atgacttcag ttaattctgc agaagccagc actggtgcag gagggggggg cagtaatcct     60
gtcaaaagca tgtggagtga ggggccact tttagtgcca actctgtgac ttgtacattt     120
tctagacagt tttaattcc atatgaccca gagcaccatt ataaggtgtt ttctcccgca     180
gcaagtagct gccacaatgc cagtggaaag gaggcaaagg tttgcaccat tagtcccata    240
atgggatact caaccccatg gagatattta gattttaatg ctttaaactt atttttttca    300
cctttagagt ttcagcactt aattgaaaat tatgaagta tagctcctga tgctttaact     360
gtaaccatat cagaaattgc tgttaaggat gttacagaca aaactggagg ggggtgcag     420 gttactgaca gcactacagg gcgcctatgc atgttagtag accatgaata caagtaccca    480
tatgtgttag gcaaggtca agatacttta gccccagaac ttcctatttg ggtatacttt     540 cccccctcaat atgcttactt aacagtagga gatgttaaca cacaaggaat ttctggagac    600
agcaaaaaat tagcaagtga agaatcagca ttttatgttt ggaacacag ttcttttcag     660 cttttaggta caggaggtac agcaactatg tcttataagt ttcctccagt gcccccagaa   720
aatttagagg gctgcagtca acactttat gagatgtaca atcccttata cggatcccgc    780
ttaggggttc ctgacacatt aggaggtgac ccaaaattta gatctttaac acatgaagac   840
catgcaattc agccccaaaa cttcatgcca gggccactag taaactcagt gtctacaaag    900
gagggagaca gctctaatac tggagctggg aaagccttaa caggcttag cacaggtacc    960 tctcaaaaca ctagaatatc cttacgcccg gggccagtgt ctcagccgta ccaccactgg   1020
gacacagata aatatgtcac aggaataaat gctatttctc atggtcagac cacttatggt   1080
aacgctgaag acaaagagta tgctgctgga gtgggtagat ttccaaatga aaagaacag    1140 ctaaaacagt tacagggttt aaacatgcac accgcttttc ccaataaagg aacccagcaa   1200
tttacagatc aaattgagcg ccccctaatg gtgggttctg tatggaacag aagagccctt   1260
cactatgaaa gccagctgtg gagtaaaatt ccaaatttag atgacagttt taaaactcag   1320
tttgcagcct taggaggatg gggtttgcat cagccacctc ctcaaatatt tttaaaaata   1380
ttaccacaaa gtgggccaat tggaggtatt aaatcaatgg gaattactac cttagttcag   1440
tatgccgtgg gaattatgac agtaaccatg acatttaaat tggggccccg taaagctacg   1500
ggacggtgga atcctcaacc tggagtatat cccccgcacg cagcaggtca tttaccatat   1560
gtactatatg accctacagc tacagatgca aaacaacacc acagacatgg atatgaaaag   1620
cctgaagaat tgtggacagc caaaagccgt gtgcacccat tgtaa                   1665
```

<210> SEQ ID NO 24
<211> LENGTH: 1665
<212> TYPE: DNA
<213> ORGANISM: Artificial Sequence
<220> FEATURE:
<223> OTHER INFORMATION: Construct V

<400> SEQUENCE: 24

| | | | | | |
|---|---|---|---|---|---|
| atgacttcag | ttaattctgc | agaagccagc | actggtgcag | gagggggggg | cagtaatcct | 60 |
| gtcaaaagca | tgtggagtga | gggggccact | tttagtgcca | actctgtgac | ttgtacattt | 120 |
| tctagacagt | ttttaattcc | atatgaccca | gagcaccatt | ataaggtgtt | ttctcccgca | 180 |
| gcaagtagct | gccacaatgc | cagtggaaag | gaggcaaagg | tttgcaccat | tagtcccata | 240 |
| atgggatact | caaccccatg | gagatattta | gattttaatg | ctttaaactt | attttttca | 300 |
| cctttagagt | ttcagcactt | aattgaaaat | tatggaagta | tagctcctga | tgctttaact | 360 |
| gtaaccatat | cagaaattgc | tgttaaggat | gttacagaca | aaactggagg | ggggtgcag | 420 |
| gttactgaca | gcactacagg | gcgcctatgc | atgttagtag | accatgaata | caagtaccca | 480 |
| tatgtgttag | ggcaaggtca | agatacttta | gccccagaac | ttcctatttg | ggtatacttt | 540 |
| cccctcaat | atgcttactt | aacagtagga | gatgttaaca | cacaaggaat | ttctggagac | 600 |
| agcaaaaaat | tagcaagtga | agaatcagca | ttttatgttt | tggaacacag | ttcttttcag | 660 |
| cttttaggta | caggaggtac | agcaactatg | tcttataagt | ttcctccagt | gcccccagaa | 720 |
| aatttagagg | gctgcagtca | acactttat | gagatgtaca | atcccttata | cggatcccgc | 780 |
| ttaggggttc | ctgacacatt | aggaggtgac | ccaaaattta | gatctttaac | acatgaagac | 840 |
| catgcaattc | agccccaaaa | cttcatgcca | gggccactag | taaactcagt | gtctacaaag | 900 |
| gagggagaca | gctctaatac | tggagctggg | aaagccttaa | caggccttag | cacaggtacc | 960 |
| tctcaaaaca | ctagaatatc | cttacgcccg | gggccagtgt | ctcagccgta | ccaccactgg | 1020 |
| gacacagata | aatatgtcac | aggaataaat | gctatttctc | atggtcagac | cacttatggt | 1080 |
| aacgctgaag | acaaagagta | tcagcaagga | gtgggtagat | ttccaaatga | aaagaacag | 1140 |
| ctaaaacagt | tacagggttt | aaacatgcac | accgcttttc | ccaataaagg | aacccagcaa | 1200 |
| tttacagatc | aaattgagcg | cccccctaatg | gtgggttctg | tatggaacag | aagagccctt | 1260 |
| cactatgaaa | gccagctgtg | gagtaaaatt | ccaaatttag | atgacagttt | taaaactcag | 1320 |
| tttgcagcct | taggaggatg | gggtttgcat | cagccacctc | ctcaaatatt | tttaaaaata | 1380 |
| ttaccacaaa | gtgggccaat | tggaggtatt | aaatcaatgg | gaattactac | cttagttcag | 1440 |
| tatgccgtgg | gaattatgac | agtaaccatg | acatttaaat | tggggccccg | taaagctacg | 1500 |
| ggacggtgga | atcctcaacc | tggagtatat | cccccgcacg | cagcaggtca | tttaccatat | 1560 |
| gtactatatg | accctacagc | tacagatgca | aaacaacacc | acagacatgg | atatgaaaag | 1620 |
| cctgaagaat | gtggacagc | caaaagccgt | gtgcacccat | tgtaa | | 1665 |

<210> SEQ ID NO 25
<211> LENGTH: 1665
<212> TYPE: DNA
<213> ORGANISM: Artificial Sequence
<220> FEATURE:
<223> OTHER INFORMATION: Construct W

<400> SEQUENCE: 25

| | | | | | |
|---|---|---|---|---|---|
| atgacttcag | ttaattctgc | agaagccagc | actggtgcag | gagggggggg | cagtaatcct | 60 |
| gtcaaaagca | tgtggagtga | gggggccact | tttagtgcca | actctgtgac | ttgtacattt | 120 |

```
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt attttttca       300 cctttagagt ttcagcactt aattgaaaat tatggaagta tagctcctga tgctttaact      360
gtaaccatat cagaaattgc tgttaaggat gttacagaca aaactggagg ggggtgcag       420 gttactgaca gcactacagg gcgcctatgc atgttagtag accatgaata caagtaccca      480
tatgtgttag ggcaaggtca agatacttta gccccagaac ttcctatttg ggtatacttt      540 cccccctcaat atgcttactt aacagtagga gatgttaaca cacaaggaat ttctggagac     600
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca acactttat gagatgtaca atcccttata cggatcccgc       780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tgctgctgga gtgggtagat ttccaaatga aaagaacag     1140 ctaaaacagt tacaggggttt aaacatgcac accgcttttc ccaataaagg aacccagcaa    1200
tggacagatc aaattgagcg ccccctaatg gtgggttctg tatggaacag aagagccctt    1260
cactatgaaa gccagctgtg gagtaaaatt ccaaatttag atgacagttt taaaactcag    1320
tttgcagcct taggaggatg gggtttgcat cagccaccctc ctcaaatatt tttaaaaata   1380
ttaccacaaa gtgggccaat tggaggtatt aaatcaatgg gaattactac cttagttcag    1440
tatgccgtgg gaattatgac agtaaccatg acatttaaat tggggccccg taaagctacg    1500
ggacggtgga atcctcaacc tggagtatat cccccgcacg cagcaggtca tttaccatat    1560
gtactatatg accctacagc tacagatgca aaacaacacc acagacatgg atatgaaaag   1620
cctgaagaat tgtggacagc caaaagccgt gtgcacccat tgtaa                    1665
```

<210> SEQ ID NO 26
<211> LENGTH: 1665
<212> TYPE: DNA
<213> ORGANISM: Artificial Sequence
<220> FEATURE:
<223> OTHER INFORMATION: Construct X

<400> SEQUENCE: 26

```
atgacttcag ttaattctgc agaagccagc actggtgcag agggggggg cagtaatcct       60 gtcaaaagca tgtggagtga gggggccact tttagtgcca actctgtgac ttgtacattt      120
tctagacagt ttttaattcc atatgaccca gagcaccatt ataaggtgtt ttctcccgca      180
gcaagtagct gccacaatgc cagtggaaag gaggcaaagg tttgcaccat tagtcccata      240
atgggatact caaccccatg gagatattta gattttaatg ctttaaactt attttttca       300 cctttagagt ttcagcactt aattgaaaat tatggaagta tagctcctga tgctttaact      360
gtaaccatat cagaaattgc tgttaaggat gttacagaca aaactggagg ggggtgcag       420 gttactgaca gcactacagg gcgcctatgc atgttagtag accatgaata caagtaccca      480
```

```
tatgtgttag ggcaaggtca agatactttta gccccagaac ttcctatttg ggtatacttt      540 cccccctcaat atgcttactt aacagtagga gatgttaaca cacaaggaat ttctggagac      600
agcaaaaaat tagcaagtga agaatcagca ttttatgttt tggaacacag ttcttttcag      660
cttttaggta caggaggtac agcaactatg tcttataagt ttcctccagt gcccccagaa      720
aatttagagg gctgcagtca acacttttat gagatgtaca atcccttata cggatcccgc      780
ttaggggttc ctgacacatt aggaggtgac ccaaaattta gatctttaac acatgaagac      840
catgcaattc agccccaaaa cttcatgcca gggccactag taaactcagt gtctacaaag      900
gagggagaca gctctaatac tggagctggg aaagccttaa caggccttag cacaggtacc      960
tctcaaaaca ctagaatatc cttacgcccg gggccagtgt ctcagccgta ccaccactgg     1020
gacacagata aatatgtcac aggaataaat gctatttctc atggtcagac cacttatggt     1080
aacgctgaag acaaagagta tgctgctgga gtgggtagat ttccaaatga aaagaacag      1140 ctaaaacagt tacagggttt aaacatgcac accgcttttc ccaataaagg aacccagcaa     1200
tatacagatc aaattgagcg ccccctaatg gtgggttctg tatggaacag aagagccctt     1260
cactatgaaa gccagctgtg gagtaaaatt ccaaatttag atgacagttt taaaactcag     1320
tttgcagcct taggaggatg gggttttgcat cagccacctc ctcaaatatt tttaaaaata     1380
ttaccacaaa gtgggccaat tggaggtatt aaatcaatgg gaattactac cttagttcag     1440
tatgccgtgg gaattatgac agtaaccatg acatttaaat tggggccccg taaagctacg     1500
ggacggtgga atcctcaacc tggagtatat cccccgcacg cagcaggtca tttaccatat     1560
gtactatatg accctacagc tacagatgca aaacaacacc acagacatgg atatgaaaag     1620
cctgaagaat tgtggacagc caaaagccgt gtgcacccat tgtaa                     1665
```

<210> SEQ ID NO 27
<211> LENGTH: 31
<212> TYPE: DNA
<213> ORGANISM: Artificial Sequence
<220> FEATURE:
<223> OTHER INFORMATION: Wild type P1

<400> SEQUENCE: 27
atgatggaat tcatgacttc agttaattct g                                      31

<210> SEQ ID NO 28
<211> LENGTH: 35
<212> TYPE: DNA
<213> ORGANISM: Artificial Sequence
<220> FEATURE:
<223> OTHER INFORMATION: wild type P2

<400> SEQUENCE: 28
atgatgctcg agaagcttac aatgggtgca cacgg                                  35

<210> SEQ ID NO 29
<211> LENGTH: 30
<212> TYPE: DNA
<213> ORGANISM: Artificial Sequence
<220> FEATURE:
<223> OTHER INFORMATION: Construct A P1

<400> SEQUENCE: 29
ggggcgctca atttgatctg taaattgctg                                        30

<210> SEQ ID NO 30
<211> LENGTH: 30

```
<212> TYPE: DNA
<213> ORGANISM: Artificial Sequence
<220> FEATURE:
<223> OTHER INFORMATION: Construct A P2

<400> SEQUENCE: 30
cccaataaag gaacccagca atttacagat                                     30

<210> SEQ ID NO 31
<211> LENGTH: 30
<212> TYPE: DNA
<213> ORGANISM: Artificial Sequence
<220> FEATURE:
<223> OTHER INFORMATION: Construct B P1

<400> SEQUENCE: 31
ggggcgctca atttgatctg tccattgctg                                     30

<210> SEQ ID NO 32
<211> LENGTH: 30
<212> TYPE: DNA
<213> ORGANISM: Artificial Sequence
<220> FEATURE:
<223> OTHER INFORMATION: Construct B P2

<400> SEQUENCE: 32
cccaataaag gaacccagca atggacagat                                     30

<210> SEQ ID NO 33
<211> LENGTH: 30
<212> TYPE: DNA
<213> ORGANISM: Artificial Sequence
<220> FEATURE:
<223> OTHER INFORMATION: Construct C P1

<400> SEQUENCE: 33
ggggcgctca atttgatctg tagcttgctg                                     30

<210> SEQ ID NO 34
<211> LENGTH: 30
<212> TYPE: DNA
<213> ORGANISM: Artificial Sequence
<220> FEATURE:
<223> OTHER INFORMATION: Construct C P2

<400> SEQUENCE: 34
cccaataaag gaacccagca agctacagat                                     30

<210> SEQ ID NO 35
<211> LENGTH: 29
<212> TYPE: DNA
<213> ORGANISM: Artificial Sequence
<220> FEATURE:
<223> OTHER INFORMATION: Construct D P1

<400> SEQUENCE: 35
ggaaatctac ccactccagc agcatactc                                      29

<210> SEQ ID NO 36
<211> LENGTH: 30
<212> TYPE: DNA
<213> ORGANISM: Artificial Sequence
<220> FEATURE:
<223> OTHER INFORMATION: Construct D P2

<400> SEQUENCE: 36
```

```
gctgaagaca aagagtatgc tgctggagtg                                    30
```

<210> SEQ ID NO 37
<211> LENGTH: 29
<212> TYPE: DNA
<213> ORGANISM: Artificial Sequence
<220> FEATURE:
<223> OTHER INFORMATION: Construct E P1

<400> SEQUENCE: 37

```
ggaaatctac ccactccgtt gttatactc                                     29
```

<210> SEQ ID NO 38
<211> LENGTH: 30
<212> TYPE: DNA
<213> ORGANISM: Artificial Sequence
<220> FEATURE:
<223> OTHER INFORMATION: Construct E P2

<400> SEQUENCE: 38

```
gctgaagaca aagagtataa caacggagtg                                    30
```

<210> SEQ ID NO 39
<211> LENGTH: 47
<212> TYPE: DNA
<213> ORGANISM: Artificial Sequence
<220> FEATURE:
<223> OTHER INFORMATION: Construct F P1

<400> SEQUENCE: 39

```
cccaccatta gggggcgctc aatggtatct gtaaagttgt tggttcc                 47
```

<210> SEQ ID NO 40
<211> LENGTH: 51
<212> TYPE: DNA
<213> ORGANISM: Artificial Sequence
<220> FEATURE:
<223> OTHER INFORMATION: Construct F P2

<400> SEQUENCE: 40

```
cacacctact ttcccaataa aggaaccaac aactttacag ataccattga g            51
```

<210> SEQ ID NO 41
<211> LENGTH: 47
<212> TYPE: DNA
<213> ORGANISM: Artificial Sequence
<220> FEATURE:
<223> OTHER INFORMATION: Construct G P1

<400> SEQUENCE: 41

```
cccaccatta gggggcgctc aatggtatct gtatagttgt tggttcc                 47
```

<210> SEQ ID NO 42
<211> LENGTH: 51
<212> TYPE: DNA
<213> ORGANISM: Artificial Sequence
<220> FEATURE:
<223> OTHER INFORMATION: Construct G P2

<400> SEQUENCE: 42

```
cacacctact ttcccaataa aggaaccaac aactatacag ataccattga g            51
```

<210> SEQ ID NO 43
<211> LENGTH: 30
<212> TYPE: DNA
<213> ORGANISM: Artificial Sequence
<220> FEATURE:
<223> OTHER INFORMATION: Construct H P1

<400> SEQUENCE: 43
ctgggttcct ttattgggaa aagcggtgtg                                           30

<210> SEQ ID NO 44
<211> LENGTH: 27
<212> TYPE: DNA
<213> ORGANISM: Artificial Sequence
<220> FEATURE:
<223> OTHER INFORMATION: Construct H P2

<400> SEQUENCE: 44
ggtttaaaca tgcacaccgc ttttccc                                              27

<210> SEQ ID NO 45
<211> LENGTH: 30
<212> TYPE: DNA
<213> ORGANISM: Artificial Sequence
<220> FEATURE:
<223> OTHER INFORMATION: Construct I P1

<400> SEQUENCE: 45
ctgggttcct ttattgggaa aaaaggtgtg                                           30

<210> SEQ ID NO 46
<211> LENGTH: 27
<212> TYPE: DNA
<213> ORGANISM: Artificial Sequence
<220> FEATURE:
<223> OTHER INFORMATION: Construct I P2

<400> SEQUENCE: 46
ggtttaaaca tgcacacctt ttttccc                                              27

<210> SEQ ID NO 47
<211> LENGTH: 47
<212> TYPE: DNA
<213> ORGANISM: Artificial Sequence
<220> FEATURE:
<223> OTHER INFORMATION: Construct J P1

<400> SEQUENCE: 47
cccaccatta gggggcgctc aatgttatct gtaaagttgt tggttcc                        47

<210> SEQ ID NO 48
<211> LENGTH: 51
<212> TYPE: DNA
<213> ORGANISM: Artificial Sequence
<220> FEATURE:
<223> OTHER INFORMATION: Construct J P2

<400> SEQUENCE: 48
cacacctact ttcccaataa aggaaccaac aactttacag ataacattga g                   51

<210> SEQ ID NO 49
<211> LENGTH: 47
<212> TYPE: DNA
<213> ORGANISM: Artificial Sequence
<220> FEATURE:
<223> OTHER INFORMATION: Construct K P1

<400> SEQUENCE: 49
cccaccatta gggggcgctc aatgttatct gtatagttgt tggttcc                        47

```
<210> SEQ ID NO 50
<211> LENGTH: 51
<212> TYPE: DNA
<213> ORGANISM: Artificial Sequence
<220> FEATURE:
<223> OTHER INFORMATION: Construct K P2

<400> SEQUENCE: 50
cacacctact ttcccaataa aggaaccaac aactatacag ataacattga g        51

<210> SEQ ID NO 51
<211> LENGTH: 41
<212> TYPE: DNA
<213> ORGANISM: Artificial Sequence
<220> FEATURE:
<223> OTHER INFORMATION: Construct L P1

<400> SEQUENCE: 51
cccaccatta gggggcgctc aataccaatt ggatcttgat c                   41

<210> SEQ ID NO 52
<211> LENGTH: 36
<212> TYPE: DNA
<213> ORGANISM: Artificial Sequence
<220> FEATURE:
<223> OTHER INFORMATION: Construct L P2

<400> SEQUENCE: 52
cagcaatata cagatcaaga tccaattggt attgag                         36

<210> SEQ ID NO 53
<211> LENGTH: 28
<212> TYPE: DNA
<213> ORGANISM: Artificial Sequence
<220> FEATURE:
<223> OTHER INFORMATION: Construct M P1

<400> SEQUENCE: 53
ggcgctcaat tgatctgta taagcagc                                   28

<210> SEQ ID NO 54
<211> LENGTH: 30
<212> TYPE: DNA
<213> ORGANISM: Artificial Sequence
<220> FEATURE:
<223> OTHER INFORMATION: Construct M P2

<400> SEQUENCE: 54
acctactttc ccaataaagg aaccgctgct                                30

<210> SEQ ID NO 55
<211> LENGTH: 42
<212> TYPE: DNA
<213> ORGANISM: Artificial Sequence
<220> FEATURE:
<223> OTHER INFORMATION: Construct N P1

<400> SEQUENCE: 55
acccaccatt aggggggcgct caatagctgc agctggttgt tg                 42

<210> SEQ ID NO 56
<211> LENGTH: 39
<212> TYPE: DNA
<213> ORGANISM: Artificial Sequence
<220> FEATURE:
<223> OTHER INFORMATION: Construct N P2
```

```
<400> SEQUENCE: 56
acctactttc ccaataaagg aacccaacaa ccagctgca                             39

<210> SEQ ID NO 57
<211> LENGTH: 47
<212> TYPE: DNA
<213> ORGANISM: Artificial Sequence
<220> FEATURE:
<223> OTHER INFORMATION: Construct O P1

<400> SEQUENCE: 57
cccaccatta gggggcgctc aatggtatct gtccagttgt tggttcc                   47

<210> SEQ ID NO 58
<211> LENGTH: 51
<212> TYPE: DNA
<213> ORGANISM: Artificial Sequence
<220> FEATURE:
<223> OTHER INFORMATION: Construct O P2

<400> SEQUENCE: 58
cacacctact ttcccaataa aggaaccaac aactggacag ataccattga g              51

<210> SEQ ID NO 59
<211> LENGTH: 47
<212> TYPE: DNA
<213> ORGANISM: Artificial Sequence
<220> FEATURE:
<223> OTHER INFORMATION: Construct P P1

<400> SEQUENCE: 59
cccaccatta gggggcgctc aatggtatct gtccagttgt tggttcc                   47

<210> SEQ ID NO 60
<211> LENGTH: 51
<212> TYPE: DNA
<213> ORGANISM: Artificial Sequence
<220> FEATURE:
<223> OTHER INFORMATION: Construct P P2

<400> SEQUENCE: 60
cacacctact ttcccaataa aggaaccaac aactggacag ataccattga g              51

<210> SEQ ID NO 61
<211> LENGTH: 29
<212> TYPE: DNA
<213> ORGANISM: Artificial Sequence
<220> FEATURE:
<223> OTHER INFORMATION: Construct Q P1

<400> SEQUENCE: 61
ggaaatctac ccactccagc agcatactc                                       29

<210> SEQ ID NO 62
<211> LENGTH: 30
<212> TYPE: DNA
<213> ORGANISM: Artificial Sequence
<220> FEATURE:
<223> OTHER INFORMATION: Construct Q P2

<400> SEQUENCE: 62
gctgaagaca aagagtatgc tgctggagtg                                      30

<210> SEQ ID NO 63
```

```
<211> LENGTH: 29
<212> TYPE: DNA
<213> ORGANISM: Artificial Sequence
<220> FEATURE:
<223> OTHER INFORMATION: Construct R P1

<400> SEQUENCE: 63
ggaaatctac ccactccagc agcatactc                                    29

<210> SEQ ID NO 64
<211> LENGTH: 30
<212> TYPE: DNA
<213> ORGANISM: Artificial Sequence
<220> FEATURE:
<223> OTHER INFORMATION: Construct R P2

<400> SEQUENCE: 64
gctgaagaca aagagtatgc tgctggagtg                                   30

<210> SEQ ID NO 65
<211> LENGTH: 30
<212> TYPE: DNA
<213> ORGANISM: Artificial Sequence
<220> FEATURE:
<223> OTHER INFORMATION: Construct S P1

<400> SEQUENCE: 65
ctgggttcct ttattgggaa aagcggtgtg                                   30

<210> SEQ ID NO 66
<211> LENGTH: 27
<212> TYPE: DNA
<213> ORGANISM: Artificial Sequence
<220> FEATURE:
<223> OTHER INFORMATION: Construct S P2

<400> SEQUENCE: 66
ggtttaaaca tgcacaccgc ttttccc                                      27

<210> SEQ ID NO 67
<211> LENGTH: 29
<212> TYPE: DNA
<213> ORGANISM: Artificial Sequence
<220> FEATURE:
<223> OTHER INFORMATION: Construct T P1

<400> SEQUENCE: 67
ggaaatctac ccactccagc agcatactc                                    29

<210> SEQ ID NO 68
<211> LENGTH: 30
<212> TYPE: DNA
<213> ORGANISM: Artificial Sequence
<220> FEATURE:
<223> OTHER INFORMATION: Construct T P2

<400> SEQUENCE: 68
gctgaagaca aagagtatgc tgctggagtg                                   30

<210> SEQ ID NO 69
<211> LENGTH: 30
<212> TYPE: DNA
<213> ORGANISM: Artificial Sequence
<220> FEATURE:
<223> OTHER INFORMATION: Construct U P1

<400> SEQUENCE: 69
```

-continued

```
ctgggttcct ttattgggaa aagcggtgtg                                          30

<210> SEQ ID NO 70
<211> LENGTH: 27
<212> TYPE: DNA
<213> ORGANISM: Artificial Sequence
<220> FEATURE:
<223> OTHER INFORMATION: Construct U P2

<400> SEQUENCE: 70
ggtttaaaca tgcacaccgc ttttccc                                             27

<210> SEQ ID NO 71
<211> LENGTH: 30
<212> TYPE: DNA
<213> ORGANISM: Artificial Sequence
<220> FEATURE:
<223> OTHER INFORMATION: Construct V P1

<400> SEQUENCE: 71
ctgggttcct ttattgggaa aagcggtgtg                                          30

<210> SEQ ID NO 72
<211> LENGTH: 27
<212> TYPE: DNA
<213> ORGANISM: Artificial Sequence
<220> FEATURE:
<223> OTHER INFORMATION: Construct V P2

<400> SEQUENCE: 72
ggtttaaaca tgcacaccgc ttttccc                                             27

<210> SEQ ID NO 73
<211> LENGTH: 30
<212> TYPE: DNA
<213> ORGANISM: Artificial Sequence
<220> FEATURE:
<223> OTHER INFORMATION: Construct W P1

<400> SEQUENCE: 73
ctgggttcct ttattgggaa aagcggtgtg                                          30

<210> SEQ ID NO 74
<211> LENGTH: 27
<212> TYPE: DNA
<213> ORGANISM: Artificial Sequence
<220> FEATURE:
<223> OTHER INFORMATION: Construct W P2

<400> SEQUENCE: 74
ggtttaaaca tgcacaccgc ttttccc                                             27

<210> SEQ ID NO 75
<211> LENGTH: 29
<212> TYPE: DNA
<213> ORGANISM: Artificial Sequence
<220> FEATURE:
<223> OTHER INFORMATION: Construct X P1

<400> SEQUENCE: 75
ggaaatctac ccactccagc agcatactc                                           29

<210> SEQ ID NO 76
<211> LENGTH: 30
<212> TYPE: DNA
```

```
<213> ORGANISM: Artificial Sequence
<220> FEATURE:
<223> OTHER INFORMATION: Construct X P2

<400> SEQUENCE: 76
gctgaagaca aagagtatgc tgctggagtg                                    30
```